United States Patent
Watnick et al.

(10) Patent No.: US 9,359,275 B2
(45) Date of Patent: Jun. 7, 2016

(54) NATURAL PRODUCT ANTIBIOTICS AND ANALOGS THEREOF

(71) Applicants: Children's Medical Center Corporation, Boston, MA (US); President and Fellows of Harvard College, Cambridge, MA (US)

(72) Inventors: Paula I. Watnick, Waban, MA (US); Patrick Ymele-Leki, Silver Spring, MD (US); Jon Clardy, Jamaica Plain, MA (US); Shugeng Cao, Waltham, MA (US)

(73) Assignees: Children's Medical Center Corporation, Boston, MA (US); President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 13/776,144

(22) Filed: Feb. 25, 2013

(65) Prior Publication Data
US 2013/0245130 A1 Sep. 19, 2013

Related U.S. Application Data

(60) Provisional application No. 61/602,304, filed on Feb. 23, 2012.

(51) Int. Cl.
| | |
|---|---|
| *C07C 39/10* | (2006.01) |
| *C07C 39/11* | (2006.01) |
| *C07C 33/26* | (2006.01) |
| *C07D 307/79* | (2006.01) |
| *C07D 309/10* | (2006.01) |
| *C07C 50/38* | (2006.01) |

(52) U.S. Cl.
CPC .............. *C07C 39/10* (2013.01); *C07C 39/11* (2013.01); *C07C 50/38* (2013.01); *C07D 307/79* (2013.01); *C07D 309/10* (2013.01); *C07C 2103/24* (2013.01)

(58) Field of Classification Search
CPC ........ C07C 39/10; C07C 39/11; C07C 33/26; C07D 307/79
See application file for complete search history.

(56) References Cited

U.S. PATENT DOCUMENTS

| | | | |
|---|---|---|---|
| 4,426,444 A | 1/1984 | Postle et al. | |
| 4,443,537 A | 4/1984 | Postle et al. | |
| 4,966,907 A | 10/1990 | Caldwell et al. | |
| 5,324,809 A | 6/1994 | Sakashita et al. | |
| 5,329,010 A | 7/1994 | Okamoto et al. | |
| 5,563,129 A | 10/1996 | Masuya et al. | |

(Continued)

FOREIGN PATENT DOCUMENTS

| | | |
|---|---|---|
| CN | 101153866 | 4/2008 |
| EP | 664295 | 7/1995 |

OTHER PUBLICATIONS

Partial machine translation of Renz (J.Helvetica Chimica Acta, 1947, vol. 30. pp. 124-139) made on Apr. 30, 2014. Full translation ordered.*
Translation of Renz (J.Helvetica Chimica Acta, 1947, vol. 30. pp. 124-139) made on May 2014.*
PLOS One "A High-Throughput Screen Identifies a New Natural Product with Broad-Spectrum Antibacterial Activity", Feb. 16, 2012, vol. 7, issue 2, pp. 1-8.*
Andersen et al., "Accurate prediction of secondary metabolite gene clusters in filamentous fungi." Proc Natl Acad Sci U S A. Jan. 2, 2013;110(1):E99-107.
Anderson and Chung, "Conversion of versiconal acetate to versiconal and versicolorin C in extracts from Aspergillus parasiticus." Mycopathologia. Apr. 1990;110(1):31-5.

(Continued)

*Primary Examiner* — Kendra D Carter
(74) *Attorney, Agent, or Firm* — Wolf, Greenfield & Sacks, P.C.

(57) ABSTRACT

Provided herein are pure and isolated natural products and analogs thereof of Formula (I), (II), (III), and (IV), pharmaceutical compositions thereof, and methods of use, for example, for treating a bacterial infection. Further provided are methods useful in identifying an inhibitor of bacterial sugar fermentation in a bacterial strain, such as a compound (inhibitor) of Formula (I), (II), (III), or (IV):

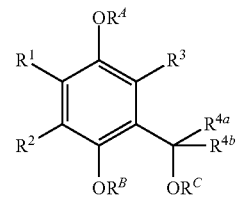

(I)

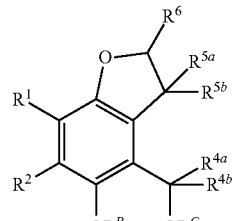

(II)

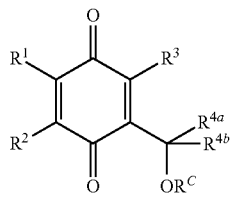

(III)

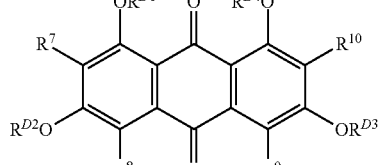

(IV)

or a pharmaceutically acceptable salt thereof.

7 Claims, 34 Drawing Sheets

(56) References Cited

U.S. PATENT DOCUMENTS

| | | | |
|---|---|---|---|
| 6,416,969 | B2 | 7/2002 | Matsumura et al. |
| 6,433,199 | B1 | 8/2002 | Ono et al. |
| 6,686,389 | B2 | 2/2004 | Ishikawa et al. |
| 7,070,625 | B2 | 7/2006 | Pasquier et al. |
| 7,622,481 | B2 * | 11/2009 | Axten et al. ............... 514/300 |
| 2009/0042932 | A1 * | 2/2009 | Lee et al. .................. 514/312 |
| 2009/0216002 | A1 | 8/2009 | Kleinebekel et al. |

OTHER PUBLICATIONS

Armstrong et al., "The introduction of n-alkyl groups into phenols and hydroquinones" Journal of the American Chemical Society (1960), 82, 1928-35.

Auffray and Boutibonnes, "Evaluation of the genotoxic activity of some mycotoxins using *Escherichia coli* in the SOS spot test." Mutat Res. Aug.-Sep. 1986;171(2-3):79-82.

Bolton et al., "Role of quinones in toxicology." Chem Res Toxicol. Mar. 2000;13(3):135-60.

Boutibonnes et al. "Antibacterial and genotoxic properties of 33 mycotoxins". Mycopathologia. Aug. 30, 1984;87(1-2):43-9.

Boutibonnes et al., "Antibacterial activity of 48 mycotoxins against Bacillus thuringiensis" Microbiologie, Aliments, Nutrition (1983), 1(3),259-64.

Campbell "High-throughput assessment of bacterial growth inhibition by optical density measurements" Curr Protoc Chem Biol. Oct. 1, 2011; 3(3).

Carlsson et al. "Interpretation of nonlinear QSAR models applied to Ames mutagenicity data." J Chem Inf Model. Nov. 2009;49(11):2551-8.

Cao et al., "Asterogynins: secondary metabolites from a Costa Rican endophytic fungus." Org Lett. Oct. 15, 2010;12(20):4661-3.

Chang et al. "The Aspergillus parasiticus estA-encoded esterase converts versiconal hemiacetal acetate to versiconal and versiconol acetate to versiconol in aflatoxin biosynthesis." Appl Environ Microbiol. Jun. 2004;70(6):3593-9.

Chen et al., "Reduction of sterigmatocystin and versicolorin A hemiacetals with sodium borohydride." J Org Chem. Oct. 28, 1977;42(22):3599-3605.

Chung, "Conversions of versiconal acetate and hemiacetals in cell-free extracts from Aspergillus parasiticus" Texas Tech Univ., Lubbock, TX, USA (1989) 116 pp. Avail.: Univ. Microfilms Int., Order No. DA9010721 From: Diss. Abstr. Int. B 1990, 50(11), 5031.

Churchill, "Part I: Carbon-13 nuclear magnetic resonance studies concerning the structure of versiconal acetate. Part II: Derivatization of organophosphorus pesticides and related phosphorothioates in the inlet block of a gas chromatograph. Part III: Extractive alkylation of niclosamide for gas-chromatographic analysis" Univ. Georgia, Athens, GA, USA (1980) 180 pp. Avail.: Univ. Microfilms Int., Order No. 8017159.

Cox et al., "Carbon-13 nuclear magnetic resonance studies of the structure and biosynthesis of versiconal acetate." J Am Chem Soc. Apr. 27, 1977;99(9):3159-61.

Ferrand et al., "Screening for mevalonate biosynthetic pathway inhibitors using sensitized bacterial strains." J Biomol Screen. Jul. 2011;16(6):637-46.

Fischbach and Walsh, "Antibiotics for emerging pathogens." Science. Aug. 28, 2009;325(5944): 1089-93.

Fredenhagen et al. "Paeciloquinones A, B, C, D, E and F: new potent inhibitors of protein tyrosine kinase produced by Paecilomyces carneus. II. Characterization and structure determination." J Antibiot (Tokyo). Mar. 1995;48(3):199-204.

Fredenhagen et al., "Protein tyrosine kinase and protein kinase C inhibition by fungal anthraquinones related to emodin." Antibiot (Tokyo). Nov. 1995;48(11):1355-8.

Hase and Barquera, "Role of sodium bioenergetics in Vibrio cholerae." Biochim Biophys Acta. May 1, 2001;1505(1):169-78.

Hatsuda et al., "Structure of a new metabolite from Aspergillus Versicolor" Agricultural and Biological Chemistry (1969), 33(1),131-3.

Högberg "Cyclo-oligomerization of Quinones IV" Acta Chem. Scand. 26 (1972) No. 7 2752-8.

Houot and Watnick, "A novel role for enzyme I of the Vibrio cholerae phosphoenolpyruvate phosphotransferase system in regulation of growth in a biofilm." J Bacteriol. Jan. 2008;190(1):311-20.

Houot et al., "The phosphoenolpyruvate phosphotransferase system regulates Vibrio cholerae biofilm formation through multiple independent pathways." J Bacteriol. Jun. 2010;192(12):3055-67.

Koyama et al., "Production of mycotoxins by Chaetomium species" Mycotoxins (1991), 33, 40-3.

Kusumoto and Hsieh, "Purification and characterization of the esterases involved in aflatoxin biosynthesis in Aspergillus parasiticus." Can J Microbiol. Aug. 1996;42(8):804-10.

Lee et al., "Bioactive metabolites from the sponge-derived fungus Aspergillus versicolor" College of Pharmacy, Pusan National University, Pusan, 609-735, S. Korea, (2010).

Liebeke et al., "Depletion of thiol-containing proteins in response to quinones in Bacillus subtilis." Mol Microbiol. Sep. 2008;69(6):1513-29.

Maes et al., "Polyketide-derived fungal metabolites from Bipolaris sorokiniana and their significance in the biosynthesis of sterigmatocystin and aflatoxin B1" Journal of the Chemical Society, Perkin Transactions 1: Organic and Bio-Organic Chemistry (1972-1999) (1984), (5), 1137-40.

Mandal et al., "Cholera: a great global concern." Asian Pac J Trop Med. Jul. 2011;4(7):573-80.

Matsushima et al. "Absence of aflatoxin biosynthesis in koji mold (Aspergillus sojae)." Appl Microbiol Biotechnol. Jun. 2001;55(6):771-6.

McCormack et al., "Evaluation of thiosulfate-citrate-bile salts-sucrose agar, a selective medium for the isolation of Vibrio cholerae and other pathogenic vibrios." J Infect Dis. May 1974;129(5):497-500.

McGuire and Townsend "Demonstration of Baeyer-Villiger oxidation and the course of cyclization in bisfuran ring formation during aflatoxin B1 biosynthesis" Bioorganic & Medicinal Chemistry Letters (1993),3(4),653-6.

Mohamad et al., Antituberculosis potential of some ethnobotanically selected Malaysian plants. J Ethnopharmacol. Feb. 16, 2011;133(3):1021-6.

Muh et al., "Novel Pseudomonas aeruginosa quorum-sensing inhibitors identified in an ultra-high-throughput screen. Antimicrob Agents Chemother." Nov. 2006;50(11):3674-9.

Pang et al. "Settling abalone veliger larvae in a free-swimming microalgal culture" Aquaculture 2006 258:327-336.

Parish et al., "Antisense-guided isolation and structure elucidation of pannomycin, a substituted cis-decalin from Geomyces pannorum." J Nat Prod. Jan. 2009;72(1):59-62.

Pereira et al. "High-throughput screening identifies novel inhibitors of the acetyltransferase activity of *Escherichia coli* GlmU." Antimicrob Agents Chemother. Jun. 2009;53(6):2306-11.

Petersen et al., "Paeciloquinones A, B, C, D, E and F: new potent inhibitors of protein tyrosine kinases produced by Paecilomyces carneus. 1. Taxonomy, fermentation, isolation and biological activity." J Antibiot (Tokyo). Mar. 1995;48(3):191-8.

Pfeffer and Oliver, "A comparison of thiosulphate-citrate-bile salts-sucrose (TCBS) agar and thiosulphate-chloride-iodide (TCI) agar for the isolation of Vibrio species from estuarine environments." Lett Appl Microbiol. 2003;36(3):150-1.

Ren et al., "Anthraquinone derivatives produced by marine-derived Penicillium flavidorsum SHK1-27 and their antitumor Activities" Zhongguo Yaowu Huaxue Zazhi (2007), 17(3), 148-154.

Renz, J. Helvetica Chimica Acta (1947), 30, 124-39.

Sakuno et al. "Aspergillus parasiticus cyclase catalyzes two dehydration steps in aflatoxin biosynthesis." Appl Environ Microbiol. Jun. 2005;71(6):2999-3006.

Schroeder et al., "Inhibition of aflatoxin production and tentative identification of an aflatoxin intermediate "versiconal acetate" from treatment with dichlorvos." Appl Microbiol. Feb. 1974;27(2):394-9.

Silva and Blokesch "Genetic manipulation of Vibrio cholera by combining natural transformation with FLP recombination" Plasmid 2010 64:186-195.

Singh and Hsieh, "Aflatoxin biosynthetic pathway: elucidation by using blocked mutants of Aspergillus parasiticus." Arch Biochem Biophys. Jan. 15, 1977;178(1):285-92.

(56) References Cited

OTHER PUBLICATIONS

Steyn et al., "Structure and carbon-13 nuclear magnetic resonance assignments of versiconal acetate, versiconol acetate, and versiconol, metabolites from cultures of Aspergillus parasiticus treated with dichlorvos" Journal of the Chemical Society, Perkin Transactions 1: Organic and Bio-Organic Chemistry (1972-1999) (1979), (2), 451-9.

Steyn et al., "Biosynthesis of versiconal acetate, versiconol acetate, and versiconol, metabolites from cultures of Aspergillus parasiticus treated with dichlorvos. The role of versiconal acetate in aflatoxin biosynthesis" Journal of the Chemical Society, Perkin Transactions 1: Organic and Bio-Organic Chemistry (1972-1999) (1979), (2), 460-3.

Tamura et al., "MEGA5: molecular evolutionary genetics analysis using maximum likelihood, evolutionary distance, and maximum parsimony methods." Mol Biol Evol. Oct. 2011;28(10):2731-9.

Waldor et al. "The Vibrio cholerae O139 serogroup antigen includes an O-antigen capsule and lipopolysaccharide virulence determinants." Proc Natl Acad Sci U S A. Nov. 22, 1994;91(24):11388-92.

Wen et al. "Function of the cypX and moxY genes in aflatoxin biosynthesis in Aspergillus parasiticus." Appl Environ Microbiol. Jun. 2005;71(6):3192-8.

Wong et al. "Mutagenicity of fungal metabolites related to aflatoxin biosynthesis." Mutat Res. Sep. 1977;44(3):447-50.

Yabe and Hamasaki, "Stereochemistry during aflatoxin biosynthesis: cyclase reaction in the conversion of versiconal to versicolorin B and racemization of versiconal hemiacetal acetate." Appl Environ Microbiol. Aug. 1993;59(8):2493-500.

Yabe et al. "A metabolic grid among versiconal hemiacetal acetate, versiconol acetate, versiconol and versiconal during aflatoxin biosynthesis." J Gen Microbiol. Oct. 1991;137(10):2469-75.

Yabe et al. "Enzymatic conversion of averufin to hydroxyversicolorone and elucidation of a novel metabolic grid involved in aflatoxin biosynthesis." Appl Environ Microbiol. Jan. 2003;69(1):66-73.

Yamazaki et al., "Monoamine oxidase inhibitors from a fungus, Emericella navahoensis." Chem Pharm Bull (Tokyo). Feb. 1988;36(2):670-5.

Ymele-Leki "A high-throughput screen identifies a new natural product with broad-spectrum antibacterial activity" PLoS One. 2012;7(2): Feb. 16, 2012.

Yu et al., "Cloning and functional expression of an esterase gene in Aspergillus parasitcus." Mycopathologia. 2002;156(3):227-34.

Zhang et al., "A Simple Statistical Parameter for Use in Evaluation and Validation of High Throughput Screening Assays." J Biomol Screen. 1999;4(2):67-73.

Renz, Darstellung und antibakterielle Wirksamkeit einiger im Kern substituier-ter Derivate des Gentisinalkohols. Helv Chim Acta. Feb. 1, 1947;30(1):124-39.

Shima et al., Participation in aflatoxin biosynthesis by a reductase enzyme encoded by vrdA gene outside the aflatoxin gene cluster. Fungal Genet Biol. Mar. 2009;46(3):221-31. doi: 10.1016/j.fgb. 2008.12.005. Epub Jan. 3, 2009.

Birkinshaw et al., Studies in the biochemistry of micro-organisms: 72. Gentisyl alcohol (2:5-dihydroxybenzyl alcohol), a metabolic product of Penicillium patulum Bainier. Biochem J. 1943;37(6):726-8.

Gopal et al., Reactive dirty fragments: implications for tuberculosis drug discovery. Curr Opin Microbiol. Oct. 2014;21:7-12. doi: 10.1016/j.mib.2014.06.015. Epub Jul. 30, 2014.

Kavanagh et al., The use of surveillance and preventative measures for methicillin-resistant *Staphylococcus aureus* infections in surgical patients. Antimicrob Resist Infect Control. May 14, 2014;3:18. doi: 10.1186/2047-2994-3-18. eCollection 2014.

Newsom et al., MRSA—past, present, future. J R Soc Med. Nov. 2004;97(11):509-10.

\* cited by examiner

NATURAL PRODUCT ANTIBIOTICS AND ANALOGS THEREOF

RELATED APPLICATIONS

The present application claims the benefit under 35 U.S.C. §119(e) of U.S. provisional patent application, U.S. Ser. No. 61/602,304, filed Feb. 23, 2012, which is incorporated herein by reference.

GOVERNMENT SUPPORT

This invention was made with government support under AI50032 awarded by the National Institutes of Health. The government has certain rights in the invention.

BACKGROUND

The emergence of bacteria with resistance to multiple antimicrobial agents has increased the need to discover new antibiotics.

SUMMARY

The emergence of bacteria with resistance to multiple antimicrobial agents has motivated the development of high throughput chemical screens (HTS) to identify novel antibiotics. These screens differ in the number of samples that can reasonably be evaluated and the level of technology required to carry out the screen. See, e.g., Mohamad et al., *J Ethnopharmacol* (2011) 133: 1021-1026; Muh et al., *Antimicrob Agents Chemother* (2006) 50: 3674-3679; Parish et al., *J Nat Prod* (2009) 72: 59-62; Pereira et al., *Antimicrob Agents Chemother* (2009) 53: 2306-2311. Furthermore, some screening assays assess inhibition of a known, purified bacterial target, while others measure toxicity to intact bacteria. The advantage of the former approach is that the target of inhibition is known for any identified compound. The great disadvantage, however, is that, in secondary screens, the compound is often found to have no activity against intact bacteria due to inadequate penetration, rapid efflux, or inactivation by bacterial products. See, e.g., Fischbach et al., *Science* (2009) 325: 1089-1093. For this reason, compounds discovered in screens using whole cells are often farther along the path to the development of a successful antibacterial agent.

Described herein is a colorimetric, whole cell-based screen, such as a colorimetric, whole cell-based screen high throughput screen (HTS), for antibacterial compounds. This assay is useful to screen, for example, crude extracts from organisms, e.g., endophytic fungi. As described herein, the method has been used to screen a collection of more than 39,000 crude extracts from organisms that grow in the diverse ecosystems of Costa Rica. Forty-nine antibacterial extracts with reproducible antibacterial effects were identified. Extracts from endophytic fungi, obtained as described herein, were further characterized, resulting in the identification of several natural products, encompassed by Formula (I), (II), (III), and (IV), as described below. Results presented herein demonstrate the utility of simple metabolic screens in rapid identification of novel, broadspectrum antimicrobial agents.

Thus, in one aspect, provided is a compound of Formula (I):

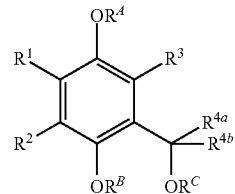

or a pharmaceutically acceptable salt thereof;
wherein:
each occurrence of $R^1$, $R^2$, $R^{4a}$, and $R^{4b}$, is independently hydrogen or halogen;
$R^A$ is hydrogen, substituted or unsubstituted $C_{1-3}$ alkyl, $-C(=O)R^{A2}$, $-C(=O)OR^{A1}$, $-C(=O)SR^{A1}$, $-C(=O)N(R^{A1})_2$, $-S(=O)_2R^{A2}$, $-S(=O)_2OR^{A1}$, $-P(=O)_2R^{A2}$, $-P(=O)_2OR^{A1}$, $-P(=O)(OR^{A1})_2$, $-P(=O)(R^{A2})_2$, or $-P(=O)(R^{A2})(OR^{A1})$;
$R^B$ is hydrogen, substituted or unsubstituted $C_{1-3}$ alkyl, $-C(=O)R^{B2}$, $-C(=O)OR^{B1}$, $-C(=O)SR^{B1}$, $C(=O)N(R^{B1})_2$, $-S(=O)_2R^{B2}$, $-S(=O)_2OR^{B1}$, $-P(=O)_2R^{B2}$, $-P(=O)_2OR^{B1}$, $-P(=O)(OR^{B1})_2$, $-P(=O)(R^{B2})_2$, or $-P(=O)(R^{B2})(OR^{B1})$;
$R^C$ is hydrogen, substituted or unsubstituted $C_{1-3}$ alkyl, $-C(=O)R^{C2}$, $-C(=O)OR^{C1}$, $-C(=O)SR^{C1}$, $-C(=O)N(R^{C1})_2$, $-S(=O)_2R^{C2}$, $-S(=O)_2OR^{C1}$, $-P(=O)_2R^{C2}$, $-P(=O)_2OR^{C1}$, $-P(=O)(OR^{C1})_2$, $-P(=O)(R^{C2})_2$, or $-P(=O)(R^{C2})(OR^{C1})$;
each occurrence of $R^{A1}$, $R^{B1}$, and $R^{C1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{A1}$ groups, two $R^{B1}$ groups, and/or two $R^{C1}$ groups are joined to form an substituted or unsubstituted heterocyclic or substituted or unsubstituted heteroaryl ring;
each occurrence of $R^{A2}$, $R^{B2}$, and $R^{C2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and
$R^3$ is substituted or unsubstituted $C_2$-$C_{10}$alkyl.

In certain embodiments, the compound of Formula (I) is a pure and isolated compound of formula:

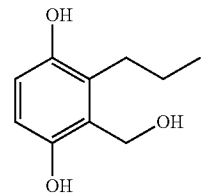

or a pharmaceutically acceptable salt thereof.

In another aspect, provided is a compound of Formula (II):

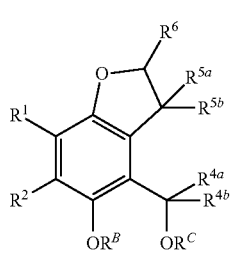

(II)

or a pharmaceutically acceptable salt thereof;
wherein:

each occurrence of $R^1$, $R^2$, $R^{4a}$, $R^{4b}$, $R^{5a}$, and $R^{5b}$, hydrogen or halogen;

$R^B$ is hydrogen, substituted or unsubstituted $C_{1-3}$ alkyl, —C(=O)$R^{B2}$, —C(=O)O$R^{B1}$, —C(=O)S$R^{B1}$, —C(=O)N($R^{B1}$)$_2$, —S(=O)$_2$$R^{B2}$, —S(=O)$_2$O$R^{B1}$, —P(=O)$_2$$R^{B2}$, —P(=O)$_2$O$R^{B1}$, —P(=O)(O$R^{B1}$)$_2$, —P(=O)($R^{B2}$)$_2$, or —P(=O)($R^{B2}$)(O$R^{B1}$);

$R^C$ is hydrogen, substituted or unsubstituted $C_{1-3}$ alkyl, —C(=O)$R^{C2}$, —C(=O)O$R^{C1}$, —C(=O)S$R^{C1}$, —(=O)N($R^{C1}$)$_2$, —S(=O)$_2$$R^{C2}$, —S(=O)$_2$O$R^{C1}$, —P(=O)$_2$$R^{C2}$, —P(=O)$_2$O$R^{C1}$, —P(=O)(O$R^{C1}$)$_2$, —P(=O)($R^{C2}$)$_2$, or —P(=O)($R^{C2}$)(O$R^{C1}$);

each occurrence of $R^{B1}$ and $R^{C1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{B1}$ groups and/or two $R^{C1}$ groups are joined to form an substituted or unsubstituted heterocyclic or substituted or unsubstituted heteroaryl ring;

each occurrence of $R^{B2}$ and $R^{C2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^6$ is substituted or unsubstituted $C_1$-$C_6$alkyl.

In certain embodiments, the compound of Formula (II) is a pure and isolated compound of formula:

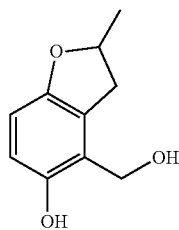

or a pharmaceutically acceptable salt thereof.

In another aspect, provided is a compound of Formula (III):

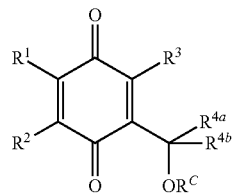

(III)

or a pharmaceutically acceptable salt thereof;
wherein:

each occurrence of $R^1$, $R^2$, $R^{4a}$, and $R^{4b}$, is independently hydrogen or halogen;

$R^C$ is hydrogen, substituted or unsubstituted $C_{1-3}$ alkyl, —C(=O)$R^{C2}$, —C(=O)O$R^{C1}$, —C(=O)S$R^{C1}$, —C(=O)N($R^{C1}$)$_2$, —S(=O)$_2$$R^{C2}$, —S(=O)$_2$O$R^{C1}$, —P(=O)$_2$$R^{C2}$, —P(=O)$_2$O$R^{C1}$, —P(=O)(O$R^{C1}$)$_2$, —P(=O)($R^{C2}$)$_2$, or —P(=O)($R^{C2}$)(O$R^{C1}$);

each occurrence of $R^{C1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{C1}$ groups are joined to form an substituted or unsubstituted heterocyclic or substituted or unsubstituted heteroaryl ring;

$R^{C2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^3$ is substituted or unsubstituted $C_2$-$C_{10}$alkyl.

In certain embodiments, the compound of Formula (III) is a pure and isolated compound of formula:

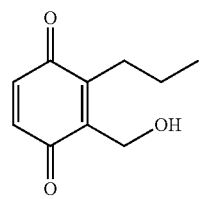

or a pharmaceutically acceptable salt thereof.

In another aspect, provided is a compound of Formula (IV):

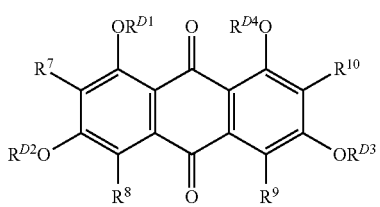

(IV)

or a pharmaceutically acceptable salt thereof;

wherein:

each occurrence of $R^7$, $R^8$, and $R^9$ is independently hydrogen or halogen;

each occurrence of $R^{D1}$, $R^{D2}$, $R^{D3}$, and $R^{D4}$ is independently hydrogen, substituted or unsubstituted $C_{1-3}$ alkyl, —C(=O)$R^{D6}$, —C(=O)O$R^{D5}$, —C(=O)S$R^{D5}$, —C(=O)N($R^{D5}$)$_2$, —S(=O)$_2R^{D6}$, —S(=O)$_2$O$R^{D5}$, —P(=O)$_2R^{D6}$, —P(=O)$_2$O$R^{D5}$, —P(=O)(O$R^{D5}$)$_2$, —P(=O)($R^{D6}$)$_2$, or —P(=O)($R^{D6}$)(O$R^{D5}$);

each occurrence of $R^{D5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{D5}$ groups are joined to form an substituted or unsubstituted heterocyclic or substituted or unsubstituted heteroaryl ring;

$R^{D6}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^{10}$ is a group of formula:

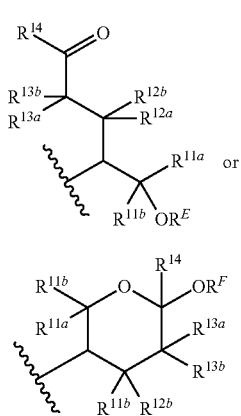

wherein each instance of $R^{11a}$, $R^{11b}$, $R^{12a}$, $R^{12b}$, $R^{13a}$, and $R^{13b}$ is independently hydrogen, substituted or unsubstituted $C_{1-3}$ alkyl, or halogen; and $R^{14}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^E$ is hydrogen, substituted or unsubstituted $C_{1-3}$ alkyl, —C(=O)$R^{E2}$, —C(=O)O$R^{E1}$, —C(=O)S$R^{E1}$, —C(=O)N($R^{E1}$)$_2$, —S(=O)$_2R^{E2}$, —S(=O)$_2$O$R^{E1}$, —P(=O)$_2R^{E2}$, —P(=O)$_2$O$R^{E1}$, —P(=O)(O$R^{E1}$)$_2$, —P(=O)($R^{E2}$)$_2$, or —P(=O)($R^{E2}$)(O$R^{E1}$), wherein each occurrence of $R^{E1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{E1}$ groups are joined to form an substituted or unsubstituted heterocyclic or substituted or unsubstituted heteroaryl ring; and $R^{E2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^F$ is hydrogen, substituted or unsubstituted $C_{1-3}$ alkyl, —C(=O)$R^{F2}$, —C(=O)O$R^{F1}$, —C(=O)S$R^{F1}$, —C(=O)N($R^{F1}$)$_2$, —S(=O)$_2R^{F2}$, —S(=O)$_2$O$R^{F1}$, P(=O)$_2R^{F2}$, —P(=O)$_2$O$R^{F1}$, —P(=O)(O$R^{F1}$)$_2$, —P(=O)($R^{F2}$)$_2$, or —P(=O)($R^{F2}$)(O$R^{F1}$), wherein each occurrence of $R^{F1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{F1}$ groups are joined to form an substituted or unsubstituted heterocyclic or substituted or unsubstituted heteroaryl ring; and $R^{F2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, the compound of Formula (IV) is a pure and isolated compound of formula:

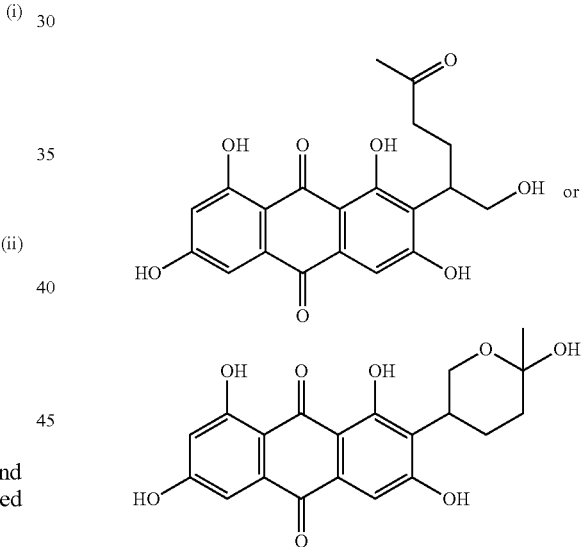

or a pharmaceutically acceptable salt thereof.

In yet another aspect, provided are pharmaceutical compositions comprising a compound of Formula (I), (II), (III), or (IV), or pharmaceutically acceptable salt thereof, and a pharmaceutically acceptable excipient.

In still yet another aspect, provided are methods of treating a bacterial infection in a subject comprising administering an effective amount of a compound of Formula (I), (II), (III), or (IV), or pharmaceutically acceptable salt thereof, to the subject. In certain embodiments, the bacterial infection is an *Escherichia coli*, *Pseudomonas aeruginosa*, *Vibrio cholerae*, methicillin-resistant *Staphylococcus aureus*, or *Mycobacterium tuberculosis* infection.

In still yet another aspect, provided is a method of identifying an inhibitor of bacterial sugar fermentation in a bacterial strain, the method comprising:

(a) combining a candidate compound and a bacterial strain in which sugar transport depends on the phosphoenolpyruvate phosphotransferase system thereby producing a combination;

(b) culturing the combination in media comprising a sugar and one or more pH indicators under conditions appropriate for sugar fermentation by the bacterial strain; and (c) determining if sugar fermentation occurs in the combination cultured in (b), wherein if sugar fermentation does not occur or is reduced in the combination cultured in (b), relative to the extent to which fermentation occurs under the same conditions except that the candidate compound is not present, the candidate compound is an inhibitor of bacterial sugar fermentation.

In certain embodiments, the method comprises at least two pH indicators. In certain embodiments, one or more pH indicators are protonated at about a pH<7.1. In certain embodiments, at least one pH indicator is deprotonated at about a pH between 7.1 and 8.0. In certain embodiments, at least one pH indicator is protonated at about a pH between 7.1 and 8.0. In certain embodiments, at least one pH indicator is deprotonated at about a pH>8.0. In certain embodiments, method comprises bromothymol blue and thymol blue as pH indicators.

In certain embodiments, the sugar is sucrose.

In certain embodiments, the candidate compound is a compound of Formula (I), (II), (III), or (IV), or a pharmaceutically acceptable salt thereof.

In certain embodiments, the bacterial strain is *Escherichia coli*, *Pseudomonas aeruginosa*, *Vibrio cholerae*, methicillin-resistant *Staphylococcus aureus*, or *Mycobacterium tuberculosis*.

The details of one or more embodiments of the invention are set forth in the accompanying Figures and the Detailed Description. Other features, objects, and advantages of the invention will be apparent from the description and from the claims.

DEFINITIONS

Figure 1:
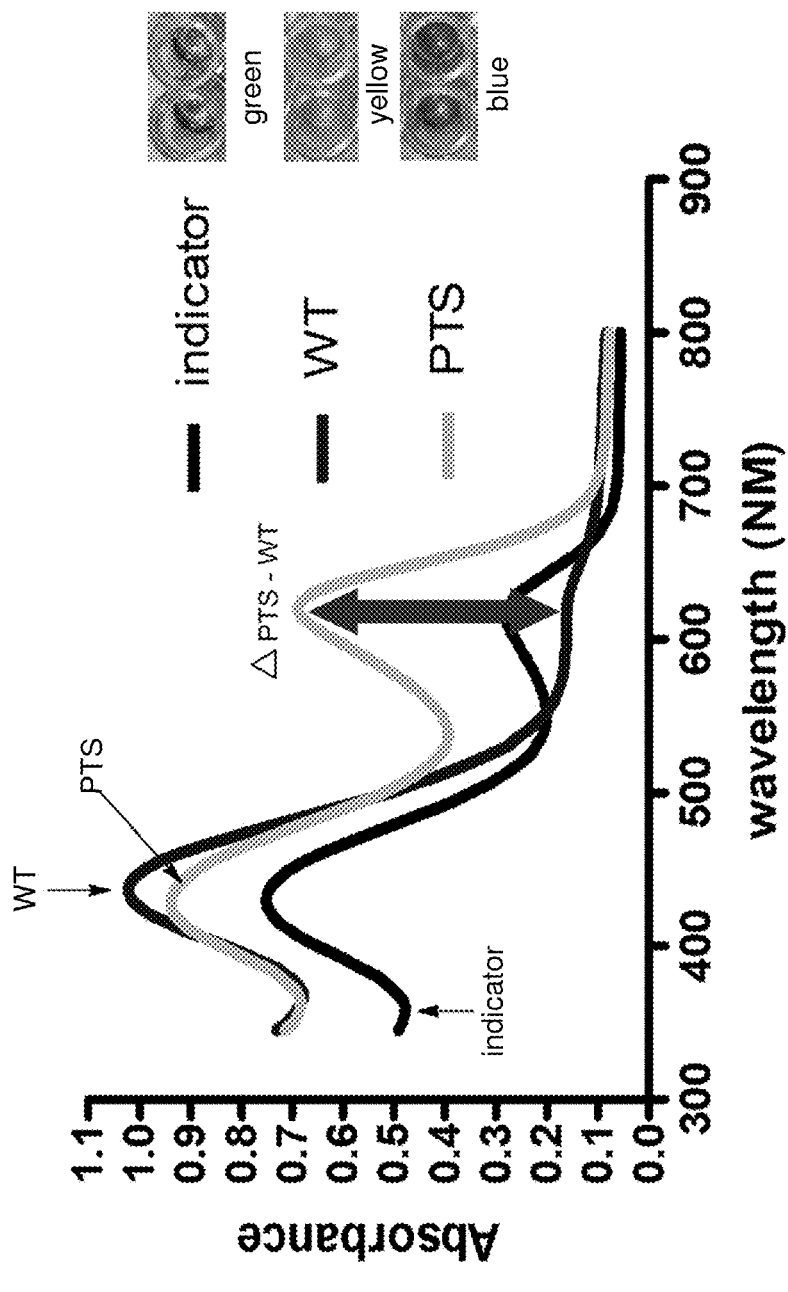
FIG. 1 depicts the Spectrophotometric assay for bacterial sugar fermentation. Absorbance spectrum of MMSuc alone (indicator) or incubated with wild-type *V. cholerae* (WT) or a PTS mutant for 5 hours. The spectra are shown at the left, while a visible color difference is shown in microtiter dish wells at the right. The largest difference in absorbance between MMSuc incubated with wild-type *V. cholerae* and that incubated with a PTS mutant is measured at 615 nm (double headed arrow).

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

As used herein, an "isolated" compound means a compound not in a cell or organism and which is separated from some or all of the components that typically accompany it in nature, e.g., from the biomass or extract from which it was obtained. Isolation of bioactive compounds from a biomass may employ a number of different chromatographic separation techniques which include, but are not limited to, thin layer chromatography (TLC), high performance liquid chromatography (HPLC), flash chromatography, and Sephadex chromatography. Non-chromatographic techniques such as immunoassay, which use monoclonal antibodies (MAbs), phytochemical screening assay, Fourier-transform infrared spectroscopy (FTIR), can also be used to isolate and facilitate identification of the compound. The structure of the isolated compounds may be determined using a number of analytical techniques which include, but are not limited to, X-ray crystallography, infrared (IR) spectroscopy, ultraviolet (UV) spectroscopy, 1D and 2D nuclear magnetic resonance (NMR) spectroscopy, and mass spectroscopy.

As used herein, a "pure" compound indicates that the isolated compound is substantially free of other compounds (contaminants). "Substantially free" in this context indicates the compound comprises less than 10%, less than 9%, less than 8%, less than 7%, less than 6%, less than 5%, less than 4%, less than 3%, less than 2%, less than 1%, less than 0.5%, less than 0.1%, e.g., less than between about 0.1% to about 10%, of other compounds and/or contaminants as determined analytically, e.g., by NMR spectroscopy.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$), n-nonyl ($C_9$), n-decyl ($C_{10}$), and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclyl ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-10}$ cycloalkyl. In certain embodiments, the cycloalkyl group is a substituted C$_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR', —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR', —ON(R$^{ff}$)$_2$, —N(R$^{ff}$)$_2$, —N(R$^{ff}$)$_3^+$X$^-$, —N(OR')R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R', —C(=O)N(R$^f$)$_2$, —OC(=O)N(R$^f$)$_2$, —NR$^{ff}$C(=O)R', —NR$^{ff}$CO$_2$R$^{ee}$, —NR$^{ff}$C(=O)N(R$^f$)$_2$, —C(=NR$^{ff}$)OR', —OC(=NR$^{ff}$)R$^{ee}$, —OC(=NR$^{ff}$)OR', —C(=NR$^{ff}$)N(R$^f$)$_2$, —OC(=NR$^{ff}$)N(R$^f$)$_2$, —NR$^{ff}$C(=NR$^{ff}$)N(R$^f$)$_2$, —NR$^{ff}$SO$_2$R$^{ee}$, —SO$_2$N(R$^f$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^f$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-5}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$alkyl)$_2$, —OC(=O)NH(C$_{1-6}$alkyl), —NHC(=O)(C$_{1-6}$ alkyl), —N(C$_{1-6}$ alkyl)C(=O)(C$_{1-6}$ alkyl), —NHCO$_2$(C$_{1-5}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$alkyl), —P(=O)(C$_{1-6}$alkyl)$_2$, —OP(=O)(C$_{1-6}$alkyl)$_2$, —OP(=O)(OC$_{1-6}$alkyl)$_2$, C$_{1-6}$ alkyl, C$_{1-6}$ perhaloalkyl, C$_{2-6}$ alkenyl, C$_{2-6}$ alkynyl, C$_{1-6}$heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on an oxygen atom is an oxygen protecting group (also referred to herein as an "hydroxylprotecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1- benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

These and other exemplary substituents are described in more detail in the Detailed Description, Examples, and claims. The invention is not intended to be limited in any manner by the above exemplary listing of substituents.

OTHER DEFINITIONS

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is infected (e.g., tested positive, and/or suffering from symptoms associate with) a bacterial infection, which reduces the severity of bacterial infection, or retards or slows the progression of the bacterial infection ("therapeutic treatment").

In general, the "effective amount" or "therapeutically effective amount" of a compound refers to an amount sufficient to provide a therapeutic benefit in the treatment of the bacterial infection, or to delay or reduce/minimize one or more symptoms associated with the bacterial infection. The "effective amount" or "therapeutically effective amount" can encompass an amount that improves overall therapy, reduces or avoids symptoms of the bacterial infection, and/or enhances the therapeutic efficacy of another therapeutic agent.

DETAILED DESCRIPTION OF CERTAIN EMBODIMENTS OF THE INVENTION

Described here is the development of a sensitive and robust, low-tech and inexpensive high throughput metabolic, whole cell-based screening method for identification of new antibiotics. This screen is based on a colorimetric assay of pH that identifies inhibitors of bacterial sugar (e.g., sucrose) fermentation. After validation of the method, more than 39,000 crude extracts derived from organisms that grow in the diverse ecosystems of Costa Rica were screened. This resulted in identification of over 49 extracts with reproducible antibacterial effects. An extract from endophytic fungi were further characterized, resulting in the isolation and purification of several natural products, referred to as Compounds 1, 2, 3, SC3-22-3, and SC3-22-19. Compound 1, also referred to as mirandamycin, has broad-spectrum anti-bacterial activity against *Escherichia coli, Pseudomonas aeruginosa, Vibrio cholerae*, methicillin-resistant *Staphylococcus aureus*, and *Mycobacterium tuberculosis*. Compound 2 also demonstrated anti-bacterial activity. Compound SC3-22-19 caused decreased sugar utilization that can be due either to blocking transport and utilization and/or to bacterial killing.

This method demonstrates the power of simple high throughput screens for rapid identification of new antibacterial agents from environmental samples.

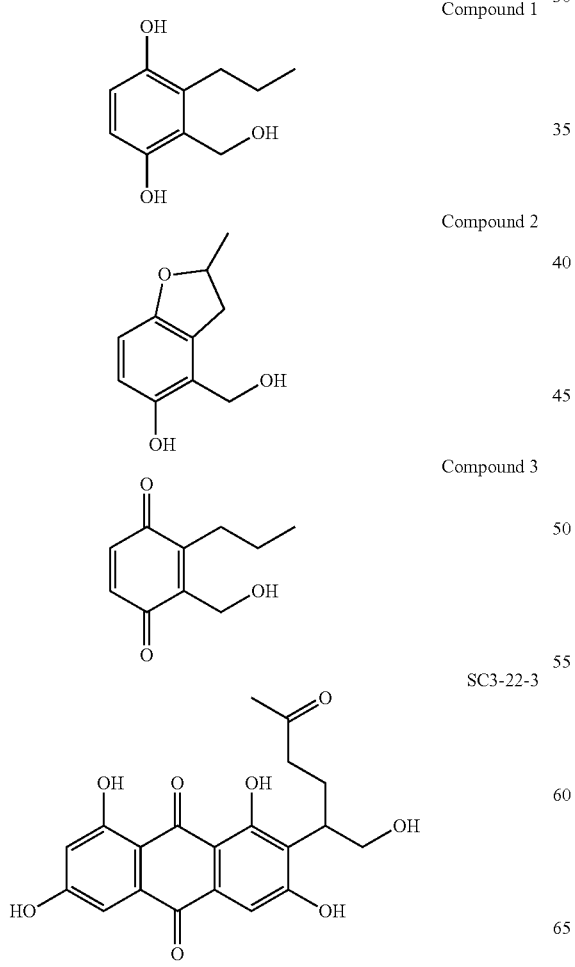

Compound 1

Compound 2

Compound 3

SC3-22-3

SC3-22-19

Compounds 1, 2, 3, SC3-22-3, and SC3-22-19 were isolated from fungal biomass. The present invention contemplates the pure and isolated forms of these natural products, analogs of these natural products, as well as pharmaceutical compositions and methods of using these natural products and analogs thereof, for example, for treating bacterial infections.

Compounds of Formula (I), (II), and (III)

In one aspect, provided is a compound of Formula (I), (II), or (III):

(I)

(II)

(III)

or a pharmaceutically acceptable salt thereof;
wherein:
each occurrence of $R^1$, $R^2$, $R^{4a}$, $R^{4b}$, $R^{5a}$, is independently hydrogen or halogen;

$R^A$ is hydrogen, substituted or unsubstituted $C_{1-3}$ alkyl, —C(=O)$R^{A2}$, —C(=O)O$R^{A1}$, —C(=O)S$R^{A1}$, —C(=O)N($R^{A1}$)$_2$, —S(=O)$_2R^{A2}$, —S(=O)$_2$O$R^{A1}$, —P(=O)$_2R^{A2}$, —P(=O)$_2$O$R^{A1}$, —P(=O)(O$R^{A1}$)$_2$, —P(=O)($R^{A2}$)$_2$, or —P(=O)($R^A$)(O$R^{A1}$);

$R^B$ is hydrogen, substituted or unsubstituted $C_{1-3}$ alkyl, —C(=O)$R^{B2}$, —C(=O)O$R^{B1}$, —C(=O)S$R^{B1}$, —C(=O)N($R^{B1}$)$_2$, —S(=O)$_2R^{B2}$, —S(=O)$_2$O$R^{B1}$, —P(=O)$_2R^{B2}$, —P(=O)$_2$O$R^{B1}$, —P(=O)(O$R^{B1}$)$_2$, —P(=O)($R^{B2}$)$_2$, or —P(=O)($R^{B2}$)(O$R^{B1}$);

$R^C$ is hydrogen, substituted or unsubstituted $C_{1-3}$ alkyl, —C(=O)$R^{C2}$, —C(=O)O$R^{C1}$, —C(=O)S$R^{C1}$, —C(=O)

N($R^{C1}$)$_2$, —S(=O)$_2$$R^{C2}$, —S(=O)$_2$O$R^{C1}$, —P(=O)$_2$$R^{C2}$, —P(=O)$_2$O$R^{C1}$, —P(=O)(O$R^{C1}$)$_2$, —P(=O)($R^{C2}$)$_2$, or —P(=O)($R^{C2}$)(O$R^{C1}$);

each occurrence of $R^{A1}$, $R^{B1}$, and $R^{C1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{A1}$ groups, two $R^{B1}$ groups, and/or two $R^{C1}$ groups are joined to form an substituted or unsubstituted heterocyclic or substituted or unsubstituted heteroaryl ring;

each occurrence of $R^{A2}$, $R^{B2}$, and $R^{C2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^3$ is substituted or unsubstituted $C_2$-$C_{10}$alkyl; and $R^6$ is substituted or unsubstituted $C_1$-$C_6$alkyl.

In certain embodiments, the compound of Formula (I), (II), or (III), or pharmaceutically acceptable salt thereof, is a pure and isolated compound of Formula (I), (II), or (III), or pharmaceutically acceptable salt thereof, as defined herein.

Prodrugs of the compounds of Formula (I), (II), or (III) are contemplated herein. For example, a prodrug of a compound of Formula (I), (II), or (III) may refer to a compound (I), (II), or (III) having a group —O$R^A$, —O$R^B$, and/or —O$R^C$ wherein at least one of $R^A$, $R^B$, and/or $R^C$ is a non-hydrogen group which cleaves under physiological conditions to the free hydroxyl group (—OH), and which results in a pharmaceutically active compound in vivo. Exemplary cleavable groups include groups —C(=O)$R^{A2}$, —C(=O)O$R^{A1}$, —C(=O)S$R^{A1}$, —C(=O)N($R^{A1}$)$_2$, —S(=O)$_2$$R^{A2}$, —S(=O)$_2$O$R^{A1}$, —P(=O)$_2$$R^{A2}$, —P(=O)$_2$O$R^{A1}$, —P(=O)(O$R^{A1}$)$_2$, —P(=O)($R^{A2}$)$_2$, or —P(=O)($R^{A2}$)(O$R^{A1}$) of $R^A$; groups —C(=O)$R^{B2}$, —C(=O)O$R^{B1}$, —C(=O)S$R^{B1}$, —C(=O)N($R^{B1}$)$_2$, —S(=O)$_2$$R^{B2}$, —S(=O)$_2$O$R^{B1}$, —P(=O)$_2$$R^{B2}$, —P(=O)$_2$O$R^{B1}$, —P(=O)(O$R^{B1}$)$_2$, —P(=O)($R^{B2}$)$_2$, or —P(=O)($R^{B2}$)(O$R^{B1}$) of $R^B$; and groups —C(=O)$R^{C2}$, —C(=O)O$R^{C1}$, —C(=O)S$R^{C1}$, —C(=O)N($R^{C1}$)$_2$, —S(=O)$_2$$R^{C2}$, —S(=O)$_2$O$R^{C1}$, —P(O)$_2$$R^{C2}$, —P(=O)$_2$O$R^{C1}$, —P(=O)(O$R^{C1}$)$_2$, —P(=O)($R^{C2}$)$_2$, or —P(=O)($R^{C2}$)(O$R^{C1}$) of $R^C$.

In certain embodiments, at least one of (e.g., one, two, or all three of) $R^A$, $R^B$, and/or $R^C$ is a non-hydrogen group.

As generally defined herein, each occurrence of $R^1$, $R^2$, $R^{4a}$, $R^{4b}$, —$R^{5a}$, and $R^{5b}$, is independently hydrogen or halogen.

In certain embodiments, $R^1$ is hydrogen. In certain embodiments, $R^1$ is halogen, e.g., fluoro, chloro, bromo, or iodo. In certain embodiments, $R^1$ is hydrogen or fluoro.

In certain embodiments, $R^2$ is hydrogen. In certain embodiments, $R^2$ is halogen, e.g., fluoro, chloro, bromo, or iodo. In certain embodiments, $R^2$ is hydrogen or fluoro.

In certain embodiments, at least one instance of $R^{4a}$ and $R^{4b}$ is hydrogen. In certain embodiments, at least one instance of $R^{4a}$ and $R^{4b}$ is halogen, e.g., fluoro, chloro, bromo, or iodo. In certain embodiments, at least one instance of $R^{4a}$ and $R^{4b}$ is hydrogen or fluoro. In certain embodiments, each instance of $R^{4a}$ and $R^{4b}$ is hydrogen. In certain embodiments, each instance of $R^{4a}$ and $R^{4b}$ is fluoro.

In certain embodiments, at least one instance of $R^{5a}$ and $R^{5b}$ is hydrogen. In certain embodiments, at least one instance of $R^{5a}$ and $R^{5b}$ is halogen, e.g., fluoro, chloro, bromo, or iodo. In certain embodiments, at least one instance of $R^{5a}$ and $R^{5b}$ is hydrogen or fluoro. In certain embodiments, each instance of $R^{5a}$ and $R^{5b}$ is hydrogen. In certain embodiments, each instance of $R^{5a}$ and $R^{5b}$ is fluoro.

In certain embodiments, each instance of $R^1$ and $R^2$ is hydrogen.

In certain embodiments, each instance of $R^1$, $R^2$, $R^{4a}$, and $R^{4b}$ is hydrogen.

In certain embodiments, each instance of $R^1$, $R^2$, $R^{4a}$, $R^{4b}$, $R^{5a}$, and $R^{5b}$ is hydrogen.

As generally defined herein, $R^A$ is hydrogen, substituted or unsubstituted $C_{1-3}$ alkyl, —C(=O)$R^{A2}$, —C(=O)O$R^{A1}$, —C(=O)S$R^{A1}$, —C(=O)N($R^{A1}$)$_2$, —S(=O)$_2$$R^{A2}$, —S(=O)$_2$O$R^{A1}$, —P(=O)$_2$$R^{A2}$, —P(=O)$_2$O$R^{A1}$, —P(=O)(O$R^{A1}$)$_2$, —P(=O)($R^{A2}$)$_2$, or —P(=O)($R^{A2}$)(O$R^{A1}$), wherein each occurrence of $R^{A1}$ and $R^{A2}$ is as define herein.

In certain embodiments, $R^A$ is hydrogen.

In certain embodiments, $R^A$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

In certain embodiments, $R^A$ is —C(=O)$R^{A2}$, —C(=O)O$R^{A1}$, —C(=O)S$R^{A1}$, or —C(=O)N($R^{A1}$)$_2$, wherein $R^{A1}$ and $R^{A2}$ are as defined herein.

In certain embodiments, $R^A$ is —C(=O)$R^{A2}$, e.g., for example, wherein $R^{A2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^A$ is —C(=O)$CH_3$.

In certain embodiments, $R^A$ is —C(=O)O$R^{A1}$, e.g., for example, wherein $R^{A1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^A$ is —C(=O)O$CH_3$.

In certain embodiments, $R^A$ is —C(=O)S$R^{A1}$, e.g., for example, wherein $R^{A1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^A$ is —C(=O)SCH$_3$.

In certain embodiments, $R^A$ is —C(=O)N($R^{A1}$)$_2$, e.g., —C(=O)NH$_2$ or —C(=O)NH$R^{A1}$, wherein $R^{A1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$), or $R^A$ is —C(=O)N($R^{A1}$)$_2$ wherein the two $R^{A1}$ groups are joined to form a substituted or unsubstituted heterocyclic or heteroaryl ring.

In certain embodiments, $R^A$ is —S(=O)$_2R^{A2}$ or —S(=O)$_2$O$R^{A1}$, wherein $R^{A2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{A1}$ is hydrogen or any of the aforementioned groups. In certain embodiments, $R^A$ is —S(=O)$_2R^{A2}$. In certain embodiments, $R^A$ is —S(=O)$_2$O$R^{A1}$, e.g., —SO$_3$H.

In certain embodiments, $R^A$ is —P(=O)$_2R^{A2}$, —P(=O)$_2$O$R^{A1}$, —P(=O)(O$R^{A1}$)$_2$, —P(=O)($R^{A2}$)$_2$, or —P(=O)($R^{A2}$)(O$R^{A1}$), wherein $R^{A2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{A1}$ is hydrogen or any of the aforementioned groups. In certain embodiments, $R^A$ is —P(=O)$_2R^{A2}$. In certain embodiments, $R^A$ is —P(=O)$_2$O$R^{A1}$. In certain embodiments, $R^A$ is —P(=O)(O$R^{A1}$)$_2$. In certain embodiments, $R^A$ is —P(=O)($R^{A2}$)$_2$. In certain embodiments, $R^A$ is —P(=O)($R^{A2}$)(O$R^{A1}$).

As generally defined herein, $R^B$ is hydrogen, substituted or unsubstituted $C_{1-3}$ alkyl, —C(=O)$R^{B2}$, —C(=O)O$R^{B1}$, —C(=O)S$R^{B1}$, —C(=O)N($R^{B1}$)$_2$, —S(=O)$_2R^{B2}$, —S(=O)$_2$O$R^{B1}$, —P(=O)$_2R^{B2}$, —P(=O)$_2$O$R^{B1}$, —P(=O)(O$R^{B1}$)$_2$, —P(=O)($R^{B2}$)$_2$, or —P(=O)($R^{B2}$)(O$R^{B1}$), wherein each occurrence of $R^{B1}$ and $R^{B2}$ is as defined herein.

In certain embodiments, $R^B$ is hydrogen.

In certain embodiments, $R^B$ is substituted or unsubstituted $C_{1-3}$ alkyl, e.g., substituted or unsubstituted $C_{1-2}$ alkyl, substituted or unsubstituted $C_{2-3}$ alkyl, substituted or unsubstituted $C_1$ alkyl, substituted or unsubstituted $C_2$ alkyl, or substituted or unsubstituted $C_3$ alkyl. Exemplary $C_{1-3}$ alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

In certain embodiments, $R^B$ is —C(=O)$R^{B2}$, —C(=O)O$R^{B1}$, —C(=O)S$R^{B1}$, or —C(=O)N($R^{B1}$)$_2$, wherein $R^{B1}$ and $R^{B2}$ are as defined herein.

In certain embodiments, $R^B$ is —C(=O)$R^{B2}$, e.g., for example, wherein $R^{B2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^B$ is —C(=O)CH$_3$.

In certain embodiments, $R^B$ is —C(=O)O$R^{B1}$, e.g., for example, wherein $R^{B1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^B$ is —C(=O)OCH$_3$.

In certain embodiments, $R^B$ is —C(=O)S$R^{B1}$, e.g., for example, wherein $R^{B1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^B$ is —C(=O)SCH$_3$.

In certain embodiments, $R^B$ is —C(=O)N($R^{B1}$)$_2$, e.g., —C(=O)NH$_2$ or —C(=O)NH$R^{B1}$, wherein $R^{B1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$), or $R^B$ is —C(=O)N($R^{B1}$)$_2$ wherein the two $R^{B1}$ groups are joined to form a substituted or unsubstituted heterocyclic or heteroaryl ring.

In certain embodiments, $R^B$ is —S(=O)$_2R^{B2}$ or —S(=O)$_2$O$R^{B1}$, wherein $R^{B2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{B1}$ is hydrogen or any of the aforementioned groups. In certain embodiments, $R^B$ is —S(=O)$_2R^{B2}$. In certain embodiments, $R^B$ is —S(=O)$_2$O$R^{B1}$, e.g., —SO$_3$H.

In certain embodiments, $R^B$ is —P(=O)$_2R^{B2}$, —P(=O)$_2$O$R^{B1}$, —P(=O)(O$R^{B1}$)$_2$, —P(=O)($R^{B2}$)$_2$, or —P(=O)($R^{B2}$)(O$R^{B1}$), wherein $R^{B2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{B1}$ is hydrogen or any of the aforementioned groups. In certain embodiments, $R^B$ is —P(=O)$_2R^{B2}$. In certain embodiments, $R^B$ is —P(=O)$_2$O$R^{B1}$. In certain embodiments, $R^B$ is —P(=O)(O$R^{B1}$)$_2$. In certain embodiments, $R^B$ is —P(=O)($R^{B2}$)$_2$. In certain embodiments, $R^B$ is —P(=O)($R^{B2}$)(O$R^{B1}$).

In certain embodiments, $R^A$ and $R^B$ are the same group. In certain embodiments, however, $R^A$ and $R^B$ are different groups.

As generally defined herein, $R^C$ is hydrogen, substituted or unsubstituted $C_{1-3}$ alkyl, —C(=O)$R^{C2}$, —C(=O)O$R^{C1}$, —C(=O)S$R^{C1}$, —C(=O)N($R^{C1}$)$_2$, —S(=O)$_2R^{C2}$, —S(=O)$_2$O$R^{C1}$, —P(=O)$_2R^{C2}$, —P(=O)$_2$O$R^{C1}$, —P(=O)(O$R^{C1}$)$_2$, —P(=O)($R^{C2}$)$_2$, or —P(=O)($R^{C2}$)(O$R^{C1}$), wherein each occurrence of $R^{C1}$ and $R^{C2}$ is as define herein.

In certain embodiments, $R^C$ is hydrogen.

In certain embodiments, $R^C$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

In certain embodiments, $R^C$ is —C(=O)$R^{C2}$, —C(=O)O$R^{C1}$, —C(=O)S$R^{C1}$, or —C(=O)N($R^{C1}$)$_2$, wherein $R^{C1}$ and $R^{C2}$ are as defined herein.

In certain embodiments, $R^C$ is —C(=O)$R^{C2}$, e.g., for example, wherein $R^{C2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^C$ is —C(=O)CH$_3$.

In certain embodiments, $R^C$ is —C(=O)O$R^{C1}$, e.g., for example, wherein $R^{C1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^C$ is —C(=O)OCH$_3$.

In certain embodiments, $R^C$ is —C(=O)S$R^{C1}$, e.g., for example, wherein $R^{C1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^C$ is —C(=O)SCH$_3$.

In certain embodiments, $R^C$ is —C(=O)N($R^{C1}$)$_2$, e.g., —C(=O)NH$_2$ or —C(=O)NHR$^{C1}$, wherein $R^{C1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$), or $R^C$ is —C(=O)N($R^{C1}$)$_2$ wherein the two $R^{C1}$ groups are joined to form a substituted or unsubstituted heterocyclic or heteroaryl ring.

In certain embodiments, $R^C$ is —S(=O)$_2R^{C2}$ or —S(=O)$_2$O$R^{C1}$, wherein $R^{C2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{C1}$ is hydrogen or any of the aforementioned groups. In certain embodiments, $R^C$ is —S(=O)$_2R^{C2}$. In certain embodiments, $R^C$ is —S(=O)$_2OR^{C1}$, e.g., —SO$_3$H.

In certain embodiments, $R^C$ is —P(=O)$_2R^{C2}$, —P(=O)$_2$OR$^{C1}$, —P(=O)(OR$^{C1}$)$_2$, —P(=O)(R$^{C2}$)$_2$, or —P(=O)(R$^{C2}$)(OR$^{C1}$), wherein $R^{C2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{C1}$ is hydrogen or any of the aforementioned groups. In certain embodiments, $R^C$ is —P(=O)$_2R^{C2}$. In certain embodiments, $R^C$ is —P(=O)$_2$OR$^{C1}$. In certain embodiments, $R^C$ is —P(=O)(OR$^{C1}$)$_2$. In certain embodiments, $R^C$ is —P(=O)(R$^{C2}$)$_2$. In certain embodiments, $R^C$ is —P(=O)(R$^{C2}$)(OR$^{C1}$).

In certain embodiments, $R^A$ and $R^C$ are the same group. In certain embodiments, however, $R^A$ and $R^C$ are different groups.

In certain embodiments, $R^B$ and $R^C$ are the same group. In certain embodiments, however, $R^B$ and $R^C$ are different groups.

In certain embodiments, each of $R^A$, $R^B$, and $R^C$ is the same group, e.g., hydrogen or C(=O)CH$_3$.

As generally defined herein, $R^3$ is substituted or unsubstituted $C_2$-$C_{10}$alkyl, e.g., substituted or unsubstituted $C_2$-$C_9$alkyl, substituted or unsubstituted $C_2$-$C_8$alkyl, substituted or unsubstituted $C_2$-$C_7$alkyl, substituted or unsubstituted $C_2$-$C_6$alkyl, substituted or unsubstituted $C_2$-$C_5$alkyl, substituted or unsubstituted $C_2$-$C_4$alkyl, substituted or unsubstituted $C_2$-$C_3$alkyl, substituted or unsubstituted $C_3$-$C_6$alkyl, substituted or unsubstituted $C_3$-$C_5$alkyl, or substituted or unsubstituted $C_3$-$C_4$alkyl. In certain embodiments, $R^3$ is substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), substituted or unsubstituted n-heptyl ($C_7$), substituted or unsubstituted n-octyl ($C_8$), substituted or unsubstituted n-nonyl ($C_9$), or substituted or unsubstituted n-decyl ($C_{10}$). In certain embodiments, $R^3$ is substituted or unsubstituted n-propyl ($C_3$), e.g., —CH$_2$CH$_2$CH$_3$.

As generally defined herein, $R^6$ is substituted or unsubstituted $C_1$-$C_6$alkyl, e.g., substituted or unsubstituted $C_1$-$C_5$alkyl, substituted or unsubstituted $C_1$-$C_4$alkyl, substituted or unsubstituted $C_1$-$C_3$alkyl, or substituted or unsubstituted $C_1$-$C_2$alkyl. In certain embodiments, $R^6$ is substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^6$ is substituted or unsubstituted methyl ($C_1$), e.g., —CH$_3$.

Various combinations of the above embodiments are contemplated. For example, in certain embodiments, wherein $R^1$ and $R^2$ of Formula (I), (II), and (III) are hydrogen, provided are compounds of Formula (I-a), (II-a), and (III-a):

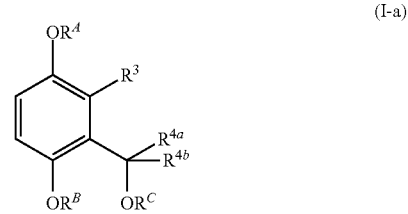

(I-a)

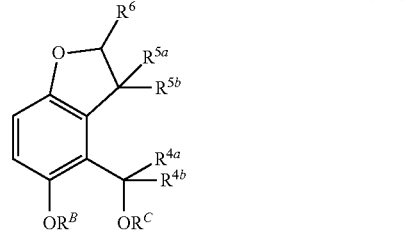

(II-a)

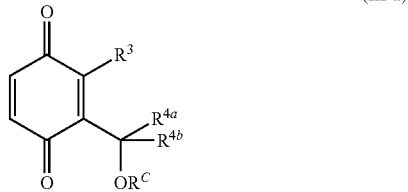

(III-a)

and pharmaceutically acceptable salts thereof. In certain embodiments, $R^A$ is hydrogen or —C(=O)R$^{A2}$. In certain embodiments, $R^B$ is hydrogen or —C(=O)R$^{B2}$. In certain embodiments, $R^C$ is hydrogen or —C(=O)R$^{C2}$. In certain embodiments, $R^{4a}$ and $R^{4b}$ are hydrogen. In certain embodiments, $R^{5a}$ and $R^{5b}$ are hydrogen. In certain embodiments, $R^6$ is —CH$_3$. In certain embodiments, $R^3$ is substituted or unsubstituted n-propyl.

In certain embodiments, wherein each of $R^1$, $R^2$, $R^{4a}$, and $R^{4b}$ are hydrogen, provided are compounds of Formula (I-b), (II-b), and (III-b):

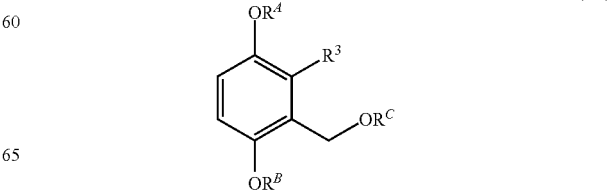

(I-b)

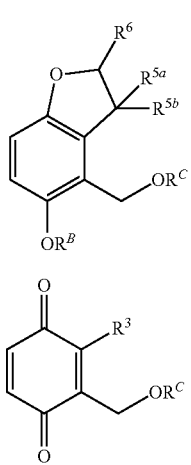

(II-b)

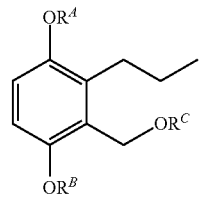

(I-b)

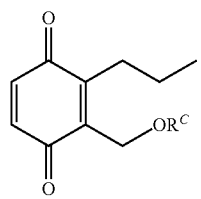

(III-b)

and pharmaceutically acceptable salts thereof. In certain embodiments, $R^A$ is hydrogen or —C(=O)$R^{A2}$. In certain embodiments, $R^B$ is hydrogen or —C(=O)$R^{B2}$. In certain embodiments, $R^C$ is hydrogen or —C(=O)$R^{C2}$. In certain embodiments, $R^{5a}$ and $R^{5b}$ are hydrogen. In certain embodiments, $R^6$ is —CH$_3$. In certain embodiments, $R^3$ is substituted or unsubstituted n-propyl.

In certain embodiments, wherein each of $R^1$, $R^2$, $R^{4a}$, $R^{4b}$, $R^{5a}$, and $R^{5b}$ are hydrogen, provided are compounds of Formula (II-c):

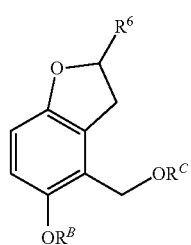

(II-c)

and pharmaceutically acceptable salts thereof. In certain embodiments, $R^B$ is hydrogen or —C(=O)$R^{B2}$. In certain embodiments, $R^C$ is hydrogen or —C(=O)$R^{C2}$. In certain embodiments, $R^6$ is —CH$_3$.

In certain embodiments, wherein each of $R^1$, $R^2$, $R^{4a}$, $R^{4b}$, $R^{5a}$, and $R^{5b}$ are hydrogen, and $R^6$ is methyl, provided are compounds of Formula (II-c):

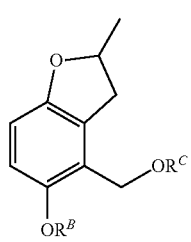

(II-d)

and pharmaceutically acceptable salts thereof. In certain embodiments, $R^B$ is hydrogen or —C(=O)$R^{B2}$. In certain embodiments, $R^C$ is hydrogen or —C(=O)$R^{C2}$.

In certain embodiments, wherein each of $R^1$, $R^2$, $R^{4a}$, and $R^{4b}$ are hydrogen, and $R^3$ is n-propyl, provided are compounds of Formula (I-c) and (III-c):

and pharmaceutically acceptable salts thereof. In certain embodiments, $R^A$ is hydrogen or —C(=O)$R^{A2}$. In certain embodiments, $R^B$ is hydrogen or —C(=O)$R^{B2}$. In certain embodiments, $R^C$ is hydrogen or —C(=O)$R^{C2}$.

In certain embodiments, the compound of Formula (I) is the pure and isolated compound of formula:

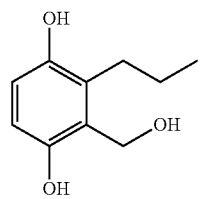

and pharmaceutically acceptable salts thereof. However, in certain embodiments, the above compound is specifically excluded. In certain embodiments, prodrugs of the above compound are contemplated.

In certain embodiments, the compound of Formula (II) is the pure and isolated compound of formula:

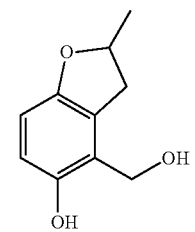

and pharmaceutically acceptable salts thereof. In certain embodiments, prodrugs of the above compound are contemplated.

In certain embodiments, the compound of Formula (III) is the pure and isolated compound of formula:

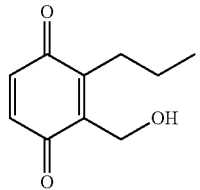

and pharmaceutically acceptable salts thereof. In certain embodiments, prodrugs of the above compound are contemplated.

Compounds of Formula (IV)

In another aspect, provided is a compound of Formula (IV):

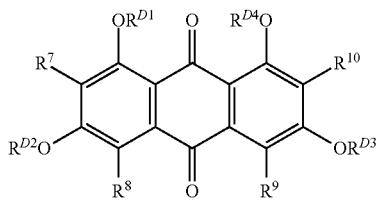

or a pharmaceutically acceptable salt thereof;
wherein:

each occurrence of $R^7$, $R^8$, and $R^9$ is independently hydrogen or halogen; each occurrence of $R^{D1}$, $R^{D2}$, $R^{D3}$, and $R^{D4}$ is independently hydrogen, substituted or unsubstituted $C_{1-3}$ alkyl, —C(=O)$R^{D6}$, —C(=O)O$R^{D5}$, —C(=O)S$R^{D5}$, —C(=O)N($R^{D5}$)$_2$, —S(=O)$_2R^{D6}$, —S(=O)$_2$O$R^{D5}$, —P(=O)$_2R^{D6}$, —P(=O)$_2$O$R^{D5}$, —P(=O)(O$R^{D5}$)$_2$, —P(=O)($R^{D6}$)$_2$, or —P(=O)($R^{D6}$)(O$R^{D5}$);

each occurrence of $R^{D5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{D5}$ groups are joined to form an substituted or unsubstituted heterocyclic or substituted or unsubstituted heteroaryl ring;

$R^{D6}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^{10}$ is a group of formula:

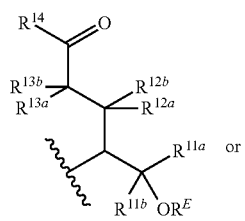

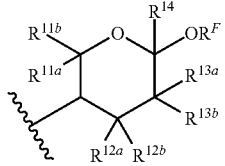

wherein each instance of $R^{11a}$, $R^{11b}$, $R^{12a}$, $R^{12b}$, $R^{13a}$, and $R^{13b}$ is independently hydrogen, substituted or unsubstituted $C_{1-3}$ alkyl, or halogen;

$R^{14}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^E$ is hydrogen, substituted or unsubstituted $C_{1-3}$ alkyl, —C(=O)$R^{E2}$, —C(=O)O$R^{E1}$, —C(=O)S$R^{E1}$, —C(=O)N($R^{E1}$)$_2$, —S(=O)$_2R^{E2}$, —S(=O)$_2$O$R^{E1}$, —P(=O)$_2R^{E2}$, —P(=O)$_2$O$R^{E1}$, —P(=O)(O$R^{E1}$)$_2$, —P(=O)($R^{E2}$)$_2$, or —P(=O)($R^{E2}$)(O$R^{E1}$), wherein each occurrence of $R^{E1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{E1}$ groups are joined to form an substituted or unsubstituted heterocyclic or substituted or unsubstituted heteroaryl ring; and $R^{E2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^F$ is hydrogen, substituted or unsubstituted $C_{1-3}$ alkyl, —C(=O)$R^{F2}$, —C(=O)O$R^{F1}$, —C(=O)S$R^{F1}$, —C(=O)N($R^{F1}$)$_2$, —S(=O)$_2R^{F2}$, —S(=O)$_2$O$R^{F1}$, —P(=O)$_2R^{F2}$, —P(=O)$_2$O$R^{F1}$, —P(=O)(O$R^{F1}$)$_2$, —P(=O)($R^{F2}$)$_2$, or —P(=O)($R^{F2}$)(O$R^{F1}$), wherein each occurrence of $R^{F1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; or two $R^{F1}$ groups are joined to form an substituted or unsubstituted heterocyclic or substituted or unsubstituted heteroaryl ring; and $R^{F2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, the compound of Formula (IV), or pharmaceutically acceptable salt thereof, is a pure and isolated compound of Formula (IV), or pharmaceutically acceptable salt thereof, as defined herein.

Prodrugs of the compounds of Formula (IV) are contemplated herein. For example, a prodrug of a compound of Formula (IV) may refer to a compound (IV) having a group —O$R^{D1}$, —O$R^{D2}$, —O$R^{D3}$, —O$R^{D4}$, —$R^E$ and/or —O$R^F$, wherein at least one of $R^{D1}$, $R^{D2}$, $R^{D3}$, $R^{D4}$, $R^E$, and/or $R^F$ is a non-hydrogen group which cleaves under physiological conditions to the free hydroxyl group (—OH), and which results in a pharmaceutically active compound in vivo. Exemplary cleavable groups include groups —C(=O)$R^{D6}$, —C(=O)$OR^{D5}$, —C(=O)$SR^{D5}$, —C(=O)N($R^{D5}$)$_2$, —S(=O)$_2R^{D6}$, —S(=O)$_2OR^{D5}$, —P(=O)$_2R^{D6}$, —P(=O)$_2$ $OR^{D5}$, —P(=O)($OR^{D5}$)$_2$, —P(=O)($R^{D6}$)$_2$, or —P(=O)($R^{D6}$)($OR^{D5}$) of $R^{D1}$, $R^{D2}$, $R^{D3}$, and $R^{D4}$; groups —C(=O)$R^{E2}$, —C(=O)$OR^{E1}$, —C(=O)$SR^{E1}$, —C(=O)N($R^{E1}$)$_2$, —S(=O)$_2R^{E2}$, —S(=O)$_2OR^{E1}$, —P(=O)$_2R^{E2}$, —P(=O)$_2$ $OR^{E1}$, —P(=O)($OR^{E1}$)$_2$, —P(=O)($R^{E2}$)$_2$, or —P(=O)($R^{E2}$)($OR^{E1}$) of $R^E$; and groups —C(=O)$R^{F2}$, —C(=O)$OR^{F1}$, —C(=O)$SR^{F1}$, —C(=O)N($R^{F1}$)$_2$, —S(=O)$R^{F2}$, —S(=O)$_2OR^{F1}$, —P(=O)$_2R^{F2}$, —P(=O)$_2$ $OR^{F1}$, —P(=O)($OR^{F1}$)$_2$, —P(=O)($R^{F2}$)$_2$, or —P(=O) ($R^{F2}$)($OR^{F1}$) of $R^F$.

In certain embodiments, at least one of (e.g., one, two, three, four, five, or all six of) $R^{D1}$, $R^{D2}$, $R^{D3}$, $R^{D4}$, $R^E$, and/or $R^F$ is a non-hydrogen group.

As generally defined herein, each occurrence of $R^7$, $R^8$, and $R^9$ is independently hydrogen or halogen.

In certain embodiments, $R^7$ is hydrogen. In certain embodiments, $R^7$ is halogen, e.g., fluoro, chloro, bromo, or iodo. In certain embodiments, $R^7$ is hydrogen or fluoro.

In certain embodiments, $R^8$ is hydrogen. In certain embodiments, $R^8$ is halogen, e.g., fluoro, chloro, bromo, or iodo. In certain embodiments, $R^8$ is hydrogen or fluoro.

In certain embodiments, $R^9$ is hydrogen. In certain embodiments, $R^9$ is halogen, e.g., fluoro, chloro, bromo, or iodo. In certain embodiments, $R^9$ is hydrogen or fluoro.

In certain embodiments, each instance of $R^7$ and $R^8$ is hydrogen. In certain embodiments, each instance of $R^7$ and $R^9$ is hydrogen. In certain embodiments, each instance of $R^8$ and $R^9$ is hydrogen. In certain embodiments, each instance of $R^7$, $R^8$, and $R^9$ is hydrogen.

As generally defined herein, each occurrence of $R^{D1}$, $R^{D2}$, $R^{D3}$, and $R^{D4}$ is independently hydrogen, substituted or unsubstituted $C_{1-3}$ alkyl, —C(=O)$R^{D6}$, —C(=O)$OR^{D5}$, —C(=O)$SR^{D5}$, —C(=O)N($R^{D5}$)$_2$, —S(=O)$_2R^{D6}$, —S(=O)$_2OR^{D5}$, —P(=O)$_2R^{D6}$, —P(=O)$_2OR^{D5}$, —P(=O)($OR^{D5}$)$_2$, —P(=O)($R^{D6}$)$_2$, or —P(=O)($R^{D6}$) ($OR^{D5}$); wherein each occurrence of $R^{D5}$ and $R^{D6}$ is as define herein.

In certain embodiments, at least one of $R^{D1}$, $R^{D2}$, $R^{D3}$, and $R^{D4}$ is hydrogen, e.g., at least one, two, three, or all of $R^{D1}$, $R^{D2}$, $R^{D3}$, and $R^{D4}$ is hydrogen.

In certain embodiments, at least one of (e.g., one, two, three, or all four) $R^{D1}$, $R^{D2}$, $R^{D3}$, and $R^{D4}$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

In certain embodiments, at least one of (e.g., one, two, three, or all four) $R^{D1}$, $R^{D2}$, $R^{D3}$, and $R^{D4}$ is —C(=O)$R^{D6}$, —C(=O)$OR^{D5}$, —C(=O)$SR^{D5}$, or —C(=O)N($R^{D5}$)$_2$, wherein $R^{D5}$ and $R^{D6}$ are as defined herein.

In certain embodiments, at least one of (e.g., one, two, three, or all four) $R^{D1}$, $R^{D2}$, $R^{D3}$, and $R^{D4}$ is —C(=O)$R^{D6}$, e.g., for example, wherein $R^{D6}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, at least one of (e.g., one, two, three, or all four) $R^{D1}$, $R^{D2}$, $R^{D3}$, and $R^{D4}$ is —C(=O)$CH_3$.

In certain embodiments, at least one of (e.g., one, two, three, or all four) $R^{D1}$, $R^{D2}$, $R^{D3}$, and $R^{D4}$ is —C(=O)$OR^{D5}$, e.g., for example, wherein $R^{D5}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, at least one of (e.g., one, two, three, or all four) $R^{D1}$, $R^{D2}$, $R^{D3}$, and $R^{D4}$ is —C(=O)$OCH_3$.

In certain embodiments, at least one of (e.g., one, two, three, or all four) $R^{D1}$, $R^{D2}$, $R^{D3}$, and $R^{D4}$ is —C(=O)$SR^{D5}$, e.g., for example, wherein $R^{D5}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, at least one of (e.g., one, two, three, or all four) $R^{D1}$, $R^{D2}$, $R^{D3}$, and $R^{D4}$ is —C(=O)$SCH_3$.

In certain embodiments, at least one of (e.g., one, two, three, or all four) $R^{D1}$, $R^{D2}$, $R^{D3}$, and $R^{D4}$ is —C(=O)N ($R^{D5}$)$_2$, e.g., —C(=O)$NH_2$ or —C(=O)$NHR^{D5}$, wherein $R^{D5}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$), or at least one of (e.g., one, two, three, or all four) $R^{D1}$, $R^{D2}$, $R^{D3}$, and $R^{D4}$ is —C(=O)N($R^{D5}$)$_2$ wherein the two $R^{D5}$ groups are joined to form a substituted or unsubstituted heterocyclic or heteroaryl ring.

In certain embodiments, at least one of (e.g., one, two, three, or all four) $R^{D1}$, $R^{D2}$, $R^{D3}$, and $R^{D4}$ is —S(=O)$_2R^{D6}$ or —S(=O)$_2OR^{D5}$, wherein $R^{D6}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{D5}$ is hydrogen or any of the aforementioned groups. In certain embodiments, at least one of (e.g., one, two, three, or all four) $R^{D1}$, $R^{D2}$, $R^{D3}$, and $R^{D4}$ is —S(=O)$_2$R$^{D6}$. In certain embodiments, at least one of (e.g., one, two, three, or all four) $R^{D1}$, $R^{D2}$, $R^{D3}$, and $R^{D4}$ is —S(=O)$_2$OR$^{D5}$, e.g., —SO$_3$H.

In certain embodiments, at least one of (e.g., one, two, three, or all four) $R^{D1}$, $R^{D2}$, $R^{D3}$, and $R^{D4}$ is —P(=O)$_2$R$^{D6}$, —P(=O)$_2$OR$^{D5}$, —P(=O)(OR$^{D5}$)$_2$, —P(=O)(R$^{D6}$)$_2$, or —P(=O)(R$^{D6}$)(OR$^{D5}$), wherein $R^{D6}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{D5}$ is hydrogen or any of the aforementioned groups. In certain embodiments, at least one of (e.g., one, two, three, or all four) $R^{D1}$, $R^{D2}$, $R^{D3}$, and $R^{D4}$—P(=O)$_2$R$^{D2}$. In certain embodiments, at least one of $R^{D1}$, $R^{D2}$, $R^{D3}$, and $R^{D4}$—P(=O)$_2$OR$^{D1}$. In certain embodiments, at least one of (e.g., one, two, three, or all four) $R^{D1}$, $R^{D2}$, $R^{D3}$, and $R^{D4}$—P(=O)(OR$^{D1}$)$_2$. In certain embodiments, at least one of (e.g., one, two, three, or all four) $R^{D1}$, $R^{D2}$, $R^{D3}$, and $R^{D4}$—P(=O)(R$^{D2}$)$_2$. In certain embodiments, at least one of (e.g., one, two, three, or all four) $R^{D1}$, $R^{D2}$, $R^{D3}$, and $R^{D4}$—P(=O)(R$^{D2}$)(OR$^{D1}$).

In certain embodiments, each of $R^{D1}$, $R^{D2}$, $R^{D3}$, and $R^{D4}$ are the same group, e.g., hydrogen or C(=O)CH$_3$. In certain embodiments, however, at least one (e.g., one, two, three, or all four) of $R^{D1}$, $R^{D2}$, $R^{D3}$, and $R^{D4}$ is a different group.

As generally defined herein, $R^{10}$ is a group of formula:

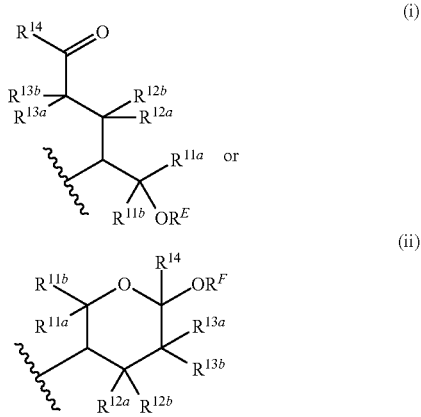

wherein:
each instance of $R^{11a}$, $R^{11b}$, $R^{12a}$, $R^{12b}$, $R^{13a}$, and $R^{13b}$ is independently hydrogen, substituted or unsubstituted $C_{1-3}$ alkyl, or halogen; and $R^{14}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, $R^{10}$ is a group of formula (I). In certain embodiments, $R^{10}$ is a group of formula (ii).

In certain embodiments of formula (i) or (ii), at least one instance of $R^{11a}$, $R^{11b}$, $R^{12a}$, $R^{12b}$, $R^{13a}$, and $R^{13b}$ is hydrogen. In certain embodiments of formula (i) or (ii), at least two instances of $R^{11a}$, $R^{11b}$, $R^{12a}$, $R^{12b}$, $R^{13a}$, and $R^{13b}$ is hydrogen. In certain embodiments of formula (i) or (ii), at least three instances of $R^{11a}$, $R^{11b}$, $R^{12a}$, $R^{12b}$, $R^{13a}$, and $R^{13b}$ is hydrogen. In certain embodiments of formula (i) or (ii), at least four instances of $R^{11a}$, $R^{11b}$, $R^{12a}$, $R^{12b}$, $R^{13a}$, and $R^{13b}$ is hydrogen. In certain embodiments of formula (i) or (ii), at least five instances of $R^{11a}$, $R^{11b}$, $R^{12a}$, $R^{12b}$, $R^{13a}$, and $R^{13b}$ is hydrogen. In certain embodiments of formula (i) or (ii), each instance of $R^{11a}$, $R^{11b}$, $R^{12a}$, $R^{12b}$, $R^{13a}$, and $R^{13b}$ is hydrogen.

As generally defined herein, $R^{11a}$ is hydrogen, substituted or unsubstituted $C_{1-3}$ alkyl, or halogen. In certain embodiments, $R^{11a}$ is hydrogen. In certain embodiments, $R^{11a}$ is halogen, e.g., fluoro, chloro, bromo, or iodo. In certain embodiments, $R^{11a}$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

As generally defined herein, $R^{11b}$ is hydrogen, substituted or unsubstituted $C_{1-3}$ alkyl, or halogen. In certain embodiments, $R^{11b}$ is hydrogen. In certain embodiments, $R^{11b}$ is halogen, e.g., fluoro, chloro, bromo, or iodo. In certain embodiments, $R^{11b}$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

As generally defined herein, $R^{12a}$ is hydrogen, substituted or unsubstituted $C_{1-3}$ alkyl, or halogen. In certain embodiments, $R^{12a}$ is hydrogen. In certain embodiments, $R^{12a}$ is halogen, e.g., fluoro, chloro, bromo, or iodo. In certain embodiments, $R^{12a}$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

As generally defined herein, $R^{12b}$ is hydrogen, substituted or unsubstituted $C_{1-3}$ alkyl, or halogen. In certain embodiments, $R^{12b}$ is hydrogen. In certain embodiments, $R^{12b}$ is halogen, e.g., fluoro, chloro, bromo, or iodo. In certain embodiments, $R^{12b}$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

As generally defined herein, $R^{13a}$ is hydrogen, substituted or unsubstituted $C_{1-3}$ alkyl, or halogen. In certain embodiments, $R^{13a}$ is hydrogen. In certain embodiments, $R^{13a}$ is halogen, e.g., fluoro, chloro, bromo, or iodo. In certain embodiments, $R^{13a}$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

As generally defined herein, $R^{13b}$ is hydrogen, substituted or unsubstituted $C_{1-3}$ alkyl, or halogen. In certain embodiments, $R^{13b}$ is hydrogen. In certain embodiments, $R^{13b}$ is halogen, e.g., fluoro, chloro, bromo, or iodo. In certain embodiments, $R^{13b}$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

As generally defined herein, $R^{14}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, $R^{14}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^{14}C_{1-6}$alkyl groups include, but are not limited to, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), and substituted or unsubstituted n-hexyl ($C_6$). In certain embodiments, $R^{14}$ is unsubstituted methyl, i.e., —$CH_3$.

In certain embodiments, $R^{14}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, $R^{14}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl.

In certain embodiments, $R^{14}$ is substituted or unsubstituted carbocyclyl, e.g., substituted or unsubstituted $C_{3-6}$carbocyclyl, substituted or unsubstituted $C_{3-4}$-carbocyclyl, substituted or unsubstituted $C_{4-5}$ carbocyclyl, or substituted or unsubstituted $C_{5-6}$ carbocyclyl.

In certain embodiments, $R^{14}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, $R^{14}$ is substituted or unsubstituted aryl, e.g., substituted or unsubstituted phenyl.

In certain embodiments, $R^{14}$ is substituted or unsubstituted heteroaryl, e.g., substituted or unsubstituted 5- to 6-membered heteroaryl.

As generally defined herein, $R^E$ is hydrogen, substituted or unsubstituted $C_{1-3}$ alkyl, —C(=O)$R^{E2}$, —C(=O)O$R^{E1}$, —C(=O)S$R^{E1}$, —C(=O)N($R^{E1}$)$_2$, —S(=O)$_2R^{E2}$, —S(=O)$_2$O$R^{E1}$, —P(=O)$_2R^{E2}$, —P(=O)$_2$O$R^{E1}$, —P(=O)(O$R^{E1}$)$_2$, —P(=O)($R^{E2}$)$_2$, or —P(=O)($R^{E2}$)(O$R^{E1}$), wherein each occurrence of $R^{E1}$ and $R^{E2}$ is as define herein.

In certain embodiments, $R^E$ is hydrogen.

In certain embodiments, $R^E$ is substituted or unsubstituted $C_{1-3}$ alkyl, e.g., substituted or unsubstituted $C_{1-2}$alkyl, substituted or unsubstituted $C_{2-3}$alkyl, substituted or unsubstituted $C_1$ alkyl, substituted or unsubstituted $C_2$ alkyl, or substituted or unsubstituted $C_3$ alkyl. Exemplary $C_{1-3}$alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

In certain embodiments, $R^E$ is —C(=O)$R^{E2}$, —C(=O)O$R^{E1}$, —C(=O)S$R^{E1}$, or —C(=O)N($R^{E1}$)$_2$, wherein $R^{E1}$ and $R^{E2}$ are as defined herein.

In certain embodiments, $R^E$ is —C(=O)$R^{E2}$, e.g., for example, wherein $R^{E2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^E$ is —C(=O)$CH_3$.

In certain embodiments, $R^E$ is —C(=O)O$R^{E1}$, e.g., for example, wherein $R^{E1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^E$ is —C(=O)O$CH_3$.

In certain embodiments, $R^E$ is —C(=O)S$R^{E1}$, e.g., for example, wherein $R^{E1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^E$ is —C(=O)SCH$_3$.

In certain embodiments, $R^E$ is —C(=O)N($R^{E1}$)$_2$, e.g., —C(=O)NH$_2$ or —C(=O)NHR$^{E1}$, wherein $R^{E1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$), or $R^E$ is —C(=O)N($R^{E1}$)$_2$ wherein the two $R^{E1}$ groups are joined to form a substituted or unsubstituted heterocyclic or heteroaryl ring.

In certain embodiments, $R^E$ is —S(=O)$_2$R$^{E2}$ or —S(=O)$_2$OR$^{E1}$, wherein $R^{E2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{E1}$ is hydrogen or any of the aforementioned groups. In certain embodiments, $R^E$ is —S(=O)$_2$R$^{E2}$. In certain embodiments, $R^E$ is —S(=O)$_2$OR$^{E1}$, e.g., —SO$_3$H.

In certain embodiments, $R^E$ is —P(=O)$_2$R$^{E2}$, —P(=O)$_2$OR$^{E1}$, —P(=O)(OR$^{E1}$)$_2$, —P(=O)(R$^{E2}$)$_2$, or —P(=O)(R$^{E2}$)(OR$^{E1}$), wherein $R^{E2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$), or substituted or unsubstituted phenyl, and $R^{E1}$ is hydrogen or any of the aforementioned groups. In certain embodiments, $R^E$ is —P(=O)$_2$R$^{E2}$. In certain embodiments, $R^E$ is —P(=O)$_2$OR$^{E1}$. In certain embodiments, $R^E$ is —P(=O)(OR$^{E1}$)$_2$. In certain embodiments, $R^E$ is —P(=O)(R$^{E2}$)$_2$. In certain embodiments, $R^E$ is —P(=O)(R$^{E2}$)(OR$^{E1}$).

In certain embodiments, $R^E$ and $R^{D1}$, $R^{D2}$, $R^{D3}$, and $R^{D4}$ are the same group, e.g., each are hydrogen or —C(=O)CH$_3$. In certain embodiments, however, $R^E$ is different from $R^{D1}$, $R^{D2}$, $R^{D3}$, and $R^{D4}$, e.g., $R^E$ is —C(=O)CH$_3$ and each of $R^{D1}$, $R^{D2}$, $R^{D3}$, and $R^{D4}$ are hydrogen.

As generally defined herein, $R^F$ is hydrogen, substituted or unsubstituted $C_{1-3}$ alkyl, —C(=O)R$^{F2}$, —C(=O)OR$^{F1}$, —C(=O)SR$^{F1}$, —C(=O)N(R$^{F1}$)$_2$, —S(=O)$_2$R$^{F2}$, —S(=O)$_2$OR$^{F1}$, —P(=O)$_2$R$^{F2}$, —P(=O)$_2$OR$^{F1}$, —P(=O)(OR$^{F1}$)$_2$, —P(=O)(R$^{F2}$)$_2$, or —P(=O)(R$^{F2}$)(OR$^{F1}$), wherein each occurrence of $R^{F1}$ and $R^{F2}$ is as define herein.

In certain embodiments, $R^F$ is hydrogen.

In certain embodiments, $R^F$ is substituted or unsubstituted $C_{1-3}$ alkyl, e.g., substituted or unsubstituted $C_{1-2}$ alkyl, substituted or unsubstituted $C_{2-3}$ alkyl, substituted or unsubstituted $C_1$ alkyl, substituted or unsubstituted $C_2$ alkyl, or substituted or unsubstituted $C_3$ alkyl. Exemplary $C_{1-3}$ alkyl groups include, but are not limited to, substituted or unsubstituted methyl ($C_1$), substituted or unsubstituted ethyl ($C_2$), substituted or unsubstituted n-propyl ($C_3$), and substituted or unsubstituted isopropyl ($C_3$).

In certain embodiments, $R^F$ is —C(=O)R$^{F2}$, —C(=O)OR$^{F1}$, —C(=O)SR$^{F1}$, or —C(=O)N(R$^{F1}$)$_2$, wherein $R^{F1}$ and $R^{F2}$ are as defined herein.

In certain embodiments, $R^F$ is —C(=O)R$^{F2}$, e.g., for example, wherein $R^{F2}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^F$ is —C(=O)CH$_3$.

In certain embodiments, $R^F$ is —C(=O)OR$^{F1}$, e.g., for example, wherein $R^{F1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^F$ is —C(=O)OCH$_3$.

In certain embodiments, $R^F$ is —C(=O)SR$^{F1}$, e.g., for example, wherein $R^{F1}$ is, for example, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$). In certain embodiments, $R^F$ is —C(=O)SCH$_3$.

In certain embodiments, $R^F$ is —C(=O)N($R^{F1}$)$_2$, e.g., —C(=O)NH$_2$ or —C(=O)NHR$^{F1}$, wherein $R^{F1}$ is, for example, substituted or unsubstituted methyl (C$_1$), substituted or unsubstituted ethyl (C$_2$), substituted or unsubstituted n-propyl (C$_3$), substituted or unsubstituted isopropyl (C$_3$), substituted or unsubstituted n-butyl (C$_4$), substituted or unsubstituted tert-butyl (C$_4$), substituted or unsubstituted sec-butyl (C$_4$), substituted or unsubstituted iso-butyl (C$_4$), substituted or unsubstituted n-pentyl (C$_5$), substituted or unsubstituted 3-pentanyl (C$_5$), substituted or unsubstituted amyl (C$_5$), substituted or unsubstituted neopentyl (C$_5$), substituted or unsubstituted 3-methyl-2-butanyl (C$_5$), substituted or unsubstituted tertiary amyl (C$_5$), or substituted or unsubstituted n-hexyl (C$_6$), or $R^F$ is —C(=O)N($R^{F1}$)$_2$ wherein the two $R^{F1}$ groups are joined to form a substituted or unsubstituted heterocyclic or heteroaryl ring.

In certain embodiments, $R^F$ is —S(=O)$_2$R$^{F2}$ or —S(=O)$_2$OR$^{F1}$, wherein $R^{F2}$ is, for example, substituted or unsubstituted methyl (C$_1$), substituted or unsubstituted ethyl (C$_2$), substituted or unsubstituted n-propyl (C$_3$), substituted or unsubstituted isopropyl (C$_3$), substituted or unsubstituted n-butyl (C$_4$), substituted or unsubstituted tert-butyl (C$_4$), substituted or unsubstituted sec-butyl (C$_4$), substituted or unsubstituted iso-butyl (C$_4$), substituted or unsubstituted n-pentyl (C$_5$), substituted or unsubstituted 3-pentanyl (C$_5$), substituted or unsubstituted amyl (C$_5$), substituted or unsubstituted neopentyl (C$_5$), substituted or unsubstituted 3-methyl-2-butanyl (C$_5$), substituted or unsubstituted tertiary amyl (C$_5$), substituted or unsubstituted n-hexyl (C$_6$), or substituted or unsubstituted phenyl, and $R^{F1}$ is hydrogen or any of the aforementioned groups. In certain embodiments, $R^F$ is —S(=O)$_2$R$^{F2}$. In certain embodiments, $R^F$ is —S(=O)$_2$OR$^{F1}$, e.g., —SO$_3$H.

In certain embodiments, $R^F$ is —P(=O)$_2$R$^{F2}$, —P(=O)$_2$OR$^{F1}$, —P(=O)(OR$^{F1}$)$_2$, —P(=O)(R$^{F2}$)$_2$, or —P(=O)(R$^{F2}$)(OR$^{F1}$), wherein $R^{F2}$ is, for example, substituted or unsubstituted methyl (C$_1$), substituted or unsubstituted ethyl (C$_2$), substituted or unsubstituted n-propyl (C$_3$), substituted or unsubstituted isopropyl (C$_3$), substituted or unsubstituted n-butyl (C$_4$), substituted or unsubstituted tert-butyl (C$_4$), substituted or unsubstituted sec-butyl (C$_4$), substituted or unsubstituted iso-butyl (C$_4$), substituted or unsubstituted n-pentyl (C$_5$), substituted or unsubstituted 3-pentanyl (C$_5$), substituted or unsubstituted amyl (C$_5$), substituted or unsubstituted neopentyl (C$_5$), substituted or unsubstituted 3-methyl-2-butanyl (C$_5$), substituted or unsubstituted tertiary amyl (C$_5$), substituted or unsubstituted n-hexyl (C$_6$), or substituted or unsubstituted phenyl, and $R^{F1}$ is hydrogen or any of the aforementioned groups. In certain embodiments, $R^F$ is —P(=O)$_2$R$^{F2}$. In certain embodiments, $R^F$ is —P(=O)$_2$OR$^{F1}$. In certain embodiments, $R^F$ is —P(=O)(OR$^{F1}$)$_2$. In certain embodiments, $R^F$ is —P(=O)(R$^{F2}$)$_2$. In certain embodiments, $R^F$ is —P(=O)(R$^{F2}$)(OR$^{F1}$).

In certain embodiments, $R^F$ and $R^{D1}$, $R^{D2}$, $R^{D3}$, and $R^{D4}$ are the same group, e.g., each are hydrogen or —C(=O)CH$_3$. In certain embodiments, however, $R^F$ is different from $R^{D1}$, $R^{D2}$, $R^{D3}$, and $R^{D4}$, e.g., $R^F$ is —C(=O)CH$_3$ and each of $R^{D1}$, $R^{D2}$, $R^{D3}$, and $R^{D4}$ are hydrogen.

Various combinations of the above embodiments are contemplated. For example, in certain embodiments, wherein $R^8$ is a group of formula (i), provided are compounds of Formula (IV-a-i):

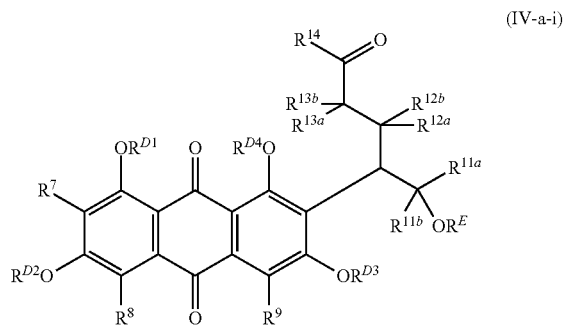

and pharmaceutically acceptable salts thereof. In certain embodiments, $R^{D1}$ is hydrogen or —C(=O)R$^{D6}$. In certain embodiments, $R^{D2}$ is hydrogen or —C(=O)R$^{D6}$. In certain embodiments, $R^{D3}$ is hydrogen or —C(=O)R$^{D6}$. In certain embodiments, $R^{D4}$ is hydrogen or —C(=O)R$^{D6}$. In certain embodiments, $R^7$ is hydrogen. In certain embodiments, $R^8$ is hydrogen. In certain embodiments, $R^9$ is hydrogen. In certain embodiments, $R^E$ is hydrogen or —C(=O)R$^{E2}$. In certain embodiments, each of $R^{11a}$, $R^{11b}$, $R^{12a}$, $R^{12b}$, $R^{13a}$, and $R^{13b}$ are hydrogen. In certain embodiments, $R^{14}$ is substituted or unsubstituted alkyl, e.g., —CH$_3$.

In certain embodiments, wherein $R^8$ is a group of formula (i), and $R^7$, $R^8$, and $R^9$ are hydrogen, provided are compounds of Formula (IV-b-i):

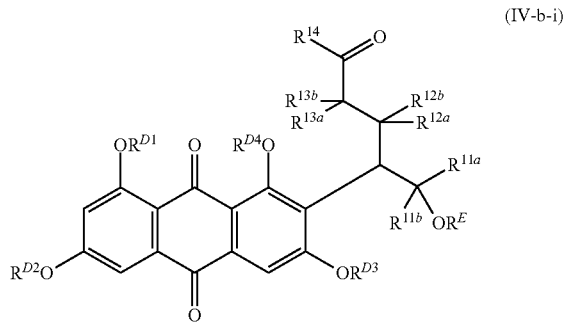

and pharmaceutically acceptable salts thereof. In certain embodiments, $R^{D1}$ is hydrogen or —C(=O)R$^{D6}$. In certain embodiments, $R^{D2}$ is hydrogen or —C(=O)R$^{D6}$. In certain embodiments, $R^{D3}$ is hydrogen or —C(=O)R$^{D6}$. In certain embodiments, $R^{D4}$ is hydrogen or —C(=O)R$^{D6}$. In certain embodiments, $R^E$ is hydrogen or —C(=O)R$^{E2}$. In certain embodiments, each of $R^{11a}$, $R^{11b}$, $R^{12a}$, $R^{12b}$, $R^{13a}$, and $R^{13b}$ are hydrogen. In certain embodiments, $R^{14}$ is substituted or unsubstituted alkyl, e.g., —CH$_3$.

In certain embodiments, wherein $R^8$ is a group of formula (i), and $R^7$, $R^8$, $R^9$, $R^{11a}$, $R^{11b}$, $R^{12a}$, $R^{12b}$, $R^{13a}$, $R^{13b}$ are hydrogen, provided are compounds of Formula (IV-c-i):

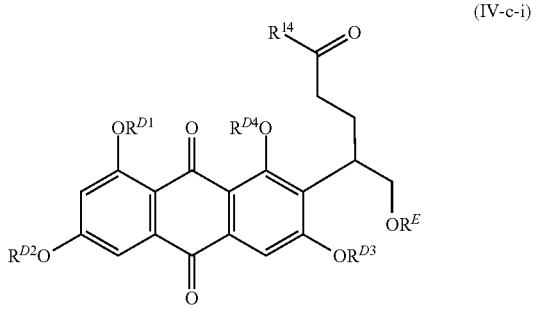

(IV-c-i)

and pharmaceutically acceptable salts thereof. In certain embodiments, $R^{D1}$ is hydrogen or —C(=O)$R^{D6}$. In certain embodiments, $R^{D2}$ is hydrogen or —C(=O)$R^{D6}$. In certain embodiments, $R^{D3}$ is hydrogen or —C(=O)$R^{D6}$. In certain embodiments, $R^{D4}$ is hydrogen or —C(=O)$R^{D6}$. In certain embodiments, $R^E$ is hydrogen or —C(=O)$R^{E2}$. In certain embodiments, $R^{14}$ is substituted or unsubstituted alkyl, e.g., —CH$_3$.

In certain embodiments, wherein $R^8$ is a group of formula (I), and $R^7$, $R^8$, $R^9$, $R^{11a}$, $R^{11b}$, $R^{12a}$, $R^{12b}$, $R^{13a}$, and $R^{13b}$ are hydrogen, and $R^{14}$ is —CH$_3$, provided are compounds of Formula (IV-d-i):

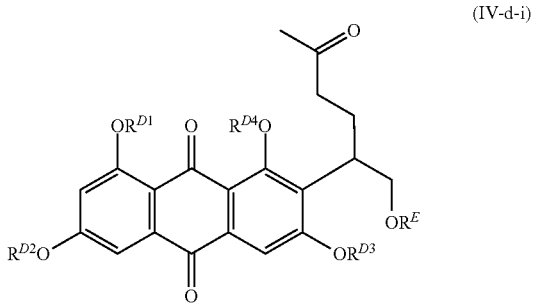

(IV-d-i)

and pharmaceutically acceptable salts thereof. In certain embodiments, $R^{D1}$ is hydrogen or —C(=O)$R^{D6}$. In certain embodiments, $R^{D2}$ is hydrogen or —C(=O)$R^{D6}$. In certain embodiments, $R^{D3}$ is hydrogen or —C(=O)$R^{D6}$. In certain embodiments, $R^{D4}$ is hydrogen or —C(=O)$R^{D6}$. In certain embodiments, $R^E$ is hydrogen or —C(=O)$R^{E2}$.

In certain embodiments, wherein $R^8$ is a group of formula (II), provided are compounds of Formula (IV-a-ii):

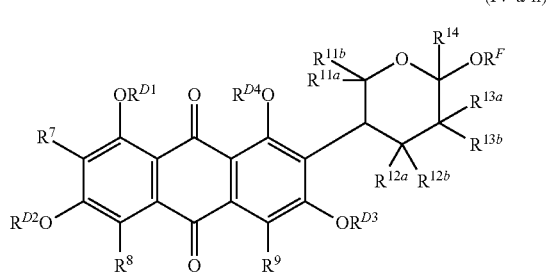

(IV-a-ii)

and pharmaceutically acceptable salts thereof. In certain embodiments, $R^{D1}$ is hydrogen or —C(=O)$R^{D6}$. In certain embodiments, $R^{D2}$ is hydrogen or —C(=O)$R^{D6}$. In certain embodiments, $R^{D3}$ is hydrogen or —C(=O)$R^{D6}$. In certain embodiments, $R^{D4}$ is hydrogen or —C(=O)$R^{D6}$. In certain embodiments, $R^7$ is hydrogen. In certain embodiments, $R^8$ is hydrogen. In certain embodiments, $R^F$ is hydrogen or —C(=O)$R^{F2}$. In certain embodiments, each of $R^{11a}$, $R^{11b}$, $R^{12a}$, $R^{12b}$, $R^{13a}$, and $R^{13b}$ are hydrogen. In certain embodiments, $R^{14}$ is substituted or unsubstituted alkyl, e.g., —CH$_3$.

In certain embodiments, wherein $R^8$ is a group of formula (ii), and $R^7$, $R^8$, and $R^9$ are hydrogen, provided are compounds of Formula (IV-b-ii):

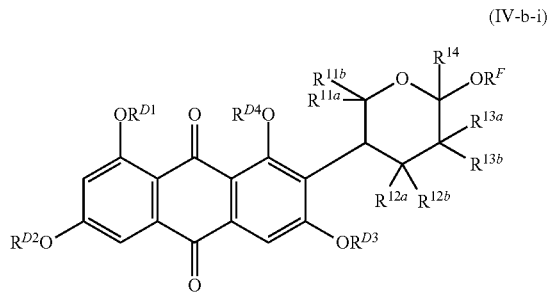

(IV-b-i)

and pharmaceutically acceptable salts thereof. In certain embodiments, $R^{D1}$ is hydrogen or —C(=O)$R^{D6}$. In certain embodiments, $R^{D2}$ is hydrogen or —C(=O)$R^{D6}$. In certain embodiments, $R^{D3}$ is hydrogen or —C(=O)$R^{D6}$. In certain embodiments, $R^{D4}$ is hydrogen or —C(=O)$R^{D6}$. In certain embodiments, $R^F$ is hydrogen or —C(=O)$R^{F2}$. In certain embodiments, each of $R^{11a}$, $R^{11b}$, $R^{12a}$, $R^{12b}$, $R^{13a}$, and $R^{13b}$ are hydrogen. In certain embodiments, $R^{14}$ is substituted or unsubstituted alkyl, e.g., —CH$_3$.

In certain embodiments, wherein $R^8$ is a group of formula (ii), and $R^7$, $R^8$, $R^9$, $R^{11a}$, $R^{11b}$, $R^{12a}$, $R^{12b}$, $R^{13a}$, and $R^{13b}$ are hydrogen, provided are compounds of Formula (IV-c-ii):

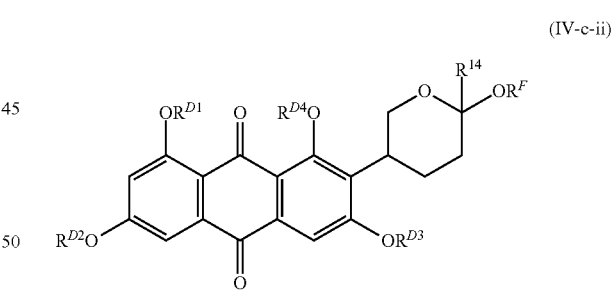

(IV-c-ii)

and pharmaceutically acceptable salts thereof. In certain embodiments, $R^{D1}$ is hydrogen or —C(=O)$R^{D6}$. In certain embodiments, $R^{D2}$ is hydrogen or —C(=O)$R^{D6}$. In certain embodiments, $R^{D3}$ is hydrogen or —C(=O)$R^{D6}$. In certain embodiments, $R^{D4}$ is hydrogen or —C(=O)$R^{D6}$. In certain embodiments, $R^F$ is hydrogen or —C(=O)$R^{F2}$. In certain embodiments, $R^{14}$ is substituted or unsubstituted alkyl, e.g., —CH$_3$.

In certain embodiments, wherein $R^8$ is a group of formula (ii), and $R^7$, $R^8$, $R^9$, $R^{11a}$, $R^{11b}$, $R^{12a}$, $R^{12b}$, $R^{13a}$, and $R^{13b}$ are hydrogen, and $R^{14}$ is —CH$_3$, provided are compounds of Formula (IV-d-ii):

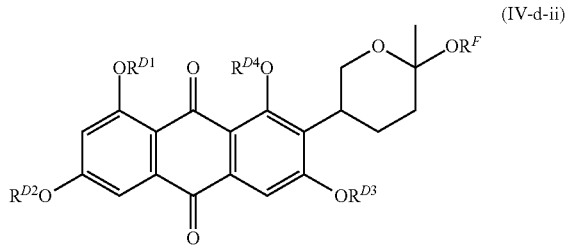

(IV-d-ii)

and pharmaceutically acceptable salts thereof. In certain embodiments, $R^{D1}$ is hydrogen or $—C(=O)R^{D6}$. In certain embodiments, $R^{D2}$ is hydrogen or $—C(=O)R^{D6}$. In certain embodiments, $R^{D3}$ is hydrogen or $—C(=O)R^{D6}$. In certain embodiments, $R^{D4}$ is hydrogen or $—C(=O)R^{D6}$. In certain embodiments, $R^F$ is hydrogen or $—C(=O)R^{F2}$.

In certain embodiments, the compound of Formula (IV) is the pure and isolated compound of formula:

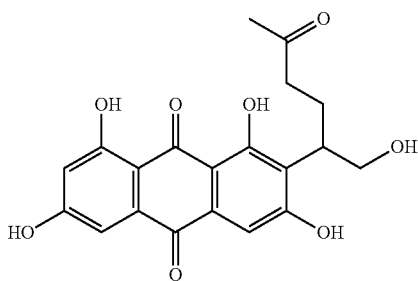 [SMILES: CC(=O)CCC(CO)c1c(O)cc2c(c1O)C(=O)c1c(O)cc(O)cc1C2=O]

or a pharmaceutically acceptable salt thereof. In certain embodiments, prodrugs of the above compound are contemplated.

In certain embodiments, the compound of Formula (IV) is the pure and isolated compound of formula:

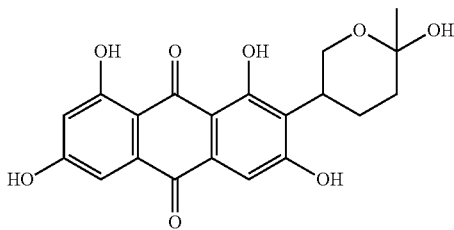 [SMILES: CC1(O)CCC(c2c(O)cc3c(c2O)C(=O)c2c(O)cc(O)cc2C3=O)CO1]

or a pharmaceutically acceptable salt thereof. In certain embodiments, prodrugs of the above compound are contemplated.

Pharmaceutical Compositions

Further provided are pharmaceutical compositions comprising a compound of Formula (I), (II), (III), or (IV), or a pharmaceutically acceptable salt thereof (the "active ingredient"), and a pharmaceutically acceptable excipient. In certain embodiments, the active ingredient is provided in an effective amount in the pharmaceutical composition.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by appropriate method known in the art of pharmacology. In general, such preparatory methods include the steps of bringing the active ingredient into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition will vary, depending upon the identity, size, and/or condition of the subject treated and further depending upon the route by which the pharmaceutical composition is to be administered. By way of example, the pharmaceutical composition may comprise between 0.1% and 100% (w/w) active ingredient.

Exemplary pharmaceutically acceptable excipients include, but are not limited to, inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the active ingredient, it is often desirable to slow the absorption of the active ingredient from subcutaneous or intramuscular injection. This can be accomplished by the use of a liquid suspension of crystalline or amorphous material with poor water solubility. The rate of absorption of the active ingredient then depends upon its rate of dissolution which, in turn, may depend upon crystal size and crystalline form. Alternatively, delayed absorption of a parenterally administered active ingredient may be accomplished by dissolving or suspending the active ingredient in an oil vehicle.

Compositions for rectal or vaginal administration are typically suppositories which can be prepared by mixing the active ingredient with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient only, or preferentially, in a certain part of the intestinal tract, optionally, in a delayed manner.

Dosage forms for topical and/or transdermal administration includes, for example, ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein.

A pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to compositions suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

As described herein, the active ingredient or pharmaceutical composition comprising the active ingredient can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of the active ingredient or pharmaceutical composition comprising the active ingredient required to achieve an effective amount will vary from subject to subject, depending, for example, on species, age, and general condition of a subject, severity of the side effects or disorder, identity of the active ingredient, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of the active ingredient for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg.

In certain embodiments, the active ingredient may be administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that the active ingredient, as described herein, can be administered in combination with one or more additional therapeutically active agents. The additional therapeutically active agents can improve the active ingredient's bioavailability, reduce and/or modify the active ingredient's metabolism, inhibit the active ingredient's excretion, and/or modify the active ingredient's distribution within the body. It will also be appreciated that the therapy employed may achieve a desired effect for the same disorder, and/or it may achieve different effects.

The active ingredient can further be administered concurrently with, prior to, or subsequent to, the administration of one or more additional therapeutically active agents. In general, each agent will be administered at a dose and/or on a time schedule determined for that agent. In will further be appreciated that the additional therapeutically active agent utilized in the combination can be administered together in a single composition or administered separately in different compositions. The particular combination to employ in a regimen will take into account compatibility of the active ingredient with the additional therapeutically active agent and/or the desired therapeutic effect to be achieved. In general, it is expected that additional therapeutically active agents utilized in combination with the active ingredient be utilized at levels that do not exceed the levels at which they are utilized individually. In some embodiments, the levels utilized in combination will be lower than those utilized individually.

Still further encompassed by the invention are kits (e.g., pharmaceutical packs). The kits provided may comprise the active ingredient or pharmaceutical composition thereof, and a container (e.g., a vial, ampule, bottle, syringe, and/or dispenser package, or other suitable container). In some embodiments, the kit may further include a second container comprising a pharmaceutical excipient for dilution or suspension of the pharmaceutical composition or the active ingredient. In some embodiments, the pharmaceutical composition or compound provided in the container and the second container are combined to form one unit dosage form.

Optionally, a single container may comprise one or more compartments for containing a pharmaceutical composition or the active ingredient and/or a pharmaceutically acceptable excipient for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A kit may thus comprise such multi-compartment containers providing a pharmaceutical composition or the active ingredient and one or more pharmaceutically acceptable excipients.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

Methods of Use and Treatment

The present invention also provides methods of using a compound of Formula (I), (II), (III), or (IV), or a pharmaceutically acceptable salt thereof, as described herein.

For example, in one aspect, provided are methods of treating a bacterial infection in a subject, comprising administering an effective amount of a compound of Formula (I), (II), (III), or (IV), or a pharmaceutically acceptable salt thereof.

As used herein, a "bacterial infection" refers to an infection with a bacterium, and the compound of Formula (I), (II), (III), or (IV), or a pharmaceutically acceptable salt thereof exhibits anti-bacterial activity which is sufficient to treat the bacterial infection. In certain embodiments, the compound of Formula (I), (II), (III), or (IV), or a pharmaceutically acceptable salt thereof has a mean inhibitory concentration (MIC), with respect to a particular bacterium, of less than 100 μg/mL, less than 90 μg/mL, less than 80 μg/mL, less than 70 μg/mL, less than 60 μg/mL, less than 50 μg/mL, less than 25 μg/mL, less than 5 μg/mL, and or less than 1 μg/mL.

Bacterial infections include, but are not limited to, infections with a gram positive bacteria (e.g., of the phylum Actinobacteria, phylum Firmicutes, or phylum Tenericutes); gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a gram positive bacteria. In certain embodiments, the gram positive bacteria is a bacteria of the phylum Firmicutes.

In certain embodiments, the bacteria is a member of the phylum Firmicutes and the genus *Enterococcus*; in this case, the bacterial infection is an *Enterococcus* infection. Enterococci bacteria include, but are not limited to, *E. avium, E. durans, E. faecalis, E. faecium, E. gallinarum, E. solitarius, E. casseliflavus*, and *E. raffinosus*. In certain embodiments, the *Enterococcus* infection is an *E. faecalis* infection. In certain embodiments, the *Enterococcus* infection is an *E. faecium* infection.

In certain embodiments, the bacteria is a member of the phylum Firmicutes and the genus *Staphylococcus*; in this case, the bacterial infection is a *Staphylococcus* infection. Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluoroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is an *S. aureus* infection.

In certain embodiments, the bacterial infection is an infection with a gram negative bacteria. In certain embodiments, the gram negative bacteria is a bacteria of the phylum Proteobacteria.

In certain embodiments, the bacteria is a member of the phylum Proteobacteria and the genus *Escherichia*; in this case, the bacterial infection is an *Escherichia* infection, e.g., an *E. coli* infection.

In certain embodiments, the bacteria is a member of the phylum Proteobacteria and the genus *Pseudomonas*; in this case, the bacterial infection is a *Pseudomonas* infection, e.g., a *P. aeruginosa* infection.

In certain embodiments, the bacteria is a member of the phylum Proteobacteria and the genus *Klebsiella*; in this case, the bacterial infection is a *Klebsiella* infection, e.g., a *K. pneumoniae* infection.

In certain embodiments, the bacteria is a member of the phylum Proteobacteria and the genus *Vibrio*; in this case, the bacterial infection is a *Vibrio* infection, e.g., a *V. cholerae* infection.

In certain embodiments, the bacteria is a bacteria of the phylum Acidobacteria. In certain embodiments, the bacteria is a member of the phylum Acidobacteria and the genus *Mycobacterium*; in this case, the bacterial infection is a *Mycobacterium* infection, e.g., an *M. tuberculosis* or an *M. leprae* infection.

In certain embodiments, the bacterial infection is resistant to other antibiotic therapy. For example, in certain embodiments, the bacterial infection is vancomycin resistant (VR). In certain embodiments, the bacterial infection is a vancomycin-resistant *E. faecalis* infection. In certain embodiments, the bacterial infection is a vancomycin-resistant *E. faecium* infection. In certain embodiments, the bacterial infection is a methicillin-resistant (MR). In certain embodiments, the bacterial infection is a methicillin-resistant *S. aureus* (MRSA) infection.

In certain embodiments, the bacterial infection is an *Escherichia coli, Pseudomonas aeruginosa, Vibrio cholerae*, methicillin-resistant *Staphylococcus aureus*, or *Mycobacterium tuberculosis* infection. In certain embodiments, the bacterial infection is a methicillin-resistant *Staphylococcus aureus* or *Mycobacterium tuberculosis* infection. In certain embodiments, the bacterial infection is a methicillin-resistant *Staphylococcus aureus* infection. In certain embodiments, the bacterial infection is a *Mycobacterium tuberculosis* infection.

Screening Method

Also described herein is a sensitive and robust, low-tech and inexpensive high throughput metabolic, whole cell-based screening method for identification of new antibiotics. This screen is based on a colorimetric assay of pH that identifies inhibitors of bacterial sugar (a bacterial sugar that can be fermented by a particular bacterium, e.g., sucrose) fermentation. In one embodiment, the method is a method of identifying an inhibitor of sugar fermentation in a *V. cholerae* strain by monitoring (e.g., by measuring) pH when the *V. cholerae* strain is cultured in the presence of a candidate compound (inhibitor) of sugar fermentation. If a candidate compound inhibits sugar fermentation in the bacterial strain under the conditions used, the candidate compound is considered an "inhibitor of bacterial sugar fermentation," and is further considered an antibiotic.

As described further, the method is a colorimetric assay of pH; the medium in which the strain is cultured in the presence of a candidate compound comprises at least one, e.g., one, two, three, or more, pH indicators. In some embodiments, the pH indicators are bromothymol blue and thymol blue and, as a result, the assay is a three-color assay. Based on the pKa values of bromothymol blue and thymol blue, Applicants predicted that the medium would be yellow at pH<7.1, when both indicators are protonated and green at a pH between 7.1 and 8.0 because bromothymol blue would be blue (due to deprotonation) and thymol blue would remain yellow. At pH>8.0, when both indicators are deprotonated, they anticipated that the medium would be blue. Applicants also hypothesized that the visible differences in the color of the culture medium at low and high pH were the result of a change in absorbance at a wavelength in the visible range. They determined that the maximum difference in absorbance for the conditions described was evident at a wavelength of 615 nm, which is the wavelength at which color determinations are typically carried out in the present method.

Thus, in another aspect, provided is a method of identifying an inhibitor of bacterial sugar fermentation in a bacterial strain, the method comprising:

(a) combining a candidate compound and a bacterial strain in which sugar transport depends on the phosphoenolpyruvate phosphotransferase system, thereby producing a combination;

(b) culturing the combination in media comprising a sugar and one or more pH indicators under conditions appropriate for sugar fermentation by the bacterial strain; and (c) determining if the sugar fermentation occurs in the combination cultured in (b), if sugar fermentation does not occur or is reduced in the combination cultured in (b), relative to the extent to which fermentation occurs under the same conditions except that the candidate compound is not present, the candidate compound is an inhibitor of bacterial sugar fermentation.

Exemplary sugars include, but are not limited to, sucrose, glucose, sorbitol, rhamnose, galactose, mannose, and gluconic acid. In certain embodiments, the sugar is the D-form. In certain embodiments, the sugar is the L-form. In certain embodiments, the sugar is selected from the group consisting of D-sucrose, D-glucose, D-sorbitol, L-rhamnose, D-galactose, D-mannose, and D-gluconic acid. In certain embodiments, the sugar is sucrose, e.g., D-sucrose.

The candidate compound (inhibitor) can be a component of an extract or other mixture, or a compound that is not a component of a more complex composition.

In certain embodiments, the method comprises at least two pH indicators, e.g., two, three, four, five, six, or more indicators. In certain embodiments, the method comprises only two pH indicators. Exemplary pH indicators which are contemplated useful this method are provided in Table 1.

TABLE 1

Exemplary pH indicators

| Molecular Probe | pH Range | Typical Measurement |
|---|---|---|
| bromothymol blue | See right | Below pH 6.0, yellow Above pH 7.6, blue |
| thymol blue* | See right | Transitions from red to yellow at pH 1.2-2.8 Transitions from yellow to blue at pH 8.0-9.6 |
| SNARF indicators* | 6.0-8.0 | Emission ratio 580/640 nm |
| HPTS (pyranine)* | 7.0-8.0 | Excitation ratio 450/405 nm |
| BCECF* | 6.5-7.5 | Excitation ratio 490/440 nm |
| Fluoresceins and carboxyfluoresceins* | 6.0-7.2 | Excitation ratio 490/450 nm |
| LysoSensor Green DND-189* | 4.5-6.0 | Single emission 520 nm |
| Oregon Green dyes* | 4.2-5.7 | Excitation ratio 510/450 nm or excitation ratio 490/440 nm |
| LysoSensor Yellow/Blue DND-160* | 3.5-6.0 | Emission ratio 450/510 nm |
| pH rodo dye* | | Single emission 585 nm |

*fluorophores

In certain embodiments, the media/medium used in the method comprises one or more pH indicators that are protonated at about a pH<7.1. In certain embodiments, the media/medium used in the method comprises at least one pH indicator is deprotonated at about a pH between 7.1 and 8.0. In certain embodiments, the media/medium used in the method comprises at least one pH indicator is protonated at about a pH between 7.1 and 8.0. In certain embodiments, the media/medium used in the method comprises at least one pH indicator that is deprotonated at about a pH>8.0. In certain embodiments, the media/medium used in the method comprises bromothymol blue and thymol blue as pH indicators.

In certain embodiments, the candidate compound is a compound of Formula (I), (II), (III), or (IV), or a pharmaceutically acceptable salt thereof.

In certain embodiments, the bacterial strain is *Escherichia coli, Pseudomonas aeruginosa, Vibrio cholerae*, methicillin-resistant *Staphylococcus aureus*, or *Mycobacterium tuberculosis*.

Examples

In order that the invention described herein may be more fully understood, the following examples are set forth. It should be understood that these examples are for illustrative purposes only and are not to be construed as limiting this invention in any manner.

Methods

Bacterial Strains and Media

A *V. cholerae* 0139 strain M010 (PW357) was used for screening (Waldor et al., Proc Natl Acad Sci USA (1994) 91: 11388-11392). As a control, we used a *V. cholerae* phosphoenolpyruvate phosphotransferase (PTS) mutant (ΔEI, PW961), which is unable to transport sucrose (Houot et al., J Bacteriol (2008) 190: 311-320). *Mycobacterium tuberculosis* H37Rv (ATCC 27294), *Escherichia coli* (ATCC 25922), carbapenemase-positive *Klebsiella pneumonia* (ATCC BAA-1705), and methicillin-resistant *Staphylococcus aureus* (MRSA, ATCC BAA-976) were used for further evaluation of antibacterial activity.

A minimal medium (MM) supplemented with sucrose (0.5% wt/vol), thymol blue (0.006% wt/vol) and bromothymol blue (0.006% wt/vol) (pH-MM$^{Suc}$) was used for the HTS (Houot et al., J Bacteriol (2008) 190: 311-320). In secondary screens, MM was also supplemented with glucose (0.5% wt/vol), thymol blue (0.006% wt/vol), and bromothymol blue (0.006% wt/vol) (pH-MM$^{Glu}$) or pyruvate (0.5% wt/vol) (MM$^{Pyr}$).

*M. tuberculosis* H37Rv was grown at 37uC in Middlebrook 7H9 liquid medium (Difco) supplemented with albumin (0.5% wt/vol), dextrose (10 mM), glycerol (0.2% vol/vol) and Tween 80 (0.05% vol/vol) (7H9-TW80-ADC).

Fungal Culture

Agar plugs containing the endophytic fungal isolate 1223-D were initially grown at 25° C. on yeast malt agar plates supplemented with streptomycin (30 μg/mL) and chlortetracycline (12 μg/mL). After one week, 3 macerated agar plugs were placed in 75 mL of rich seed media consisting of peptone (5 g/L), dextrose (10 g/L), yeast extract (3 g/L), and malt extract (10 g/L) adjusted to pH 6.2 and cultured at 25° C. with shaking for 6 days. 450 mL of malt extract (0.66% wt/vol) and 10 g HP-20 resin were then added to each flask, and the fungi were cultured under the same conditions for 21 days. The fungal culture was subsequently incubated statically at 25° C. for 5 days and filtered. The HP-20 resin with mycelia was extracted three times with 200 mL of ethanol to yield the crude extract.

Natural Product Library

The natural product library, which was prepared in Costa Rica (collection permits 307-2003-OFAU, R-CM-03-2006, R-CMINBio-06-2006, R-CM-INBio-082-2009, R-CM-IN-Bio-04-2009, R-CM-INBio-088-2009 and R-CM-INBio-094-2010), consisted mainly of pre-fractionated extracts from microbial sources, such as fungal endophytes and marine bacteria, although extracts from other sources such as marine invertebrates, cyanobacteria and lichens were also included. See, e.g., Cao et al., *Org Lett* (2010) 12: 4661-4663. Extracts were suspended in dimethyl sulfoxide (DMSO) at a concentration of ~15 mg/mL. The compound library was stored at 220° C. in dessicated storage containers.

HTS for Antimicrobial Activity

Figure 2:
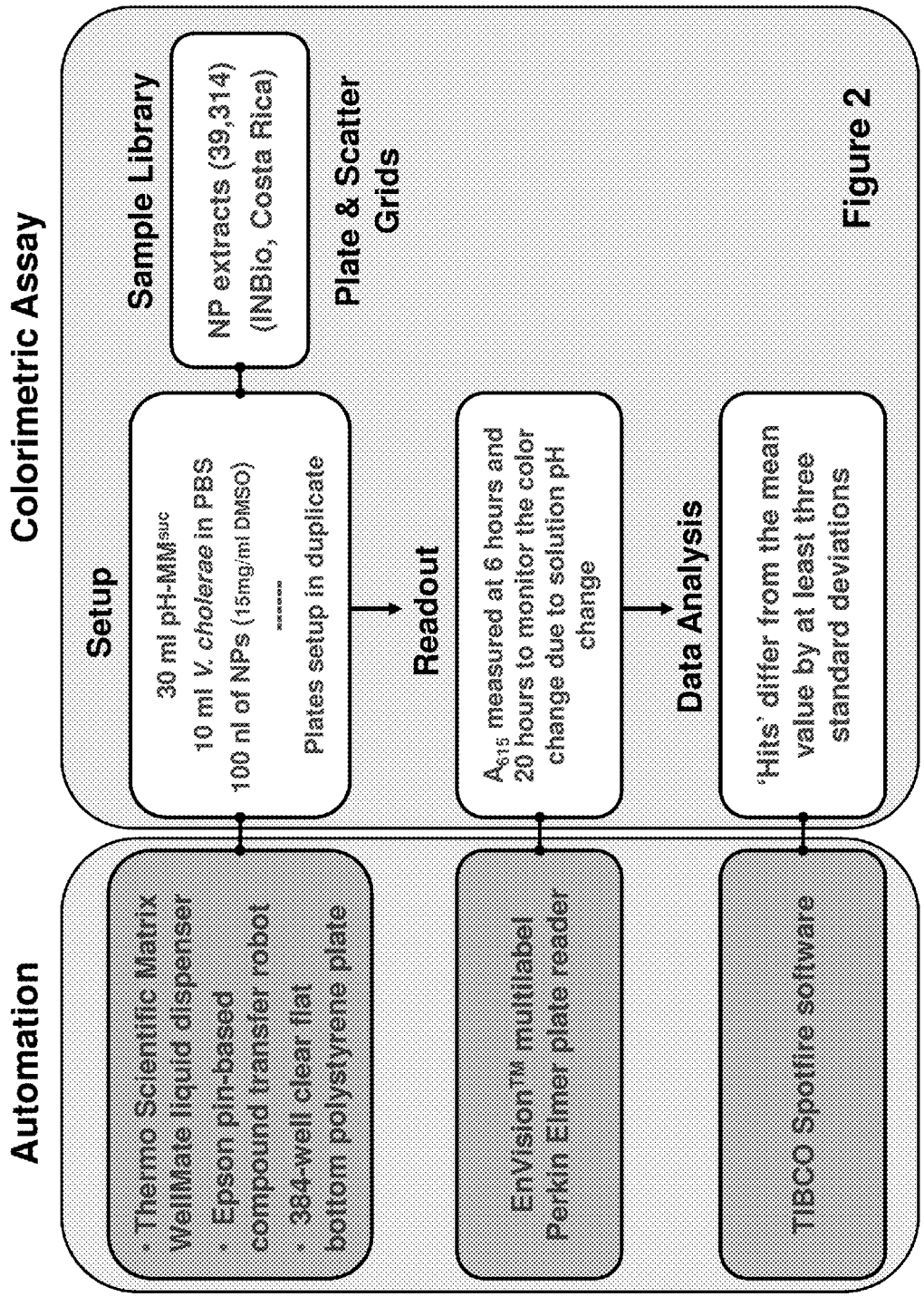
FIG. 2 depicts a flow chart of the high throughput screening (HTS) assay. The HTS assay begins with manual preparation of working solutions of pH-MMSuc and a bacterial suspension with OD600 of 0.015 in PBS. Subsequent steps of the assay are fully automated: solution mixing in the 384 well-plates is performed by a ThermoScientific Matrix WellMate liquid dispenser, pin-transfer of the natural extracts tested is done with a custom-built Epson robot, and A615 readout after incubation at room temperature is accomplished at 6 and 20 hours using an EnVision™ multi-well spectrophotometer. Finally, EnVision™ data were analyzed with Spotfire™ and Excel. Each assay is performed in duplicate. A measurement was considered to be statistically significant if it deviated by at least three standard deviations from the mean measurement calculated using all measurements made with a particular extract library. The calculated Z' factor for the screen was 0.808±0.088.

The first step of compound identification was a high throughput screen (HTS) for inhibitors of *V. cholerae* sucrose fermentation in pH-MM$^{Suc}$ medium. A work-flow chart for this HTS is shown in FIG. 2. Fermentation decreases the pH of the medium. pH indicators in the medium allowed monitoring of medium acidification spectrophotometrically through a change in absorbance at 615 nm ($A_{615}$). To initiate the assay, *V. cholerae* derived from a glycerol stock was streaked on an LB-agar plate and incubated overnight at 37° C. A loopful of cells was harvested, washed three times with PBS, and then resuspended in PBS at an optical density of 0.015. For the HTS, 10 μL of this bacterial cell suspension was aliquoted into the wells of a 384-well plate containing 30 μL of pH-MM$^{Suc}$ and 100 mL of the test compound. For each assay, the $A_{615}$ was measured after incubation at room temperature for 6 and 20 hours. This step was automated and validated in 384-well plate format using an EnVision™ multi-well spectrophotometer.

Compound 1, 2, and 3 Isolation and Identification

Figure 4A:
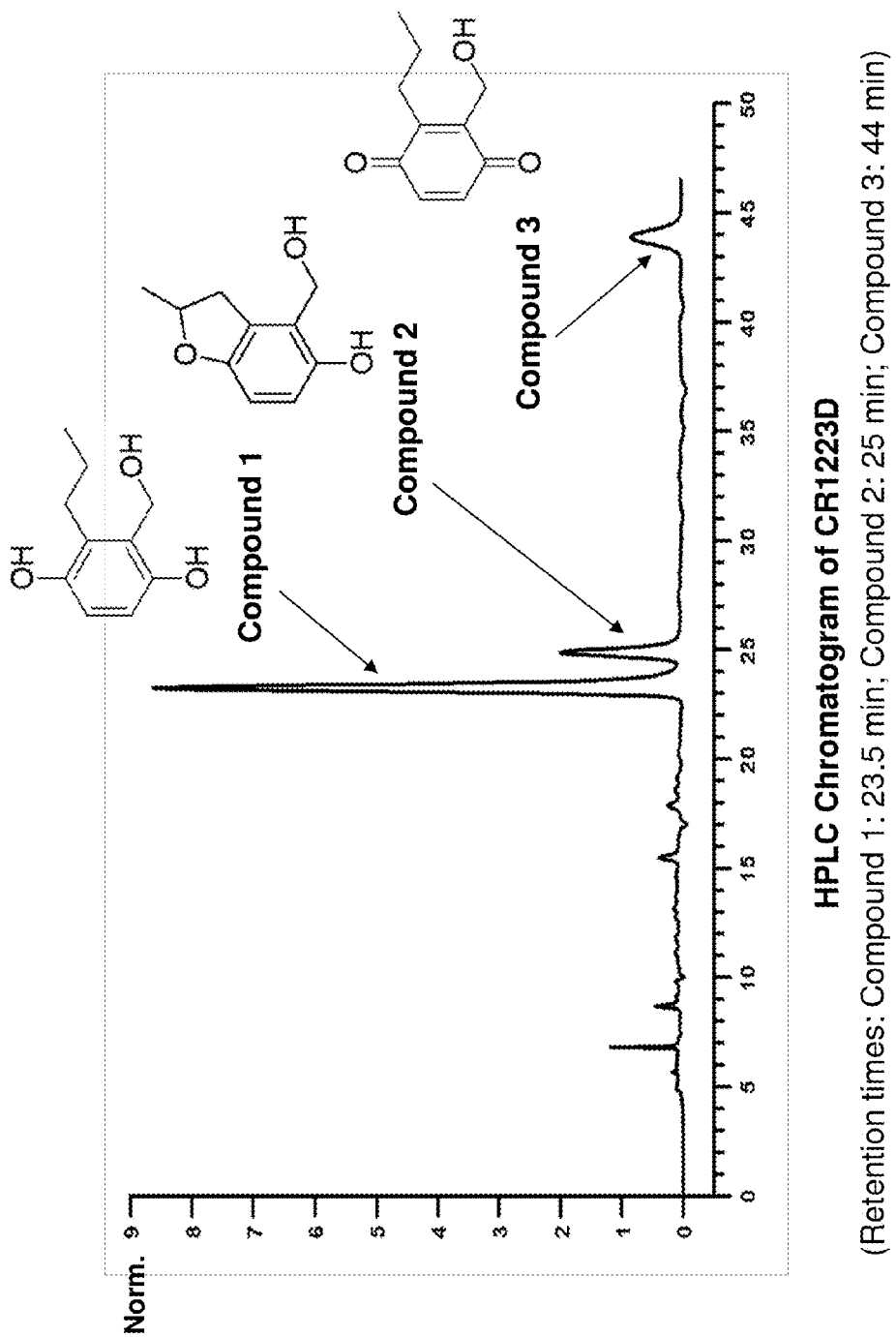
FIGS. 4A-4F depict the chromatogram obtained during fractionation of the extract CR1223-D (FIG. 4A) showing three peaks corresponding to the three compounds isolated (compounds 1, 2, and 3), the chromatogram obtained during fractionation of the extract CR133B (FIG. 4B) showing two peaks corresponding to the two compounds isolated (compounds SC3-22-3 and SC3-22-19), the $^1$H NMR and UV spectra of SC3-22-19 (FIGS. 4C and 4D) and the $^1$H NMR and UV spectra of SC3-22-3 (FIGS. 4E and 4F). Additional characterization data is provided in the Examples.

The crude extract CR1223D was suspended in 90% water/methanol and passed over a C18 SPE column to get fraction I. The column was then washed with methanol to get fraction II. The compound mixture in fraction II was separated on an Agilent 1100 series HPLC with a preparative Phenyl-hexyl column (Phenomenex, Luna, 25 cm×10 mm, 5 μm particle size) using an elution buffer containing 20% acetonitrile/water with 0.1% formic acid at a flow rate of 2 mL/min for 50 minutes. This yielded compound 1 (tR: 23.5 min), compound 2 ($t_R$: 25 min), and compound 3 ($t_R$: 44 min). See FIG. 4A. Spectra for compound identification were obtained on an Alpha FT-IR mass spectrometer (Bruker), an Ultrospec™ 5300 pro UV/Visible Spectrophotometer (Amersham Biosciences), and an INOVA 600 MHz nuclear magnetic resonance spectrometer (Varian).

Compound SC3-22-3 and SC3-22-19 Isolation and Identification

Agar plugs of CR133B were initially grown at 25° C. on yeast malt agar plates supplemented with 30 μg/mL streptomycin and 12 μg/mL chlortetracycline. After one week, 3 macerated agar plugs of this plate were placed in 75 mL of rich seed media with a pH value of 6.2 [peptone (5 g/L), dextrose (10 g/L), yeast extract (3 g/L), and malt extract (10 g/L), pH 6.2] in a 1 L flask. It was grown at 25° C. and 150 rpm for 6 days. It was grown at 25° C. and 150 rpm for 6 days. 450 mL of 0.66% (w/v) malt extract and 10 g HP-20 resin were then added to each flask, and the fungi were cultured under the same conditions for 21 days. The fungal cultures were then held at 25° C. without shaking for 5 days.

Figure 4B:
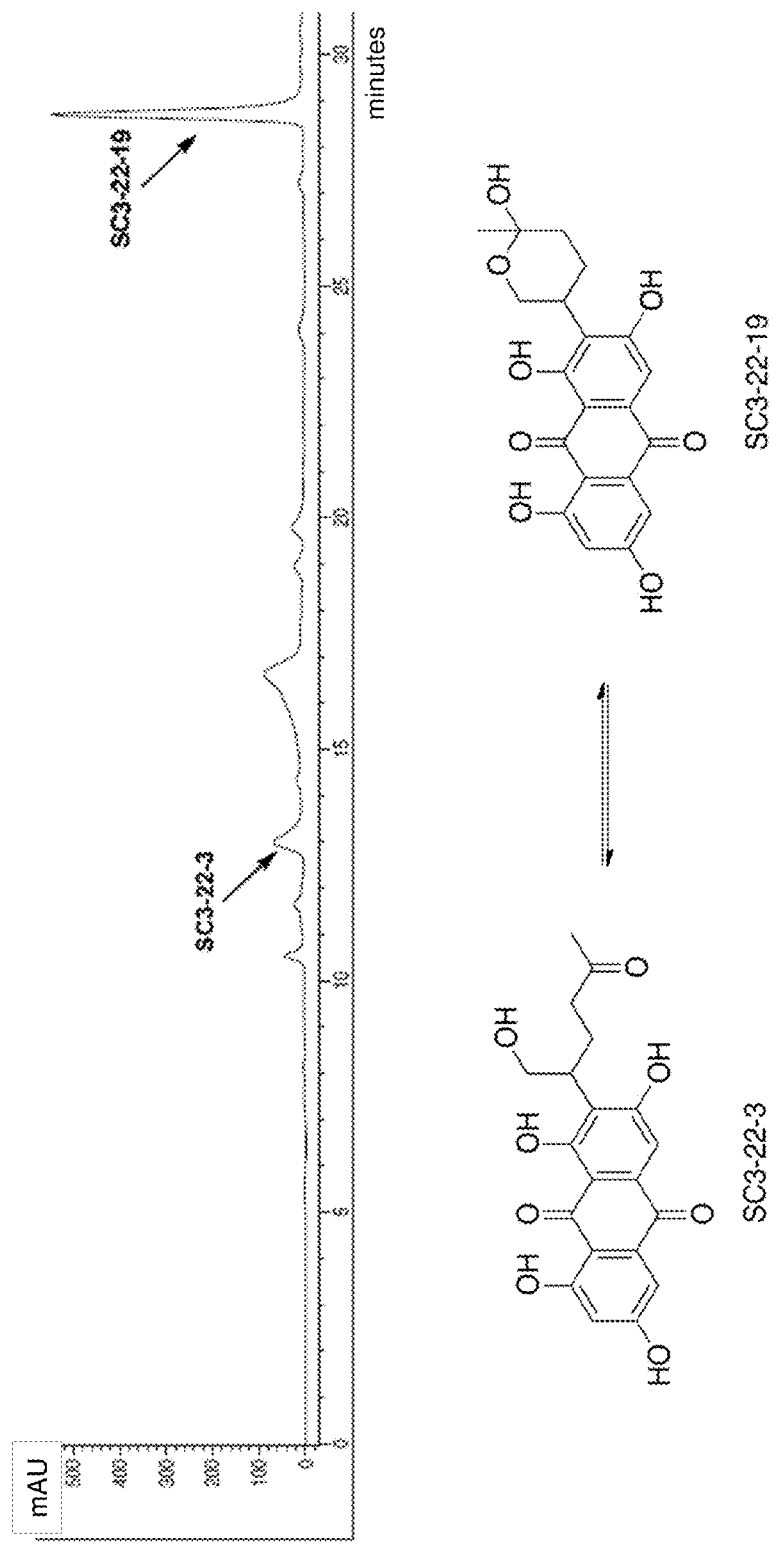
Figure 4C:
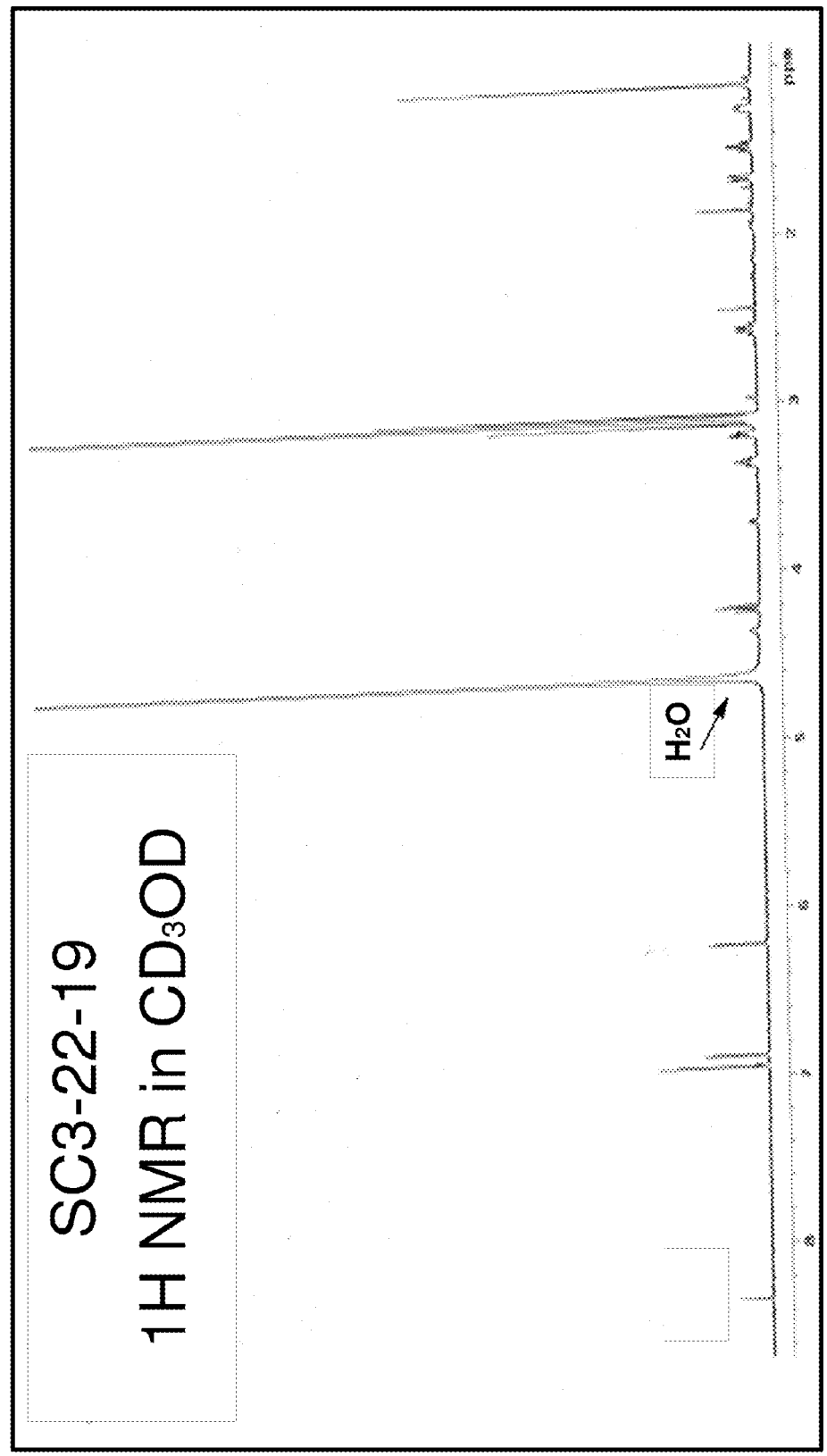
Figure 4D:
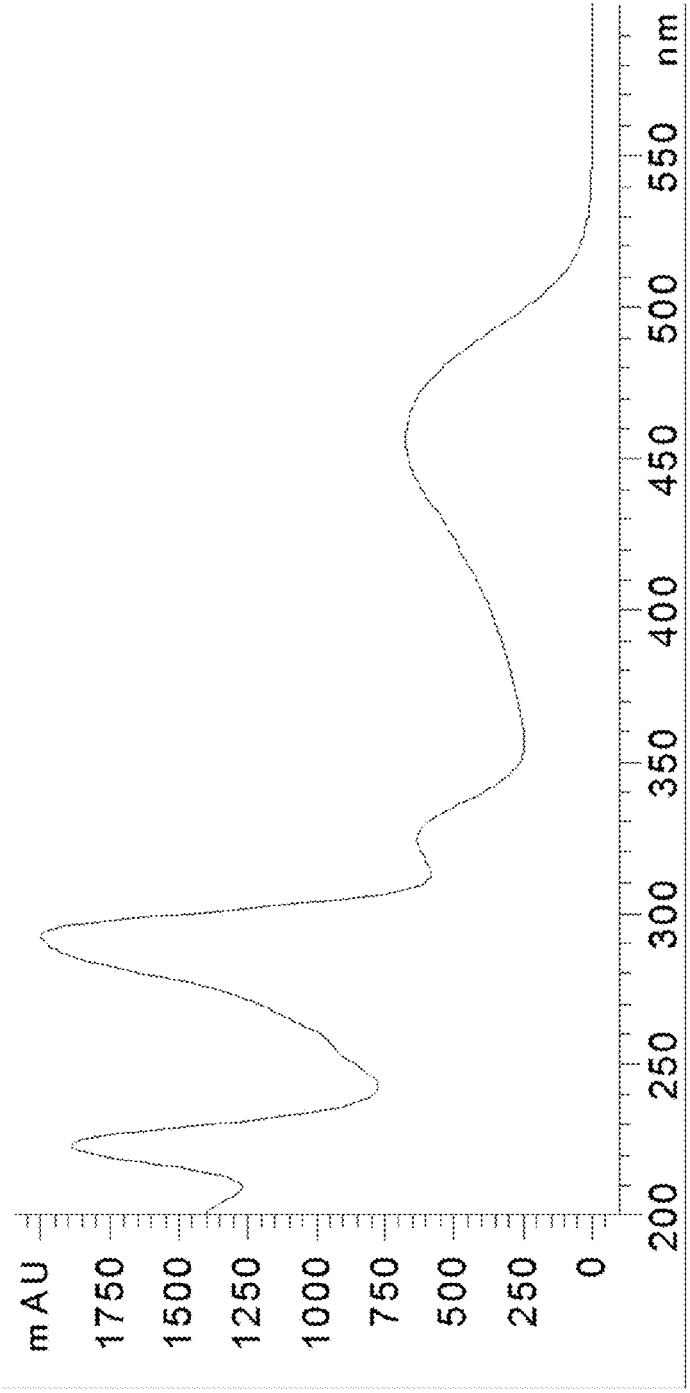
Figure 4E:
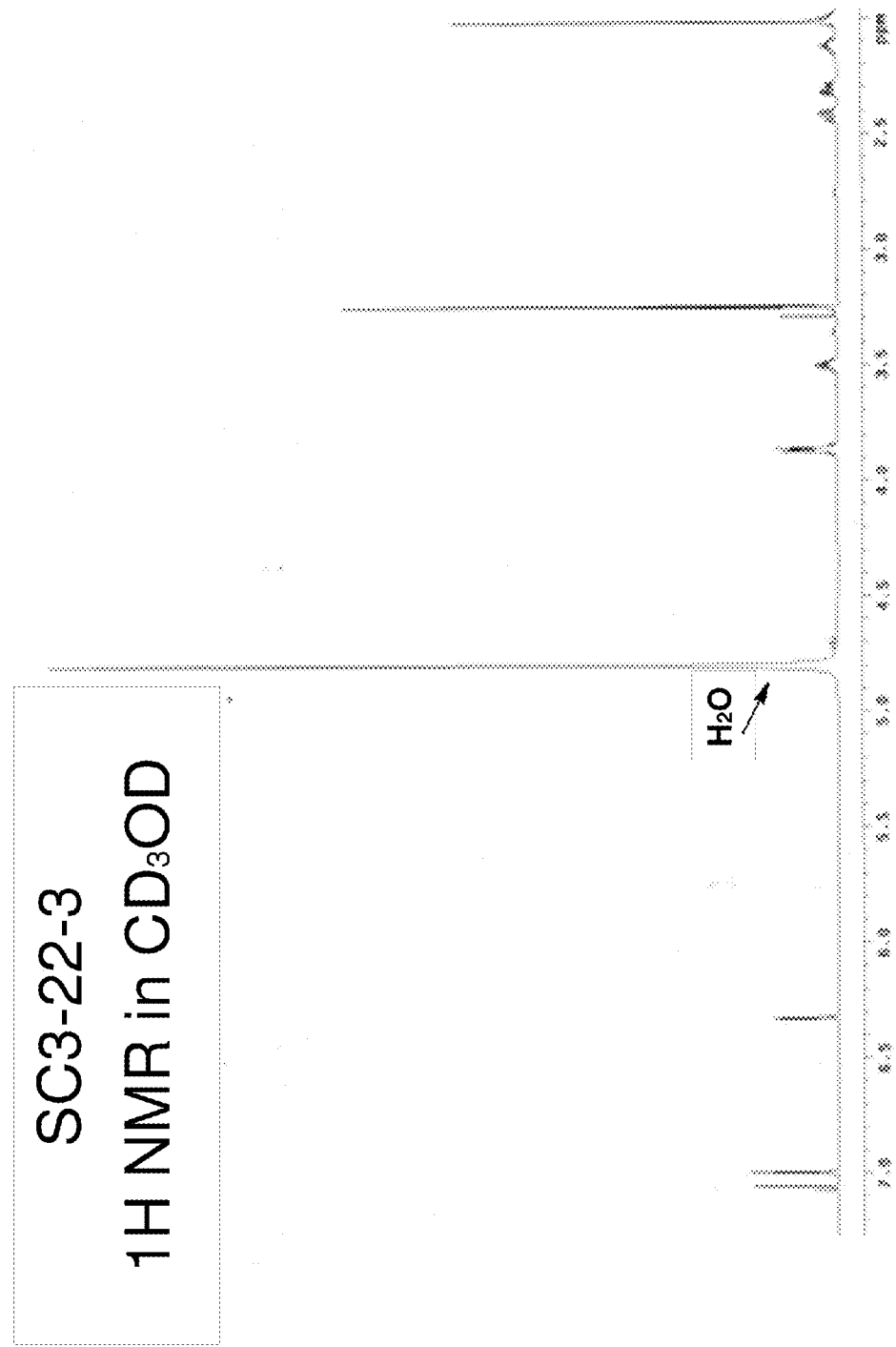
Figure 4F:
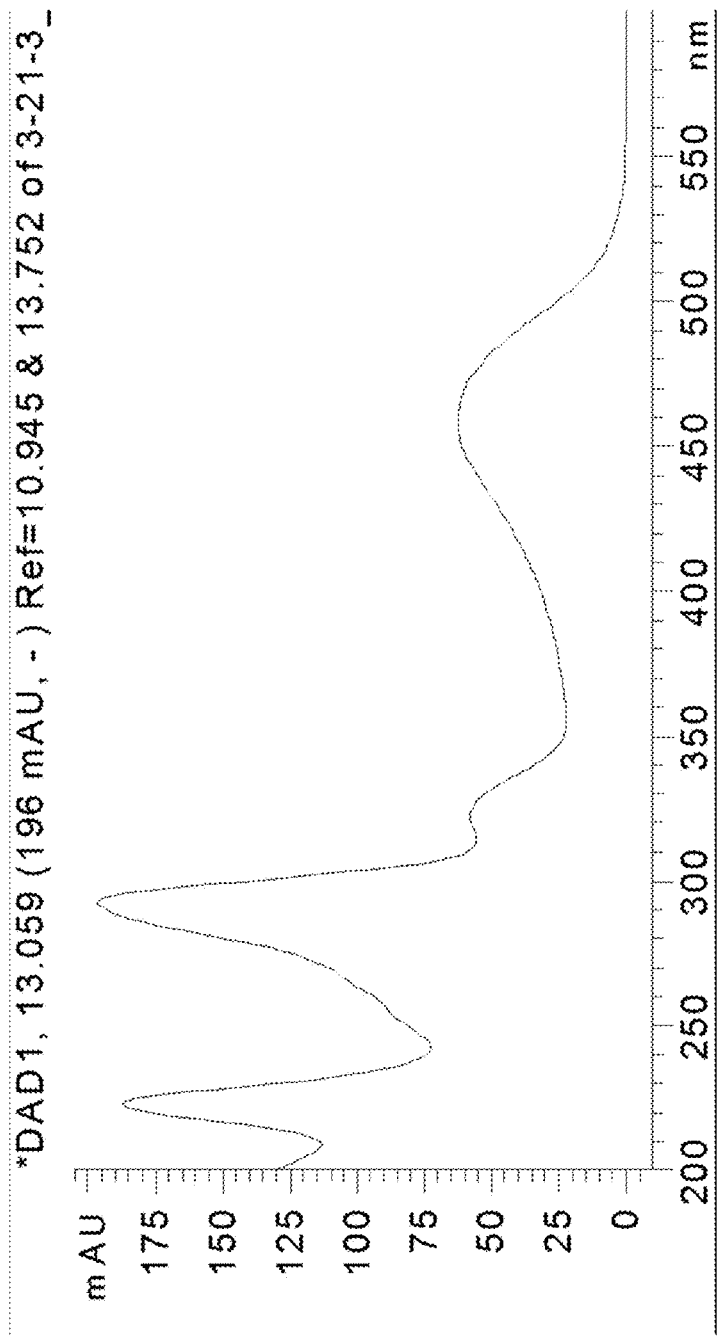
Figure 5A:
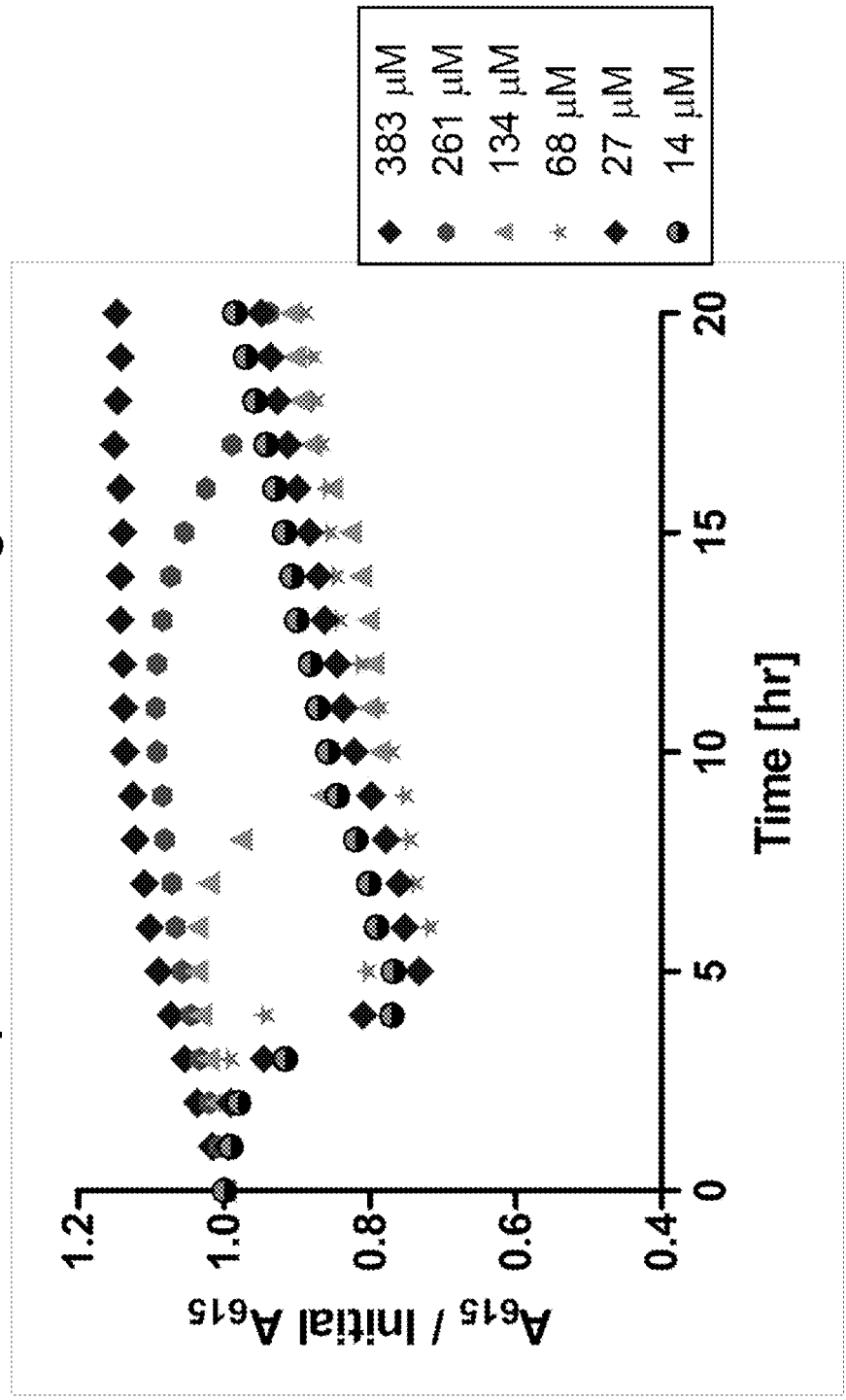
FIGS. 5A-5F depict the effect of compounds 1, 2, and 3 on *V. cholerae* sugar fermentation and growth. The assays were carried out at 30° C. in pH-MM$_{Suc}$ to monitor sugar fermentation by A615 (FIGS. 5A, 5B, and 5C) or in MM$_{Pyr}$ to monitor bacterial growth by OD$_{615}$ (D, E, and F). Bacteria were exposed to compound 1 (FIGS. 5A and 5D), compound 2 (FIGS. 5B and 5E) or compound 3 (FIGS. 5C and 5F) at concentrations ranging from 14 to 383 µM.
Figure 5B:
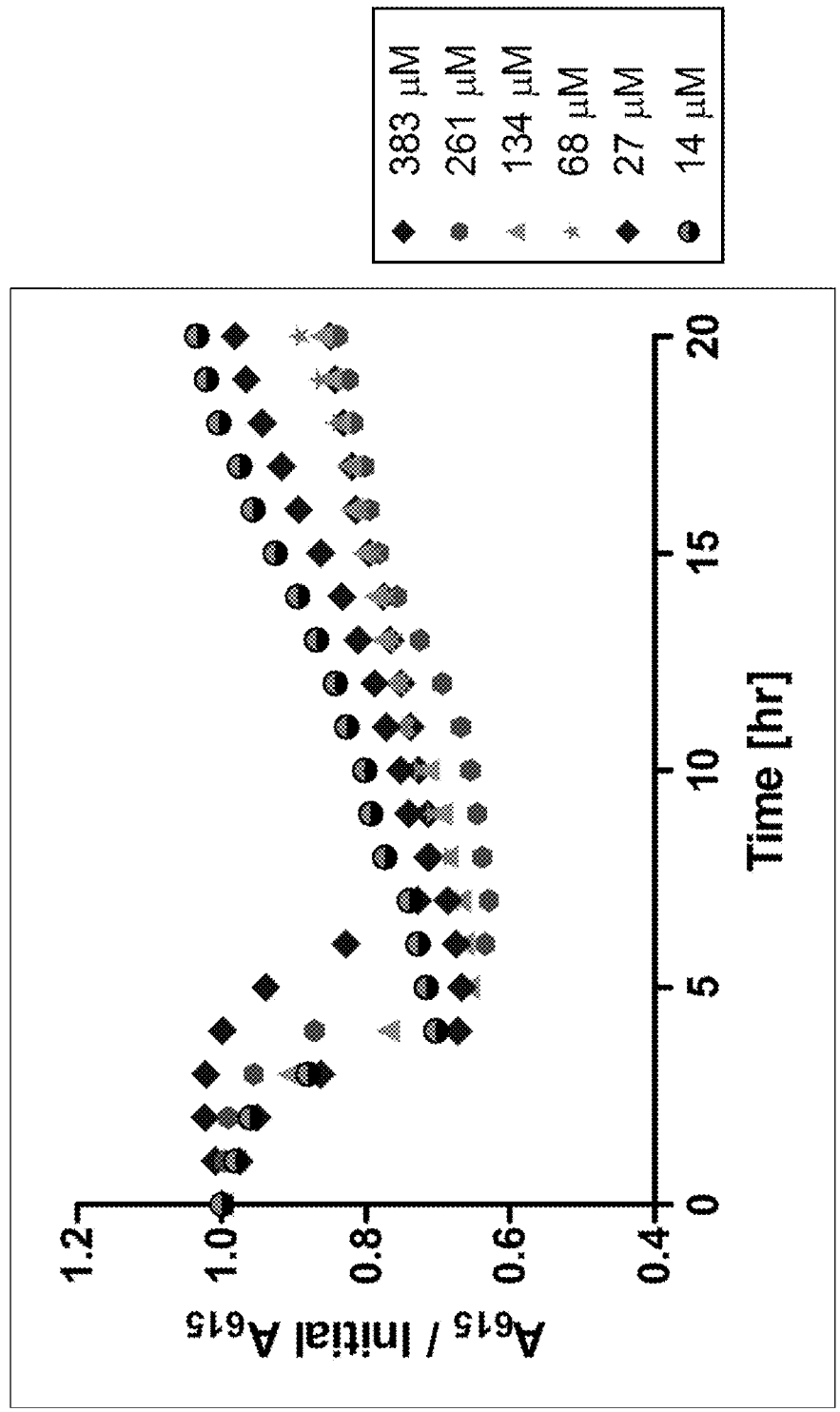
Figure 5C:
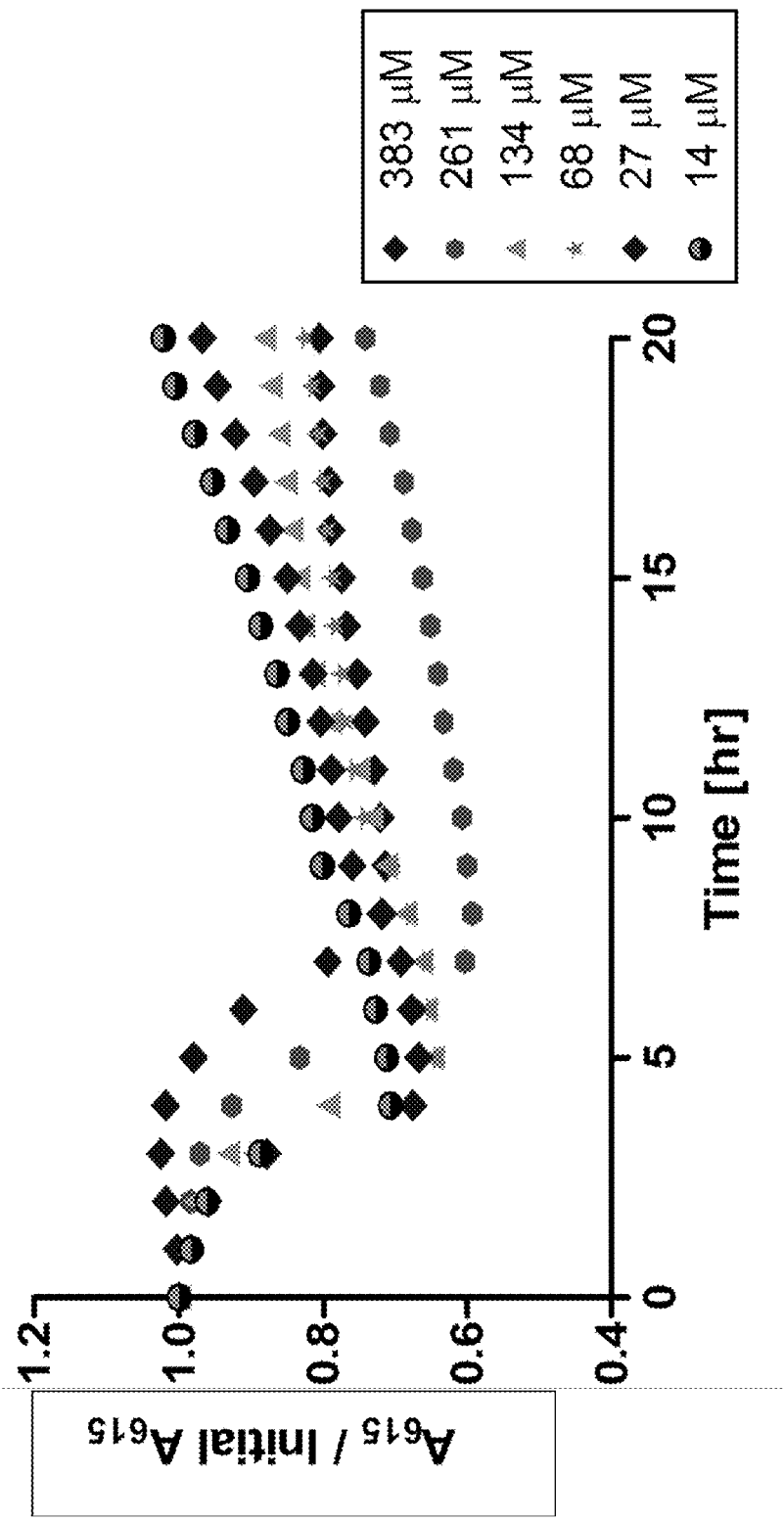
Figure 5D:
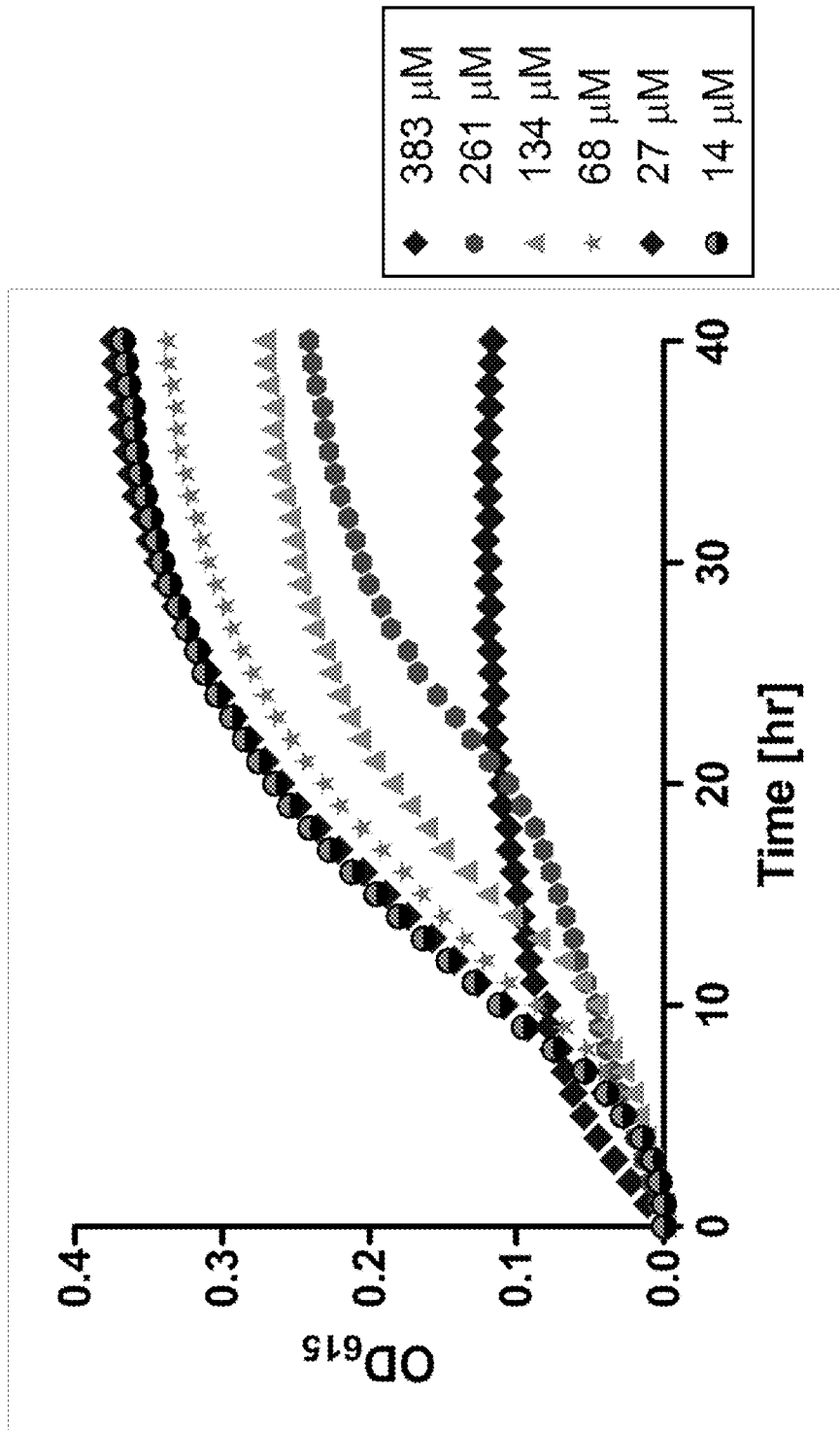
Figure 5E:
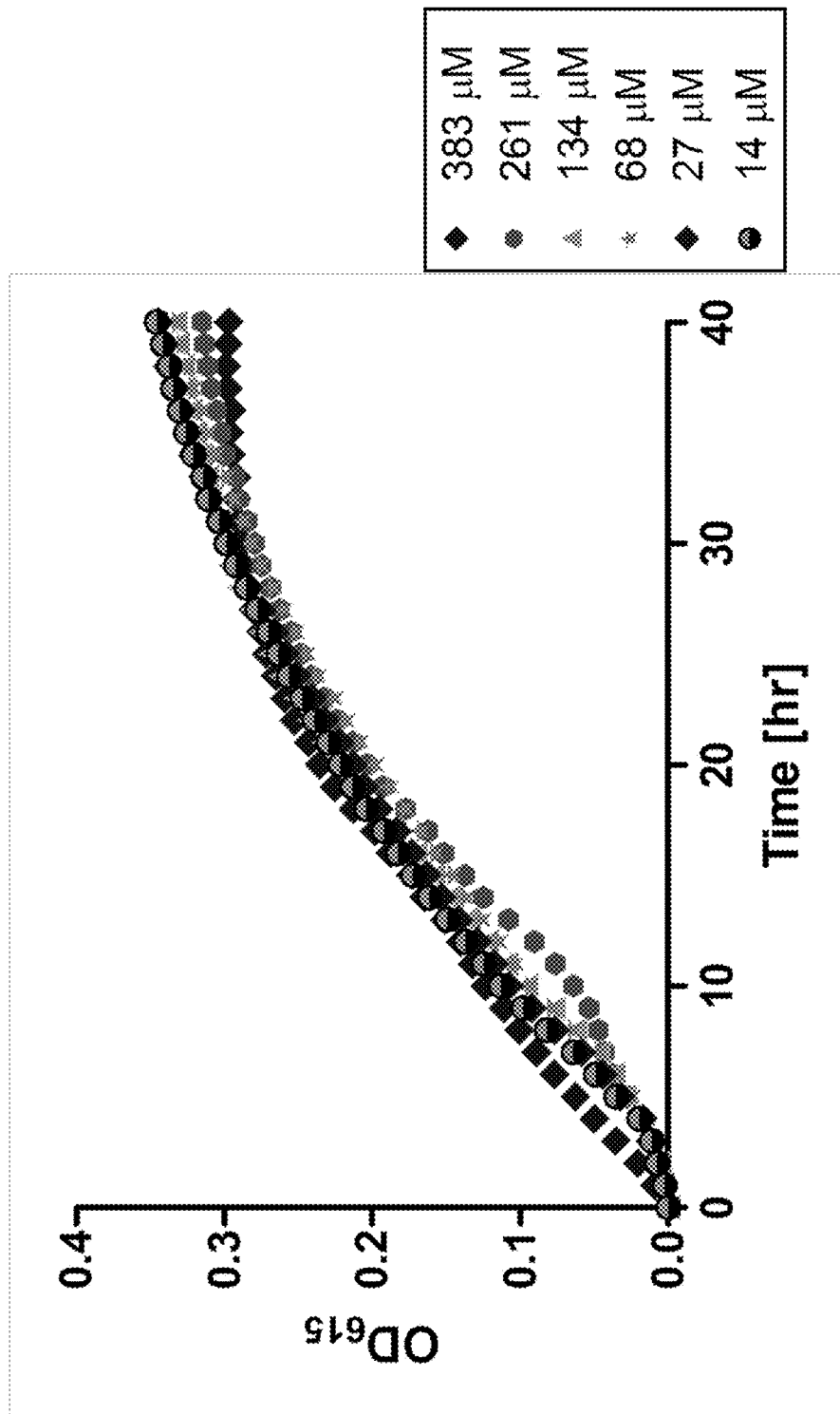
Figure 5F:
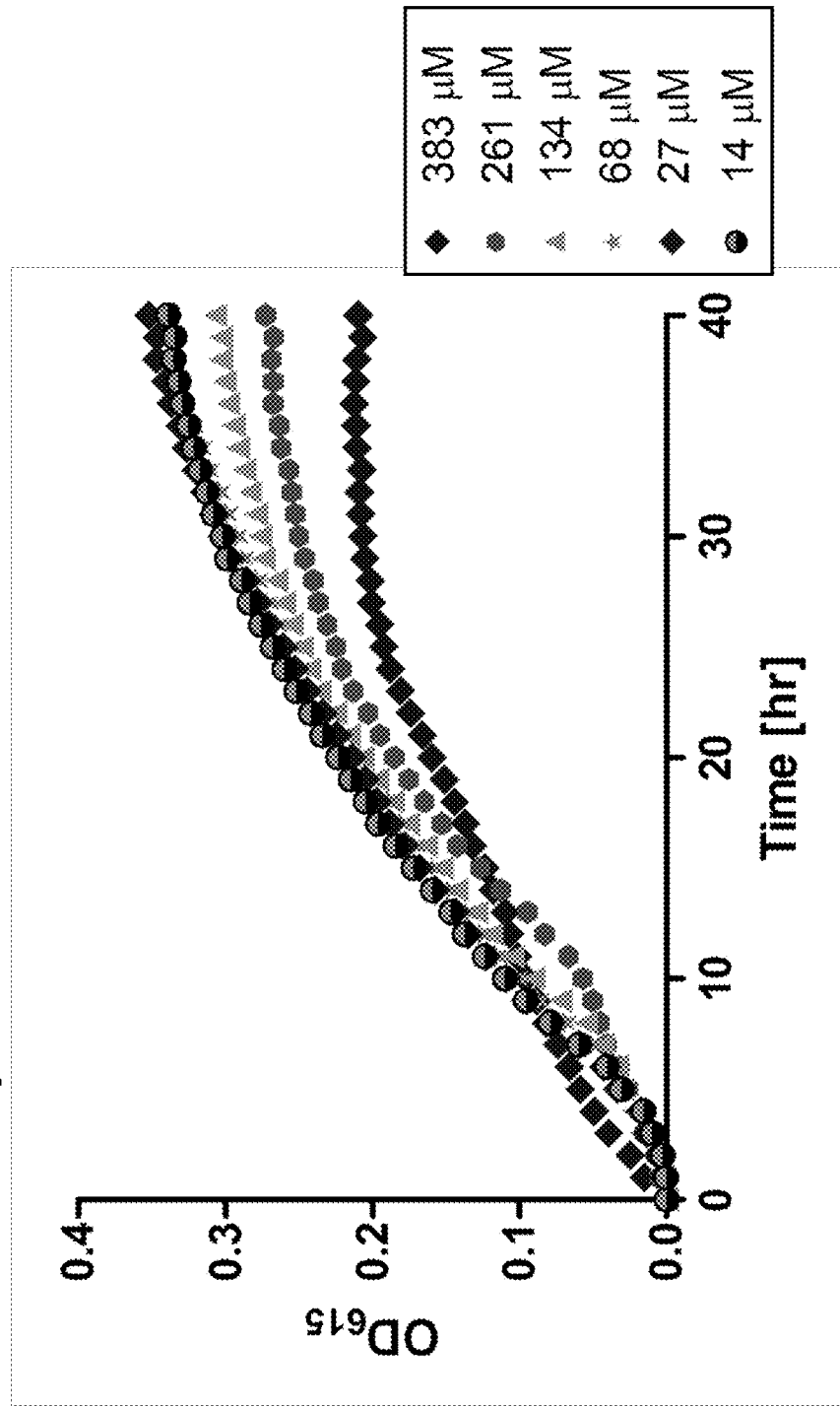
Figure 6A:
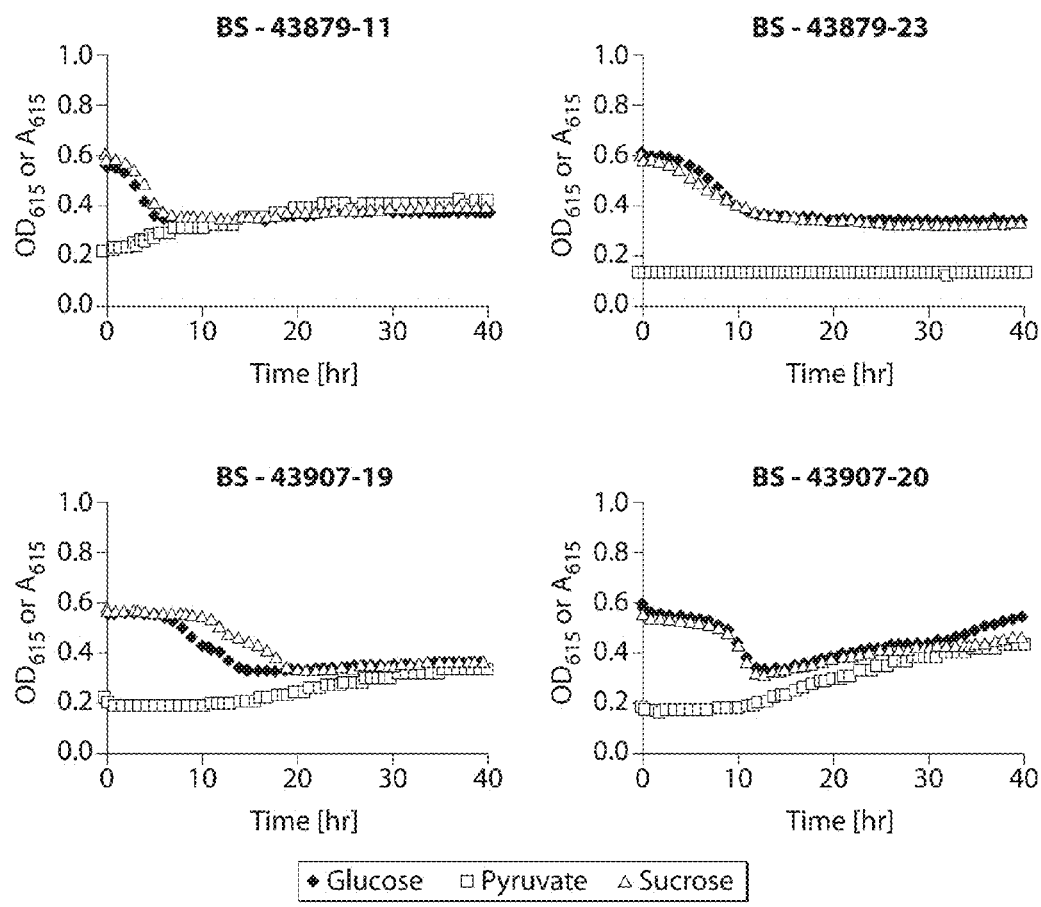
FIGS. 6A-6M depict natural extracts with reproducible effects on medium acidification by *V. cholerae*. Time course measurements of *V. cholerae* medium acidification in pH-MMSuc and pH-MMGlu or growth in MMPyr either alone (WT Control, see FIG. 6M) or in the presence of test extracts. Extract designation is indicated above each trace (see Table 2 for additional information on each extract).
Figure 6B:
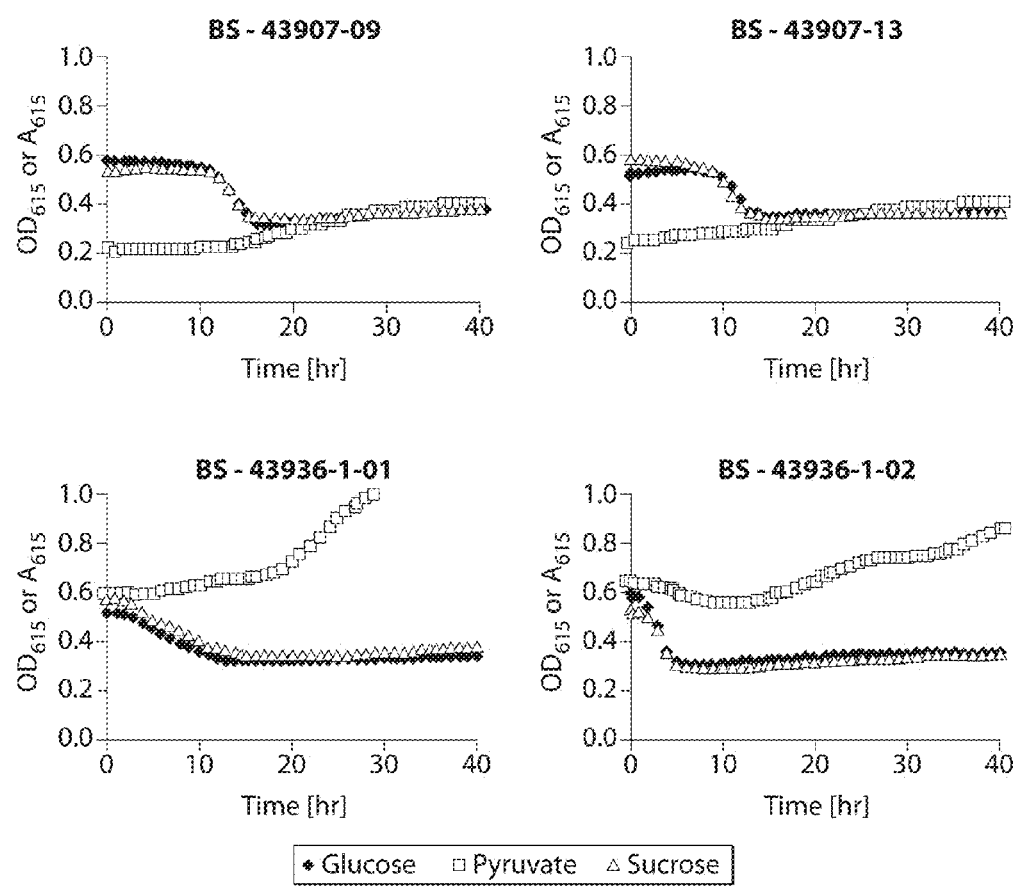
Figure 6C:
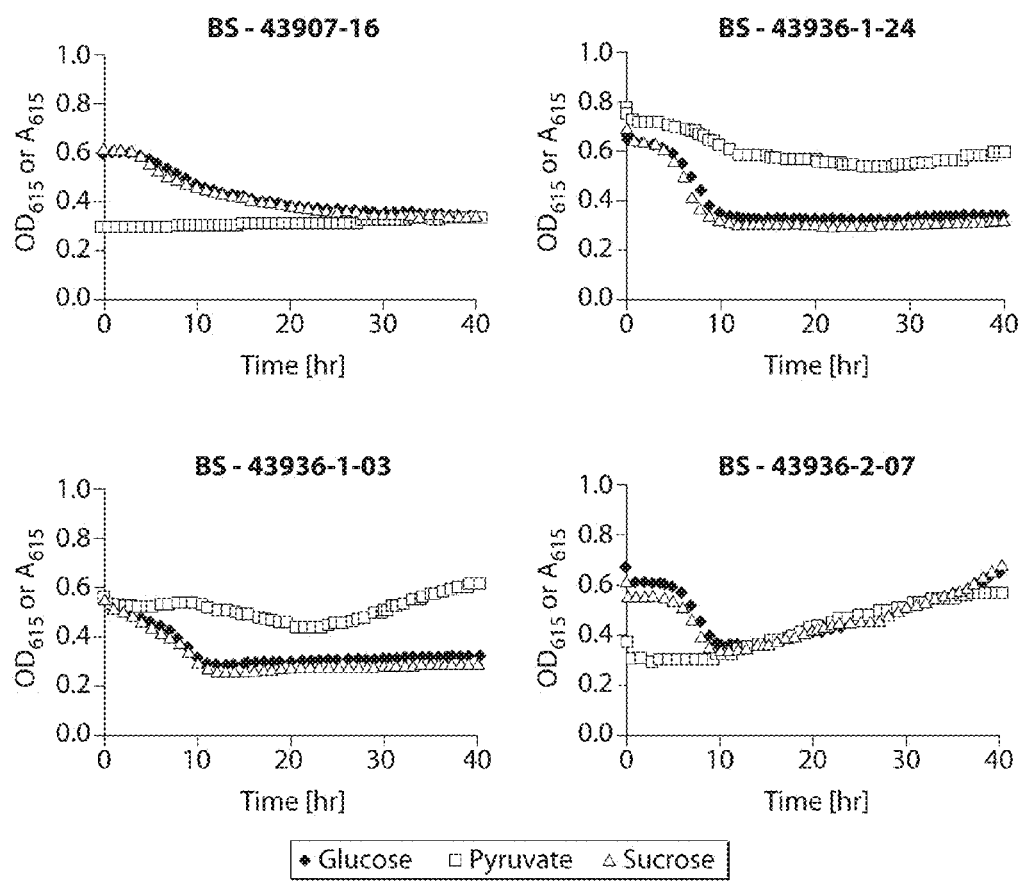
Figure 6D:
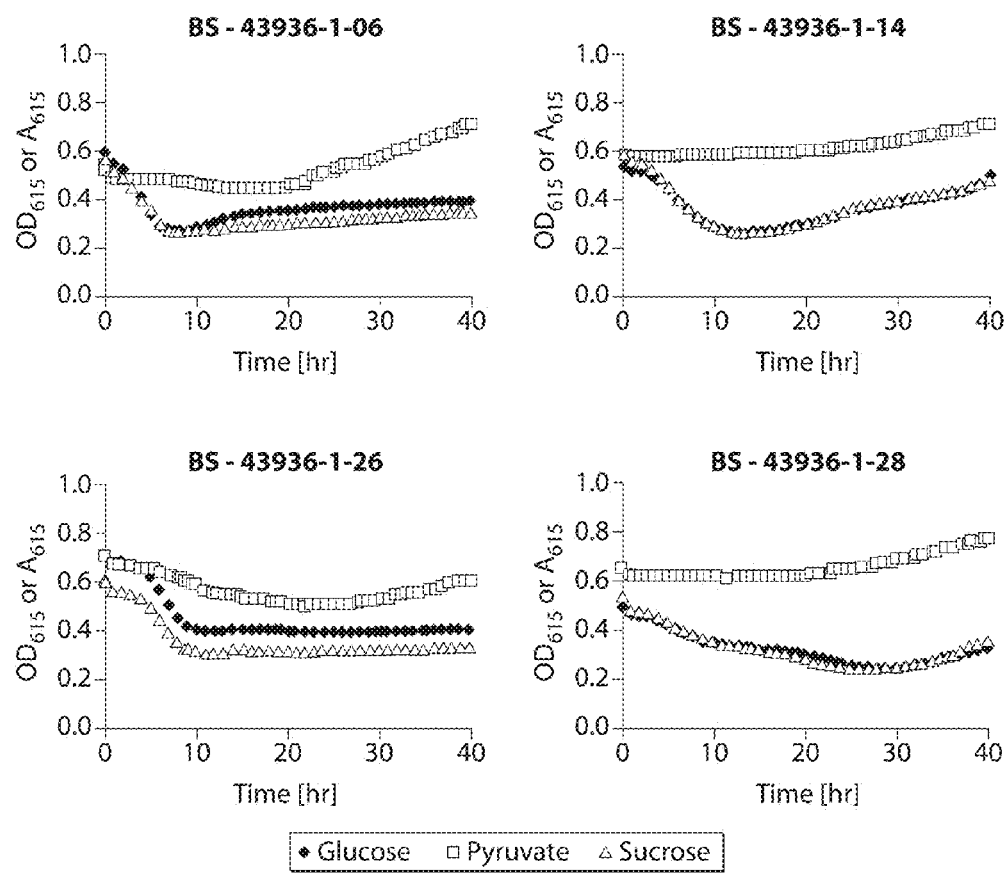
Figure 6E:
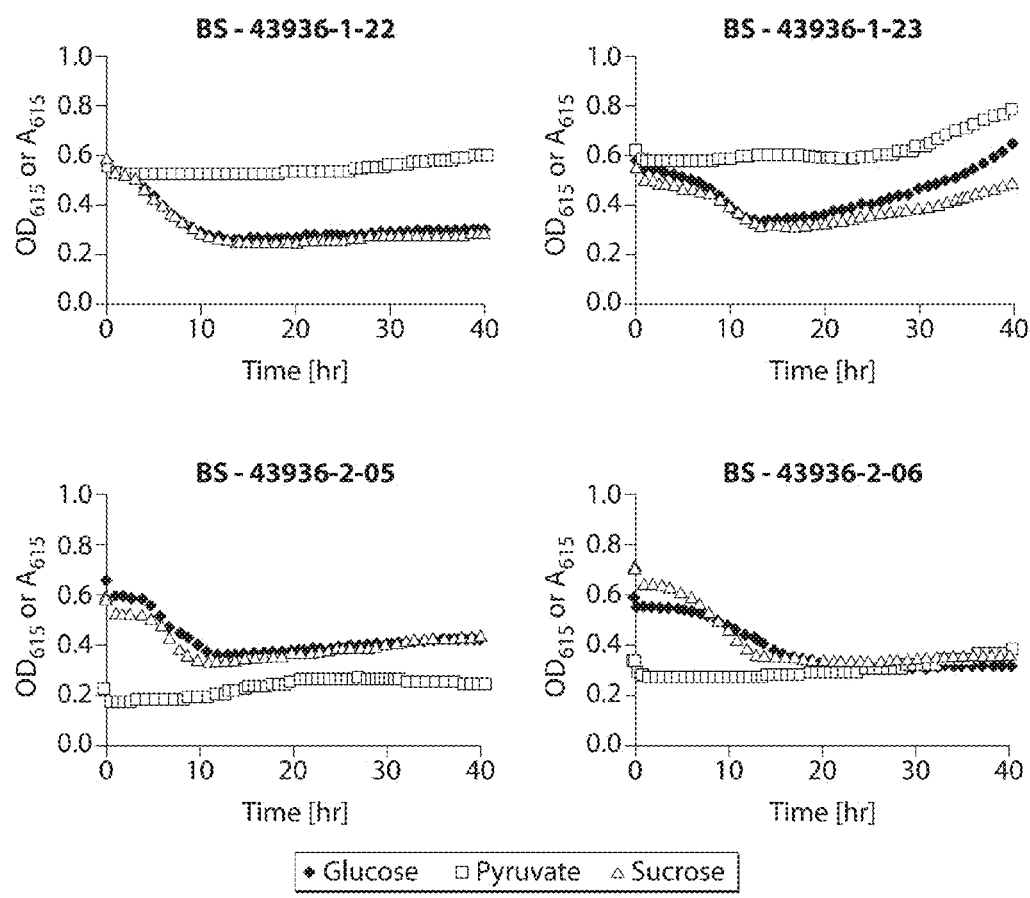
Figure 6F:
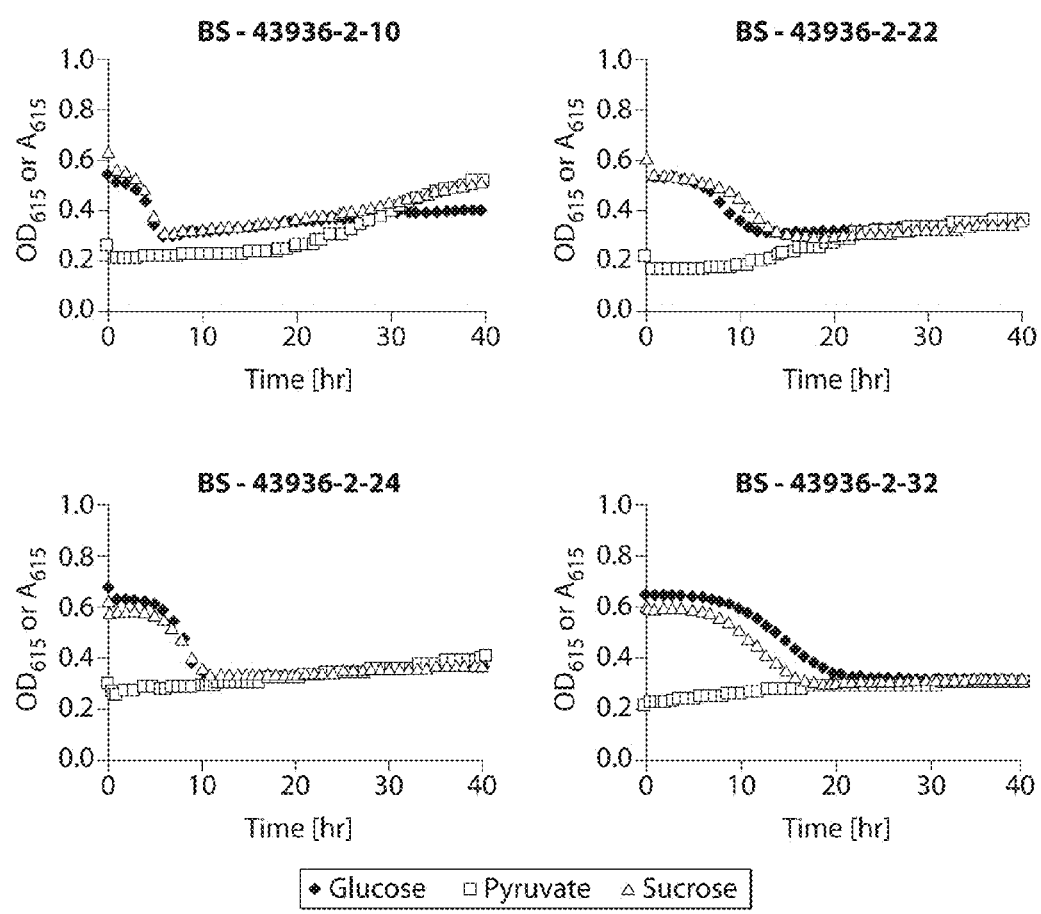
Figure 6G:
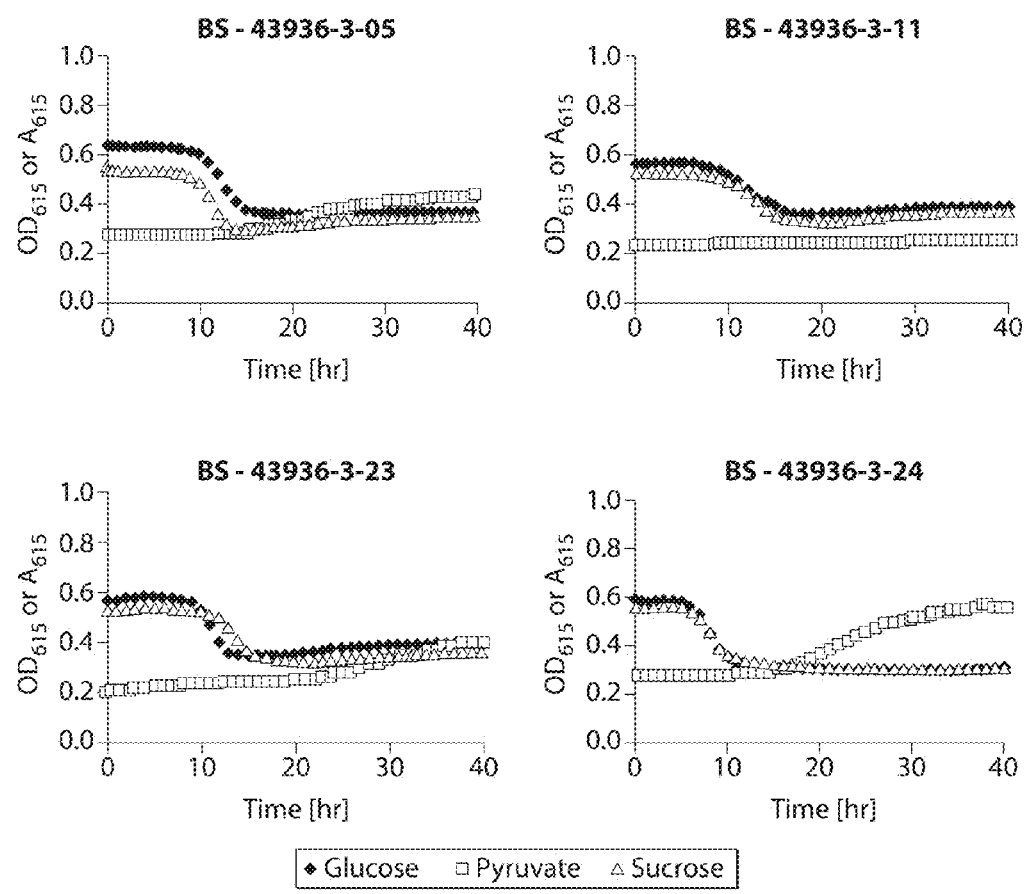
Figure 6H:
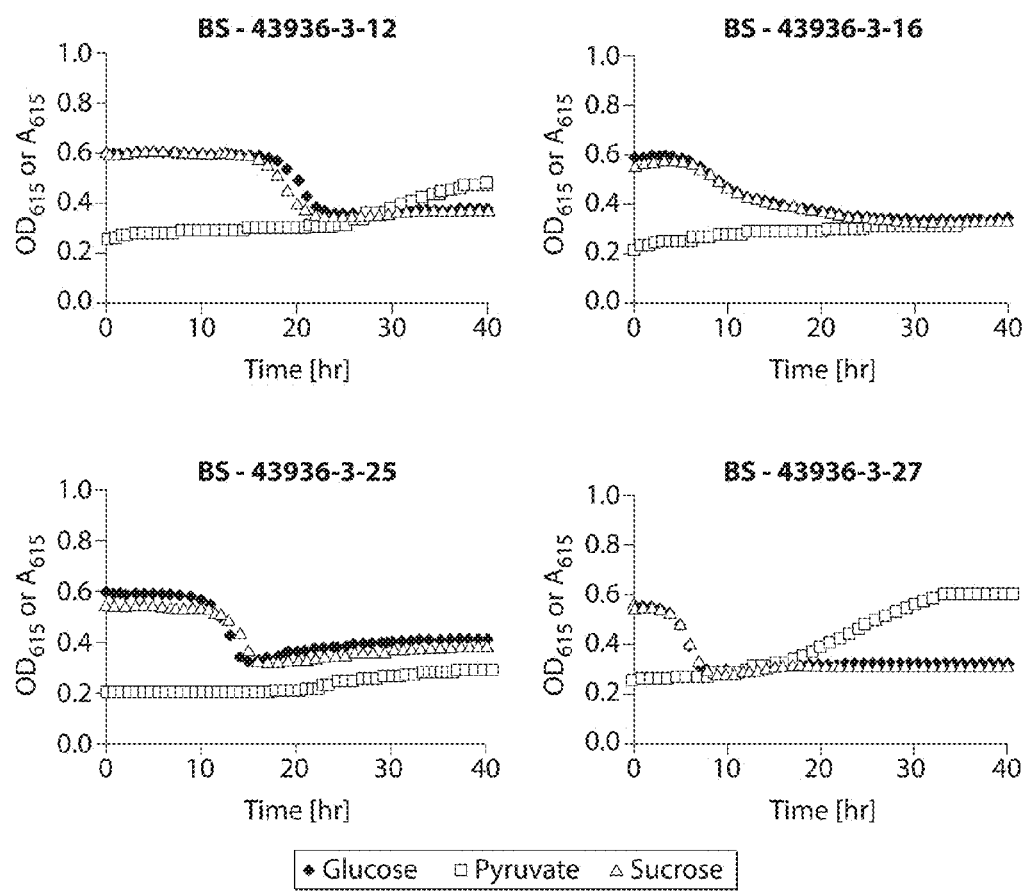
Figure 6I:
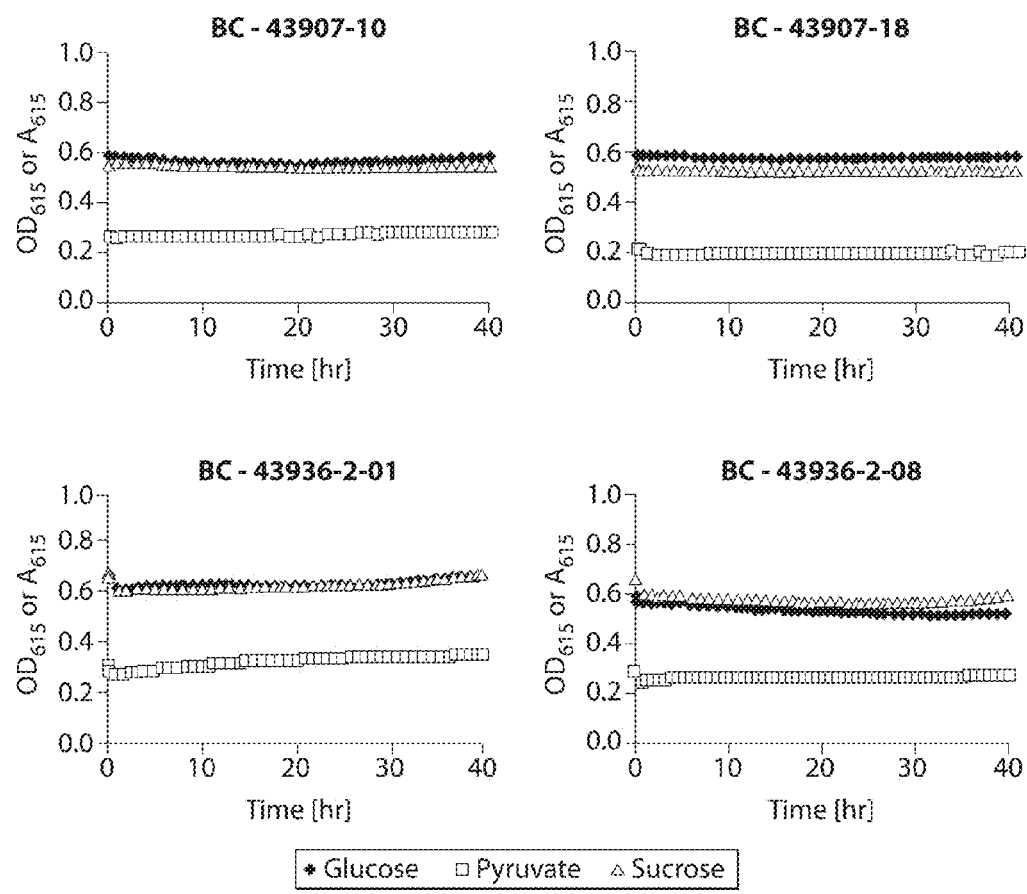
Figure 6J:
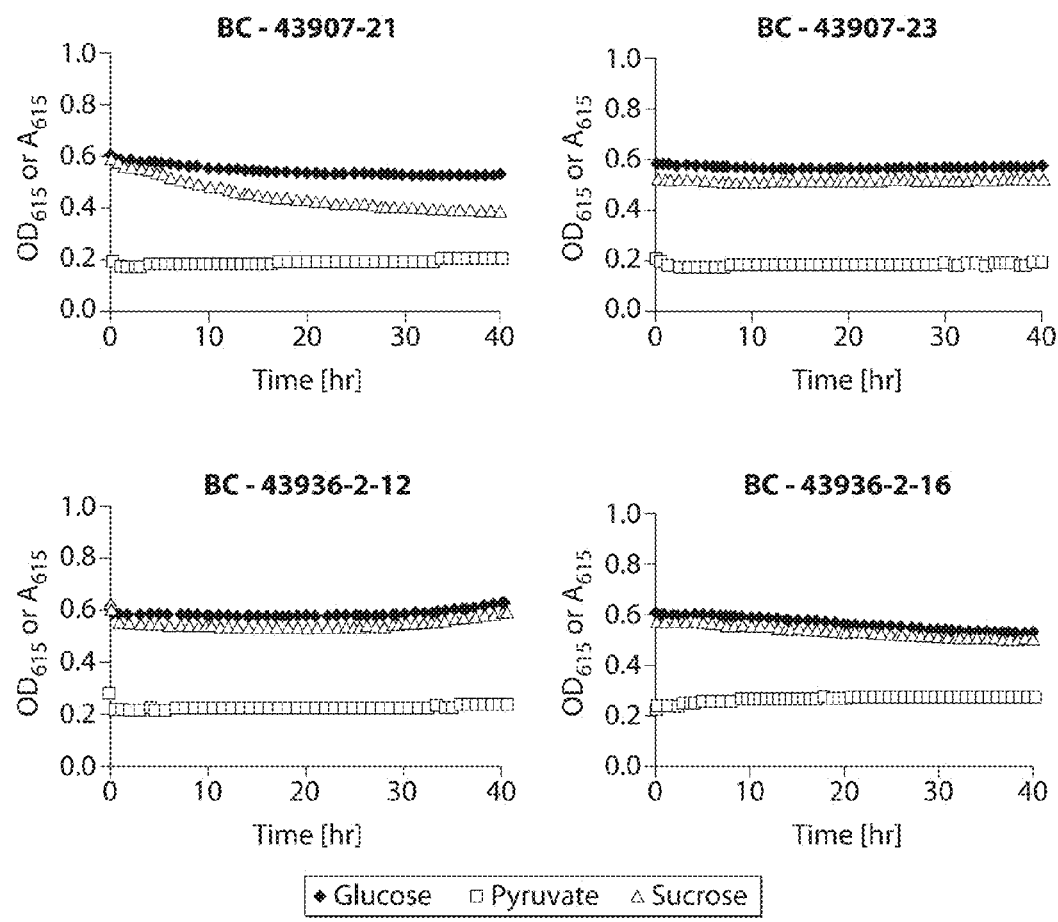
Figure 6K:
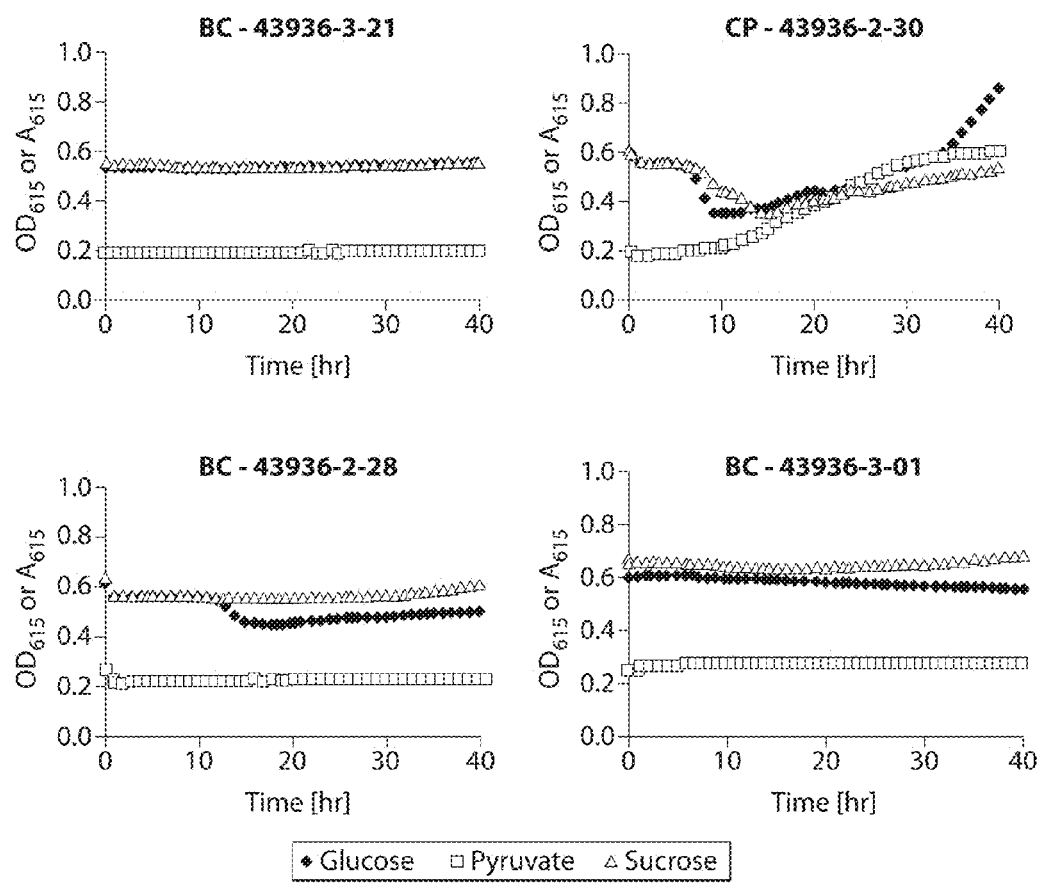
Figure 6L:
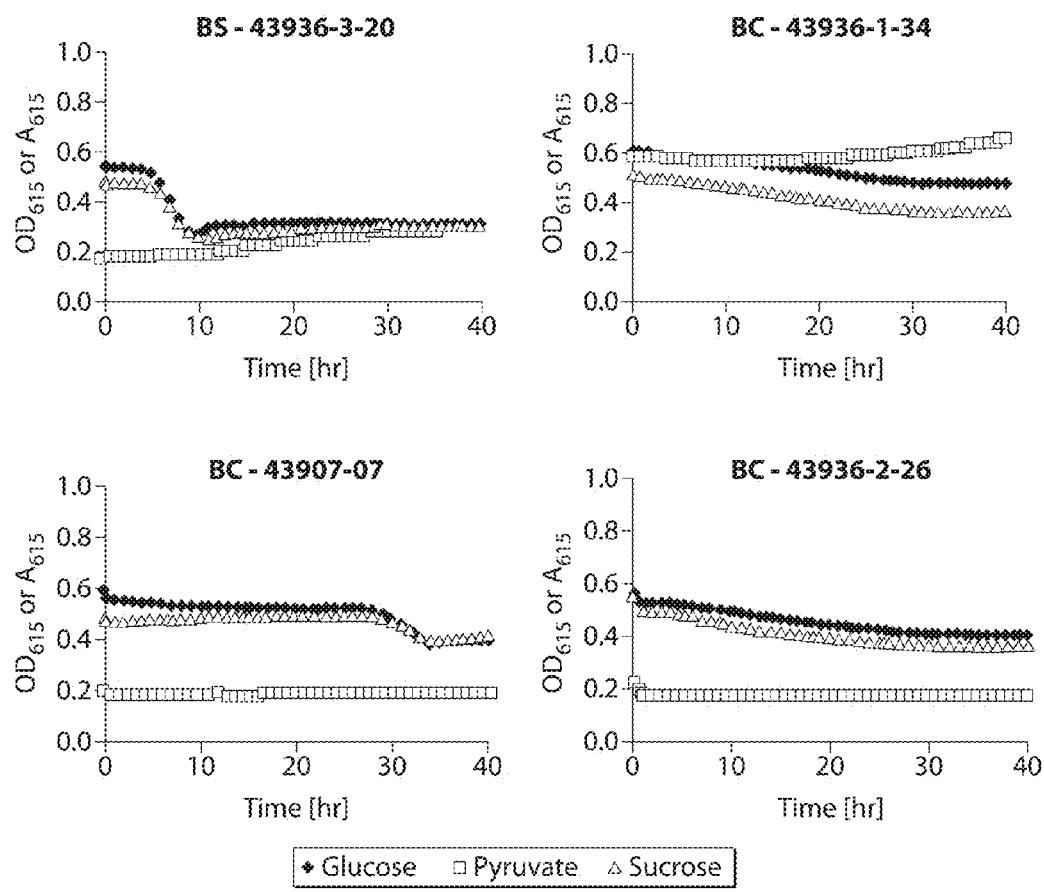
Figure 6M:
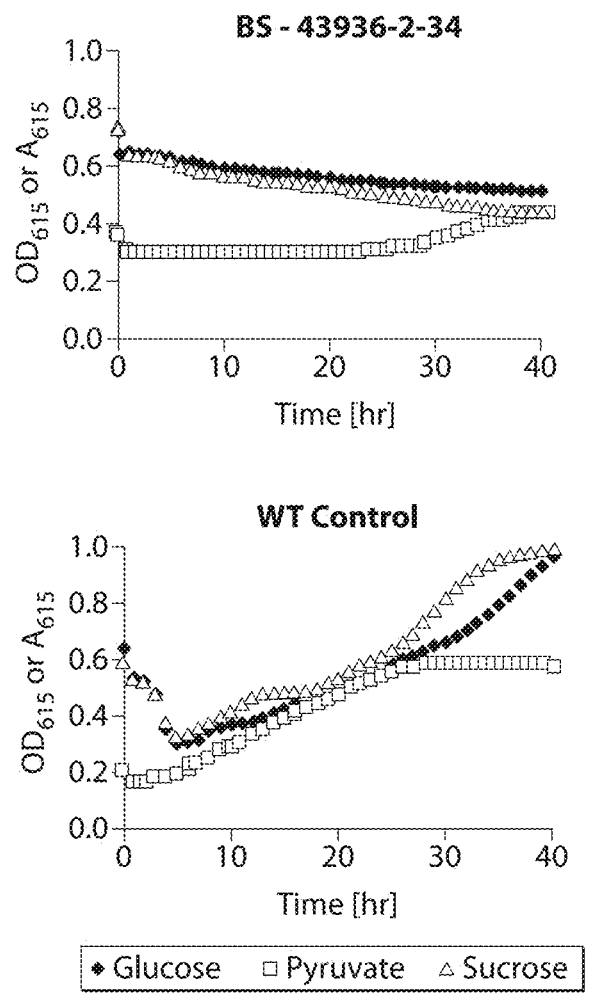
Figure 7A:
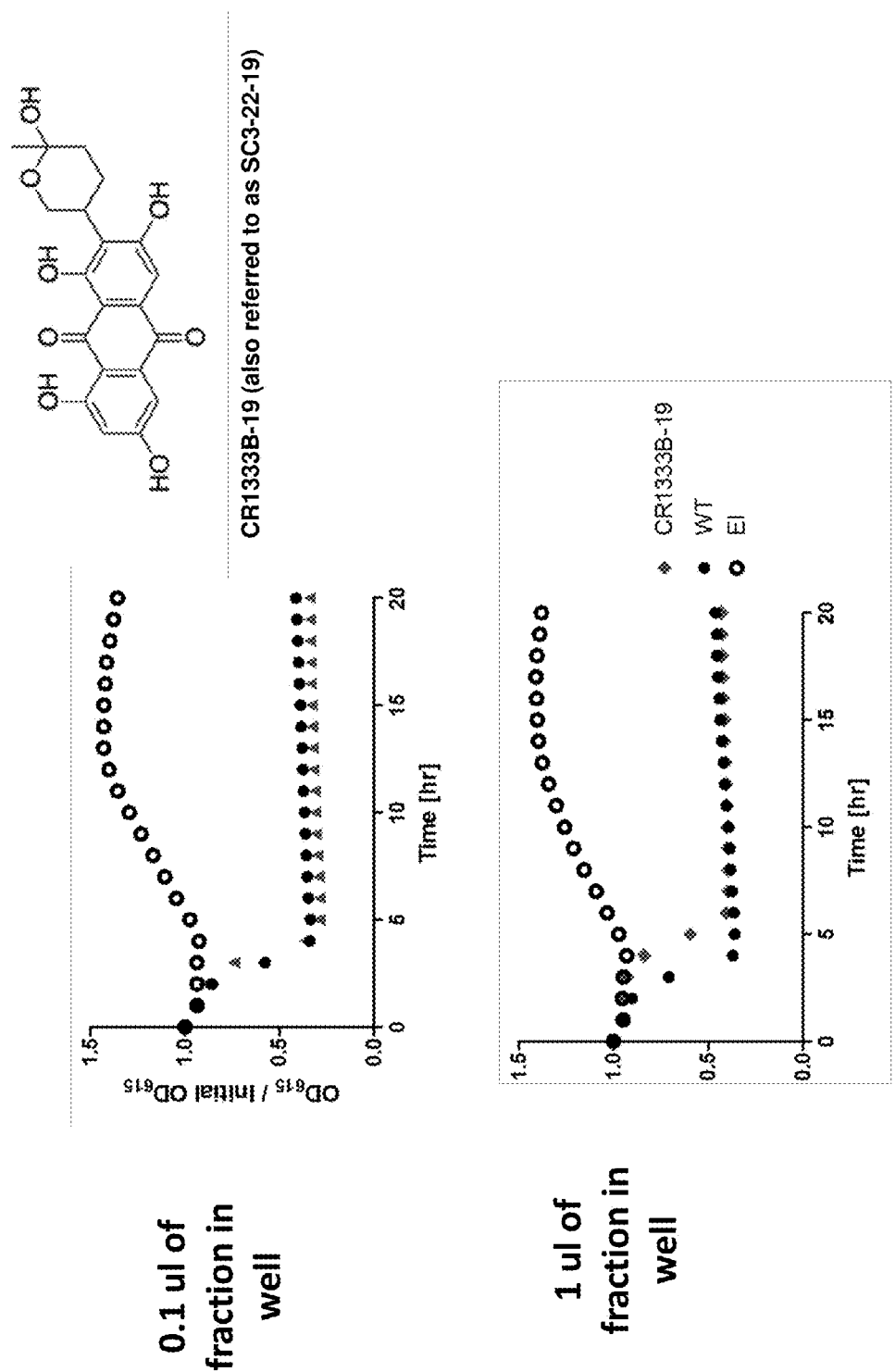
FIGS. 7A-7B depict the effect of compounds SC3-22-19 (FIG. 7A) and SC3-22-3 (FIG. 7B) on *V. cholerae* sugar fermentation and growth. The assays were carried out at 30° C. in pH-MM$_{Suc}$ to monitor sugar fermentation by A615. Bacteria were exposed to compounds SC3-22-19 and SC3-22-3 at 0.1 ul and 1 ul concentrations.
Figure 7B:
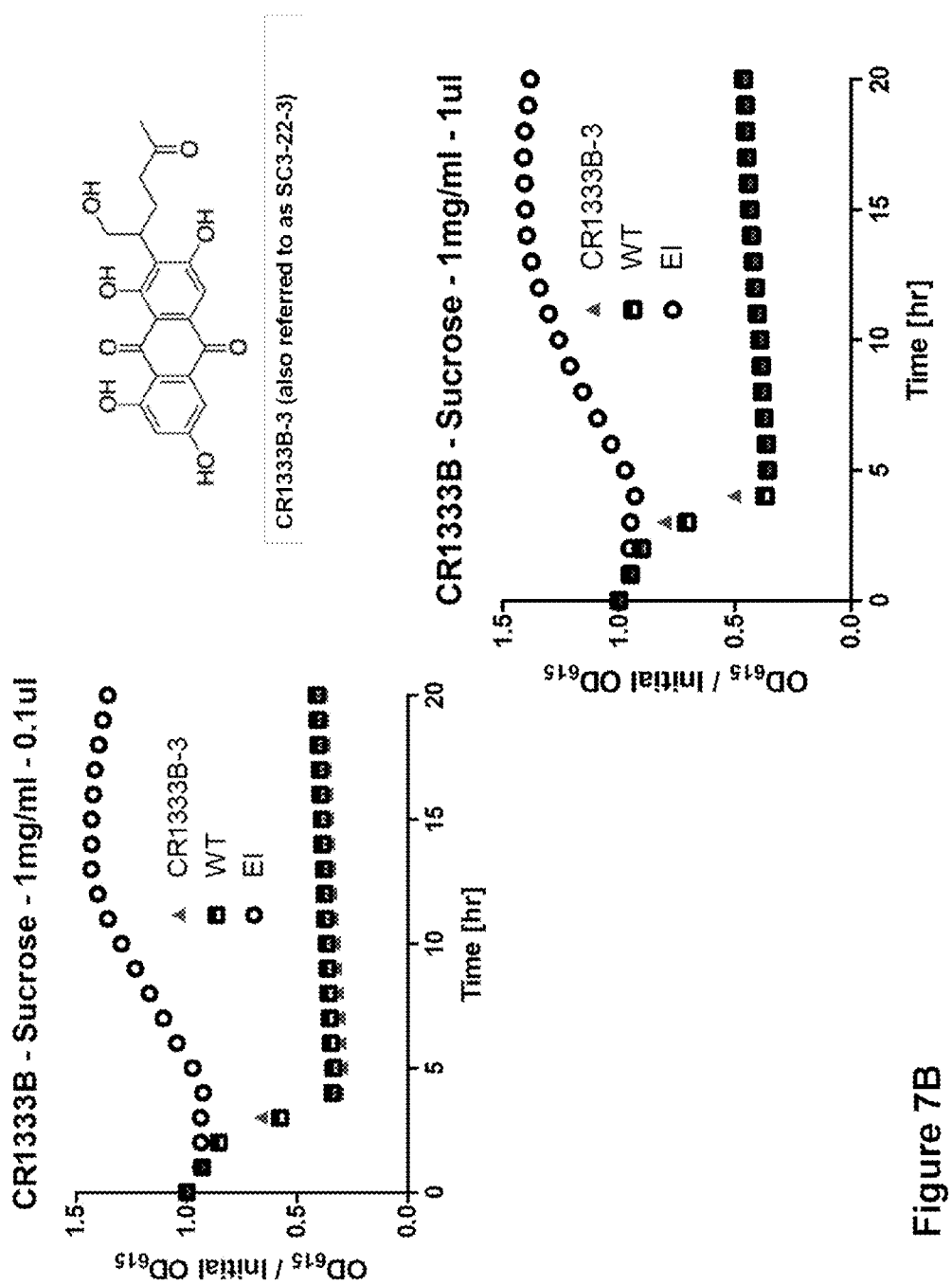

The culture was first filtered, and the HP-20 resin with myceria was extracted with ethanol (×3) to yield the crude extract. Flash chromatography of the crude CR133B was loaded over SPE C18 to yield three fractions. The main fraction, fraction II, was subjected to a Phenyl-hexyl prep-HPLC column (Phenomenex, Luna, 25 cm×10 mm, 5 μm particle size, 2 mL/min, 20% acetonitrile/water with 0.1% formic acid in 20 minutes and then to 100% in 10 minutes), which yielded compound SC3-22-3 ($t_R$: 13 min) and compound SC3-22-19 ($t_R$: 28.8 min). See FIG. 4B.

Physical Characterization of Compounds

All NMR experiments were carried out on a Varian INOVA 600 MHz spectrometer. IR and UV spectra were measured on Broker Alpha-P and Amersham Biosciences Ultrospec 5300 pro, UV/visible spectrophotometers, respectively. All the compounds were purified on an Agilent 1100 series HPLC (Agilent Technologies) using a preparative Phenomenex Luna Phenyl-hexyl column.

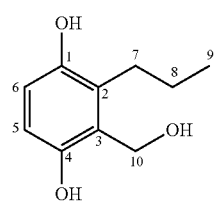

1

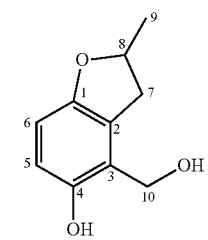

2

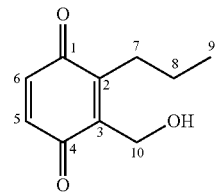

3

SC2-133-1 (compound 1): light yellow powder; UV (MeOH). $\lambda_{max}$ (log ε) 207 (4.16), 299 (3.48) nm; IR v 3327, 2961, 2931, 2872, 1648, 1585, 1487, 1464, 1349, 1282, 1254, 1224, 1102, 998, 968, 811, 758 cm$^{-1}$; HRMS m/z 205.0839 ([M+Na]), calcd for $C_{10}H_{14}O_3Na$, 205.0841).

SC2-133-2 (compound 2): light yellow powder; $[a]^{23}_D$+2.1 (c 0.28, EtOH); UV (MeOH) $\lambda_{max}$ (log ε) 206 (3.80), 223 (sh), 235 (sh), 305 (3.03) nm; IR V 3323, 2963, 2918, 1646, 1579, 1462, 1380, 1348, 1227, 1028, 989, 813, 767 cm$^{-1}$; HRMS m/z 203.0686 ([M+Na]), calcd for $C_{10}H_{12}O_3Na$, 203.0684).

SC2-133-3 (compound 3): yellow powder; UV (MeOH) $\lambda_{max}$ (log ε) 204 (3.55), 247 (3.18), 300 (2.71), 381 (2.28) nm; IR v 3336, 2962, 2926, 1647, 1587, 1464, 1384, 1350, 1280, 1101, 1010 cm$^{-1}$; HRMS m/z 203.0681 ([M+Na]), calcd for $C_{10}H_{12}O_3Na$, 203.0684).

TABLE 2

$^1$H[a] and $^{13}$C[b] NMR Data of Compounds 1 to 3 (in CD$_3$OD)

| | $^1$H | | | $^{13}$C | | |
|---|---|---|---|---|---|---|
| # | 1 (SC2-133-1) | 2 (SC2-133-2) | 3 (SC2-133-3) | 1 | 2 | 3 |
| 1 | | | | 149.9 | 153.5 | 189.2 |
| 2 | | | | 131.4 | 128.1 | 147.6 |
| 3 | | | | 121.4 | 124.6 | 141.9 |
| 4 | | | | 148.9 | 150.2 | 188.4 |
| 5 | 6.56 (d, 8) | 6.52 (d, 8) | 6.77 (br s) | 115.4 | 114.9 | 137.4 |
| 6 | 6.48 (d, 8) | 6.43 (d, 8) | 6.77 (br s) | 114.0 | 108.9 | 137.4 |
| 7 | 2.60 (m) | 3.34 (dd, 12, 6) 2.80 (dd, 18, 6) | 2.55 (m) | 28.7 | 36.9 | 28.8 |
| 8 | 1.51 (m) | 4.82 (m) | 1.48 (m) | 24.1 | 80.5 | 24.1 |
| 9 | 0.96 (t, 6.6) | 1.39 (t, 6.6) | 0.97 (t, 6.6) | 14.2 | 21.7 | 14.4 |
| 10 | 4.52 (s) | 4.61 (s) | 4.47 (s) | 55.5 | 58.6 | 55.3 |

[a]δ (ppm) 600 MHz; multiplicities; J values (Hz) in parentheses. [b]δ (ppm) 150 MHz, from gHSQCed and gHMBC.

In the COSY spectrum of 1, two spin systems were observed, H—H and CH$_2$—CH$_2$—CH$_3$. In the HMBC spectrum of 1, $^2$J and $^3$J correlations from H-7 to C-1 ($\delta_C$ 149.9), C-2, and C-3, and from H-10 to C-2, C-3, and C-4 ($\delta_C$ 148.9) were observed indicating that 1 was a hydroquinone with the propyl and hydroxymethyl groups adjacent to each other, and the two aromatic protons at the other side of the molecule.

Hence, the structure of 1 was determined as shown. Similarly, the structures of compounds 2 and 3 were also elucidated using spectroscopic data.

The $^1$H NMR and UV spectra of SC3-22-19 and SC3-22-3 are provided in FIGS. 4C to 4F.

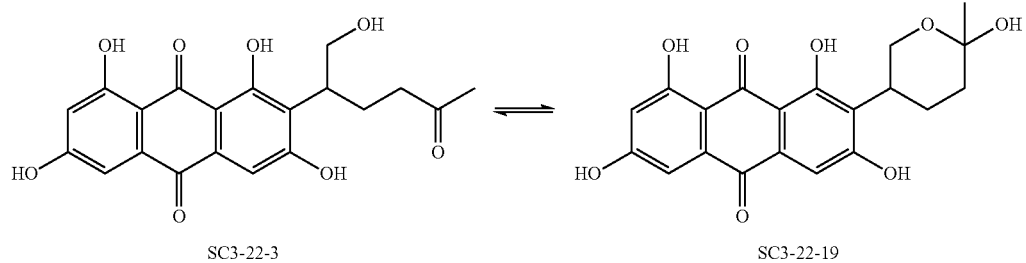 [SMILES: CC(=O)CCC(CO)c1c(O)cc2c(c1O)C(=O)c1c(O)cc(O)cc1C2=O ; CC1(O)CCC(c2c(O)cc3c(c2O)C(=O)c2c(O)cc(O)cc2C3=O)CO1]

SC3-22-3                    SC3-22-19

Determination of Minimum Inhibitory Concentrations (MIC)

The MICs for all species except for *M. tuberculosis* were determined in cation-adjusted Mueller-Hinton broth (CAMHB) using the microdilution broth method, according to M07-A8 and M100-S21 guidelines. See Clinical and Laboratory Standards Institute (2009) Methods for dilution antimicrobial susceptibility tests for bacteria that grow aerobically; approved standard M07-A8, 8th ed. CLSI, Wayne, Pa., and Clinical and Laboratory Standards Institute (2011) Performance standards for antimicrobial susceptibility testing, 21st informational supplement M100-S21. CLSI, Wayne, Pa. Standardized inocula of each bacterium were prepared from cultures grown overnight at 37° C. in CAMHB, which were subsequently diluted 1:50 in fresh CAMHB and grown for 3 h at 37° C. without shaking. Each logphase culture was diluted to deliver a final bacterial density of 5×10$^5$ CFU per mL. To perform the tests, a dilution series of the indicated antimicrobial agent in CAMHB was prepared from a stock solution containing 10 mg/mL of the compound in DMSO. The final concentrations of the natural product were between 0.625 and 80 μg/mL. These were chosen because we knew that the compound was active against *V. cholerae* within this range. Dilutions of known antimicrobial compounds were similarly chosen based on the reported MIC's for the bacterium in question. An MIC 2000 inoculator (DynaTech) was used to accurately dispense 1.5 μL of bacterial culture into 100 μL of CAMHB alone or supplemented with an antimicrobial agent in a 96 well plate. The plates were prepared in duplicate and incubated overnight at 37° C. A positive control for growth containing no antimicrobial compound but the relevant amount of DMSO and a negative growth control containing no bacteria were also prepared for each assay. The MIC was determined visually as the lowest antimicrobial agent concentration that prevented bacterial growth. The *M. tuberculosis* MIC was determined by the fluorometric microplate-based Alamar blue assay (MABA) in 7H9 liquid media containing casein (0.1% wt/vol) and lacking Tween 80 (7H9-Casein-ADC) (Ananthan et al., Tuberculosis (Edinb) (2009) 89: 334-353; Collins et al., Antimicrob Agents Chemother (1997) 41: 1004-1009).

Microdilution Alamar Blue Assay for *M. tuberculosis*

Briefly, 1 mL of *M. tuberculosis* cell stock was added to 49 mL of 7H9-TW80-ADC media and incubated for 4-5 days at 37° C. with shaking (120 rpm) until an OD$_{600}$ of 0.6-0.8 (#3-4 McFarland turbidity standard) was reached. The cells were then washed twice with PBS and resuspended in 7H9-Casein-ADC to a final concentration of 2×10$^5$ cells/mL. 100 μl of the cell suspension was inoculated into the wells of clear-bottomed, 96-well microplates preloaded with 100 μl of 7H9-Casein-ADC media containing appropriate dilutions of the test compound. Initial compound dilutions were prepared in DMSO, and subsequent two-fold dilutions were directly performed in the microtiter plates used for the assay. To determine if bacterial densities were adequate for the assay, 32.5 μl of Alamar blue solution (10× Alamar blue dye, 20% Tween 80, 8×PBS, pH 7) were added to a control well after 6-7 days of growth at 37° C. If the control well remained blue or turned purple and/or had a fluorescence reading <17,500 fluorescence units (FU) after 18-24 hours of further growth at 37uC, additional control wells were tested daily until the well turned pink and the fluorescence reading was greater than 17,500 FU's. At this point, the Alamar blue solution was added to the entire plate, and the fluorescence was measured after overnight incubation. All fluorescence measurements were performed in an HTS7000 Plus BioAssay Reader (Perkin Elmer) in bottom-reading mode with excitation at 550 nm and emission at 595 nm. Percent inhibition was defined as (experimental well FU−media only FU)/(bacteria only FU−media only FU)×100. The lowest drug concentration effecting ≥90% inhibition was considered the MIC.

Fungal Identification by Internal Transcribed Spacer Amplification (ITS) and Sequencing For fungal identification, the fungus isolate, C1223-D, was cultured on agar as described above for 26 days. The mycelium was then retrieved and ground to a fine powder in liquid nitrogen. Genomic DNA was extracted using the Wizard Genomic DNA Purification Kit (Promega), and the large subunit ribosomal DNA was amplified by PCR using primers LR5 (5'-TCCTGAGGGAAACTTCG-3') (SEQ ID NO 3) and LROR (5'-ACCCGCTGAACTTAAGC-3') (SEQ ID NO: 4) as well as their reverse complements. The PCR products were submitted for sequence analysis (Genewiz), and the resulting sequences were used in a BLAST search against deposited sequences. These sequences are provided below as SEQ ID NO 1 and 2.

```
LR5 as 5' primer (SEQ ID NO 1):
    TCGATTAGTCTTTCGCCCCCATGCCCATATTTGACGATCGATTT
GCACGTCAGAACCGCTGCGAGCCTCCACCAGAGTTTCCTCTGGCTTCACC
CTATACAGGCATAGTTCACCTTCTTTCGGGTCCGGCCCCGTATGCTCTTA
CTCAAATCCATCCGAGAACATCAGGATCGGTCGGAGATGCGCCGAAGCTC
TCTCCTACGTTCACTTTCATTACGCGTAGGGGTTTGACACCCGAACACTC
GCATACGAAGACGACTCCTTGGTCCGTGTTTCAAGACGGGTCGCTGATGA
CCATTACGCCAGCATCCTTGCAGAAGCGCGAACCTCAGTCGACCCCAGGG
TATTACGCAGCGGGCTATAACACTCCCGGAGGAGCCACATTCCCGAAGCC
```

-continued

```
TTTATCCCCGGGGCCAACTGATGCTGGCCTGAGCCGGCAGAGTGCACCA

CCGAGAACGATGGATGATCAACCGGCCCAAGTCTGGTCATGAGCGCTTCC

CTTTCAACAATTTCACGTACTGTTTAACCCTCTTTTCAAAGTGCTTTTCA

TCTTTCGATCACTCTACTTGTGCGCTATCGGTCTCTGGCCGGTATTTAGC

TTTAGAAGACGTATACCTCCCATTTAGAGCAGCATTCCCAAACTACTCGA

CTCGTCGAAGGAGTTTCACAGAGGCTTAGCGACCAACCGTACGGGGCTCT

CACCCTCTATGGCGTCCCGTTCCAGGGAACTCGGAAGGCACCTCGCCAGN

NCATCCTCTGCAAATTACAACTCGGGCCGGGGGCCAGATTTCAAATTTGA

GCTGTTGCCGCTTCACTCGCCGTTACTGAGGCAATCCCTGTTGGTTTCTT

TTCCTCCGCTTATTGATATGCTA

LROR as 5' primer (SEQ ID NO 2):
     TGCCTCAGTAACGGCGAGTGAAGCGGCAACAGCTCAAATTTGAA

ATCTGGCCCCCGGCCCGAGTTGTAATTTGCAGAGGATGTTTCTGGCGAGG

TGCCTTCCGAGTTCCCTGGAACGGGACGCCATAGAGGGTGAGAGCCCCGT

ACGGTTGGTCGCTAAGCCTCTGTGAAACTCCTTCGACGAGTCGAGTAGTT

TGGGAATGCTGCTCTAAATGGGAGGTATACGTCTTCTAAAGCTAAATACC

GGCCAGAGACCGATAGCGCACAAGTAGAGTGATCGAAAGATGAAAAGCAC

TTTGAAAAGAGGGTTAAACAGTACGTGAAATTGTTGAAAGGGAAGCGCTC

ATGACCAGACTTGGGCCGGTTGATCATCCATCGTTCTCGGTGGTGCACTC

TGCCGGCTCAGGCCAGCATCAGTTGGCCCCGGGGGATAAAGGCTTCGGGA

ATGTGGCTCCTCCGGGAGTGTTATAGCCCGCTGCGTAATACCCTGGGGTC

GACTGAGGTTCGCGCTTCTGCAAGGATGCTGGCGTAATGGTCATCAGCGA

CCCGTCTTGAAACACGGACCAAGGAGTCGTCTTCGTATGCGAGTGTTCGG

GTGTCAAACCCCTACGCGTAATGAAAGTGAACGTAGGAGAGAGCTTCGGC

GCATCTCCGACCGATCCTGATGTTCTCGGATGGATTTGAGTAAGAGCATA

CGGGGCCGGACCCGAAAGAAGGTGAACTATGCCTGTATAGGGTGAAGCCA

GAGGAAACTCTGGTGGAGGCTCGCAGCGGTTCTGACGTGCAAATCGATCG

TCAAATATGGGGCATGGGGGGCGAAAGACTAATCGAACCTTCTAGTAGCT

GGTTTCCGC
```

Development of a High Throughput Screen

In the clinical microbiology laboratory, one of the characteristics used to distinguish *V. cholerae* from other *Vibrio* species is its ability to ferment sucrose on thiosulfate-citrate-bile salts-sucrose (TCBS) plates, which contain the pH indicators bromothymol blue and thymol blue. As the pH of a solution decreases below 7.1 for bromothymol blue and 8.0 for thymol blue, these aromatic compounds, which are weak acids, gain a proton resulting in a color change from blue to yellow. This process is reversible. Therefore, if the pH is increased again, the color of these weak acids will return to blue. Such pH indicators are often used as reporters of bacterial fermentation. See, e.g., Mandal et al., Asian Pac J Trop Med (2011) 4: 573-580; McCormack et al., J Infect Dis (1974) 129: 497-500; Pfeffer et al., Lett Appl Microbiol (2003) 36: 150-151.

We recently showed that transport of sucrose by *V. cholerae* depends entirely on a phosphotransfer cascade known as the phosphoenolpyruvate phosphotransferase system or PTS, which also regulates biofilm formation. See Houot et al., J Bacteriol (2008) 190: 311-320. Houot et al., J Bacteriol (2010) 192: 3055-3067. We were interested in developing a reporter medium that would allow us to identify compounds that inhibit transport through the PTS, sugar fermentation, or bacterial growth. Therefore, we added bromothymol blue and thymol blue, the pH indicators found in TCBS agar, to minimal medium containing sucrose (pH-$MM^{Suc}$). Based on the pKa values of bromothymol blue and thymol blue, we predicted that the medium would be yellow at pH<7.1, when both indicators are protonated. We predicted that the medium would be green at a pH between 7.1 and 8.0 because bromothymol blue would be blue due to deprotonation, while thymol blue would remain yellow. At pH>8.0, when both indicators are deprotonated, we anticipated that the medium would be blue.

Incubation of wild-type *V. cholerae* in this medium caused a change in color from green to yellow due to fermentation (FIG. 1). When the PTS mutant, which cannot utilize sucrose, was incubated in $pHMM^{Suc}$, the medium turned blue, indicating an increase in the pH. This is the result of amino acid catabolism which generates ammonia, a weak base. We hypothesized that these visible differences in the color of the medium at low and high pH were the result of a change in absorbance at a wavelength in the visible range. To identify this wavelength, we scanned the visible spectra of $pHMM^{Suc}$ alone, pH-$MM^{Suc}$ incubated with wild-type bacteria, and pH-$MM^{Suc}$ incubated with a PTS mutant. As shown in FIG. 1, the maximum difference in absorbance for all these conditions was observed at a wavelength of 615 nm. We based our screen on this observation. It consisted of a room temperature incubation of *V. cholerae* in $MM^{Suc}$ supplemented with bromothymol blue and thymol blue, and measurements of $A_{615}$ at 6 and 20 hrs.

To validate the screen, a pilot assay was conducted in 384 well microtiter dishes using plates 1568 and 1569 from the Prestwick Collection, a commercial library. Wild-type *V. cholerae* with no added compound was used as a positive control, while a PTS mutant, which is unable to transport sucrose, was used as a negative control. One column of each dish was reserved for replicate positive controls and another for replicate negative controls. To evaluate the performance of our assay, we calculated a Z' factor for each microtiter dish. This factor reflects the difference between positive and negative control measurements and is used to determine whether the size of a response (e.g. change in absorbance) is large enough to be useful in a HTS. See, e.g., Zhang et al., J Biomol Screen (1999) 4: 67-73. A Z' factor between 1 and 0.9 is considered excellent, while one between 0.9 and 0.7 is considered good. For these tests, the Z' factor ranged from 0.785 to 0.914, suggesting that this was a good to excellent assay. Therefore, we proceeded with the HTS.

HTS of Natural Products

We carried out a screen of a library of partially purified extracts from diverse Costa Rican organisms. The library consisted of 39,314 extracts arrayed in 384-well plates at a concentration of ~15 mg/mL in DMSO. Each library plate contained extracts in columns 1-22 and DMSO only in columns 23 and 24. Compounds were pin-transferred into a 384-well plate pre-filled with pH-$MM^{Suc}$. Columns 1-23 were then inoculated with wild-type *V. cholerae*, and column 24 was inoculated with a PTS mutant. Columns 23 and 24 served as fermentation-positive and fermentation-negative controls, respectively. Each plate of extracts was tested in duplicate. A measurement was considered to be both statistically and biologically significant if it deviated by at least three standard deviations from the mean measurement, which was calculated from measurements derived from all the compounds screened. Statistical analysis performed after completion of the screen yielded a Z' factor with a mean value of 0.808±0.088, indicating a very robust screen. We identified 126 unique extracts with possible activity against *V. cholerae*.

Secondary Screens

Compounds that increase the pH of the medium or that absorb in the visible spectrum could be a source of false positives in this assay. These were easily eliminated by detailed monitoring of the change in $A_{615}$ over time. In addition, the following secondary screens were designed to identify (i) inhibitors of PTS sugar transport, (ii) inhibitors of sugar fermentation, or (iii) inhibitors of bacterial growth. To distinguish between extracts that inhibited PTS-dependent sugar transport and those that delayed fermentation, we compared medium acidification in $MM^{Glu}$ with that in $MM^{Suc}$ in the presence of crude extracts with the following rationale. After hydrolysis, the fermentation pathway of sucrose is similar to that of glucose. However, unlike sucrose, glucose is transported by both PTS-dependent and PTS-independent means. See Houot et al., J Bacteriol (2008) 190: 311-320. Therefore, we predicted that, in the presence of specific inhibitors of the PTS, medium acidification would proceed more slowly in $MM^{Suc}$ than in $MM^{Glu}$. In contrast, inhibitors of fermentation should behave similarly in both media. Because pyruvate is transported independently of the PTS and is not fermented, we used growth in $MM^{Pyr}$ to identify extracts that inhibited bacterial replication. Each assay was performed in duplicate, and each reported value represents the average of two experimental replicates. To account for the variability of initial absorbance measurements, experimental data were normalized to the initial $A_{615}$ for each well.

Figure 3A:
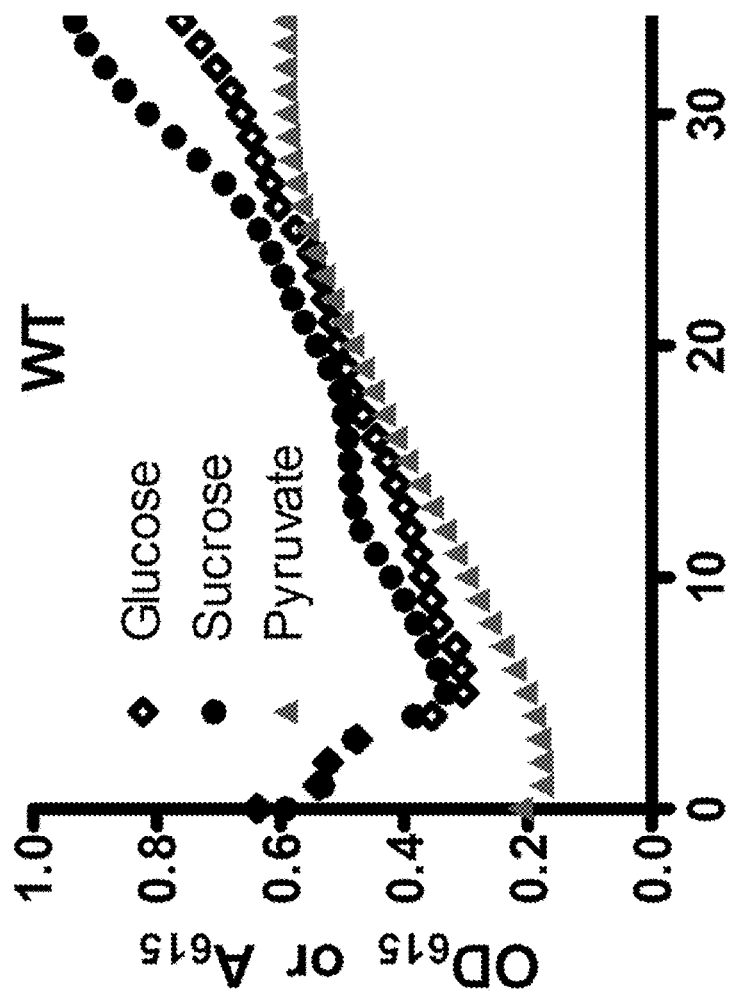
FIGS. 3A-3E depict exemplary results for the secondary screen. Bacteria were grown in MMPyr, pHMMSuc, or pH-MMGlu. OD615 measurements of cultures in MMPyr reflect the ability of cells to grow in the presence of extract, in this example representative extract CR1223D, while absorbance measurements in pH-MMSuc and pH-MMGlu reflect the ability of cells to transport and ferment these sugars in the presence of extract. Data are shown for wild-type *V. cholerae* and a PTS mutant in the absence of extract (FIGS. 3A,3B) or for wild-type *V. cholere* in the presence of extract (FIG. 3C) that interfere with sugar transport and fermentation, (FIG. 3D) inhibit bacterial growth (bacteriostatic), or (Figure E) kill bacteria (bactericidal).

We first compared the performance of wild-type *V. cholerae* (WT) and a PTS mutant (Δ PTS) in our proposed secondary screens (FIGS. 3A and B). In $MM^{Suc}$ and $MM^{Glu}$ containing wild-type *V. cholerae* alone (FIG. 3A), the $A_{615}$ initially decreased but then began to rise after approximately 5 hours of incubation. We hypothesized that the initial decrease in $A_{615}$ represented acidification of the medium due to sugar fermentation, while the subsequent increase in $A_{615}$ reflected depletion of the sugar supply and initiation of amino acid catabolism as well as cell growth.

Figure 3B:
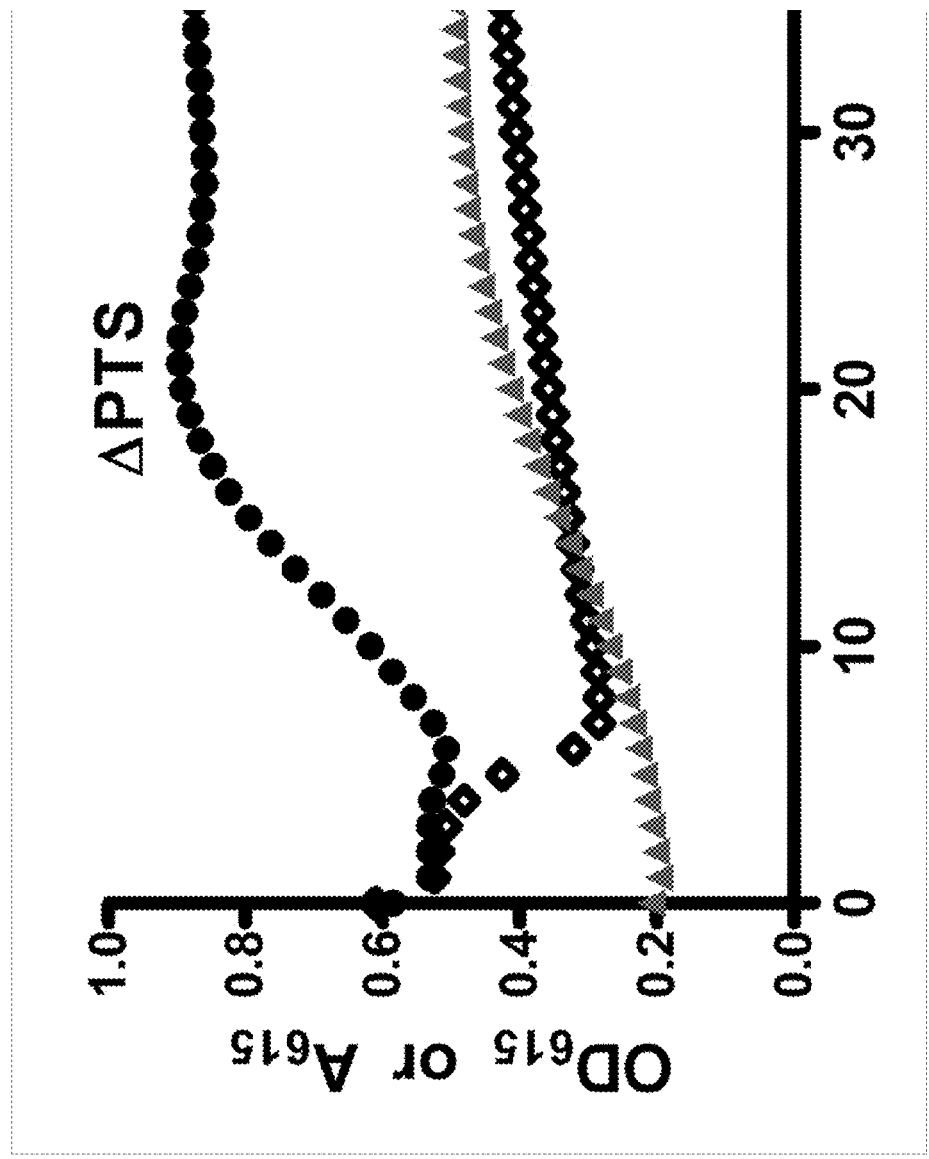

An increase in $A_{615}$ was observed during incubation of the PTS mutant in $MM^{Suc}$ due to its inability to transport and consequently ferment sucrose (FIG. 3B). Unlike sucrose, glucose can be transported by the PTS mutant. Therefore, in $MM^{Glu}$, the $A_{615}$ of the medium initially decreased, albeit more slowly than was observed for incubation with wild-type *V. cholerae*. Lastly, wild-type *V. cholerae* and the PTS mutant grew equally well in $MM^{Pyr}$.

Figure 3C:
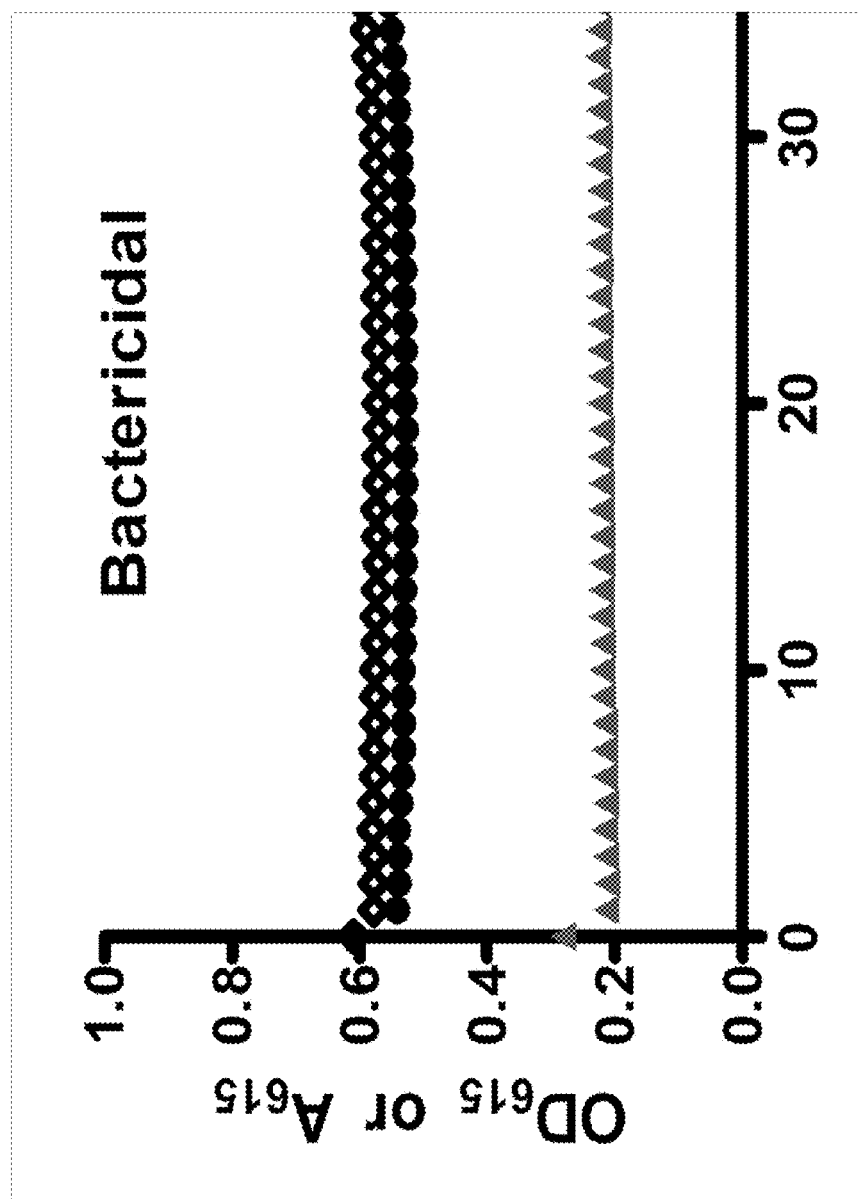
Figure 3D:
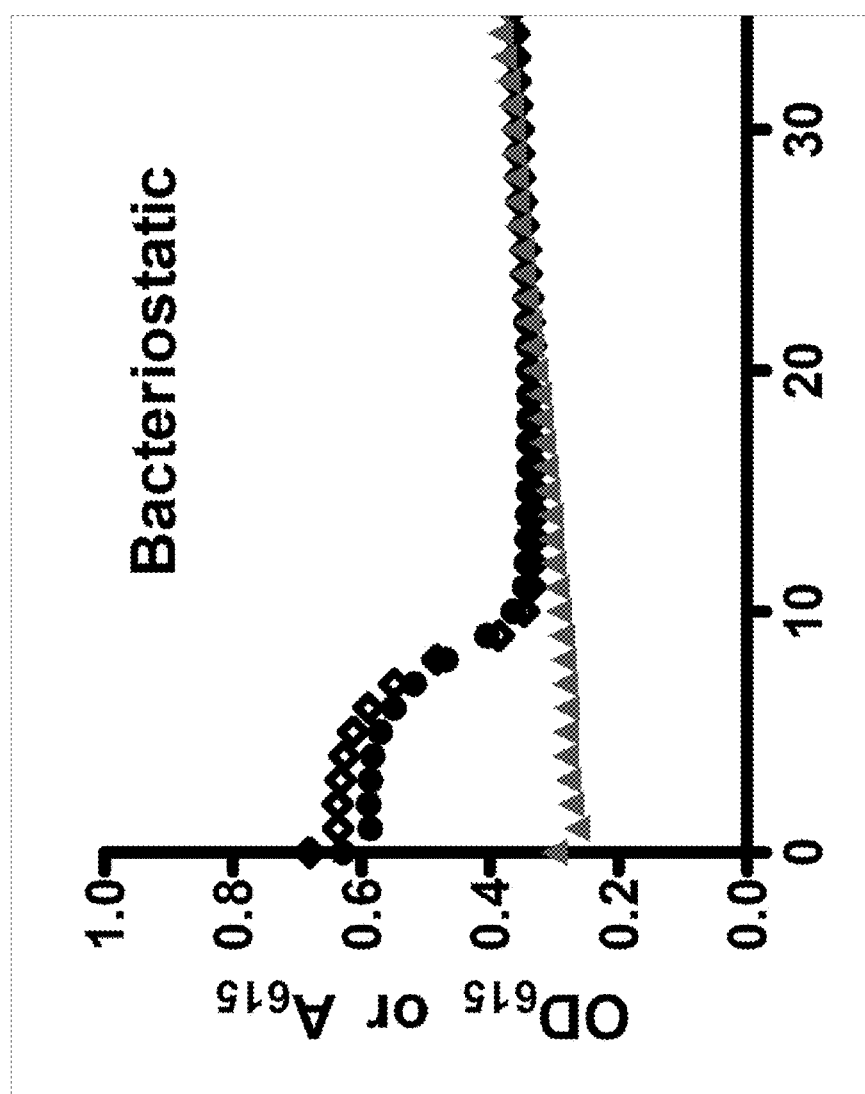
Figure 3E:
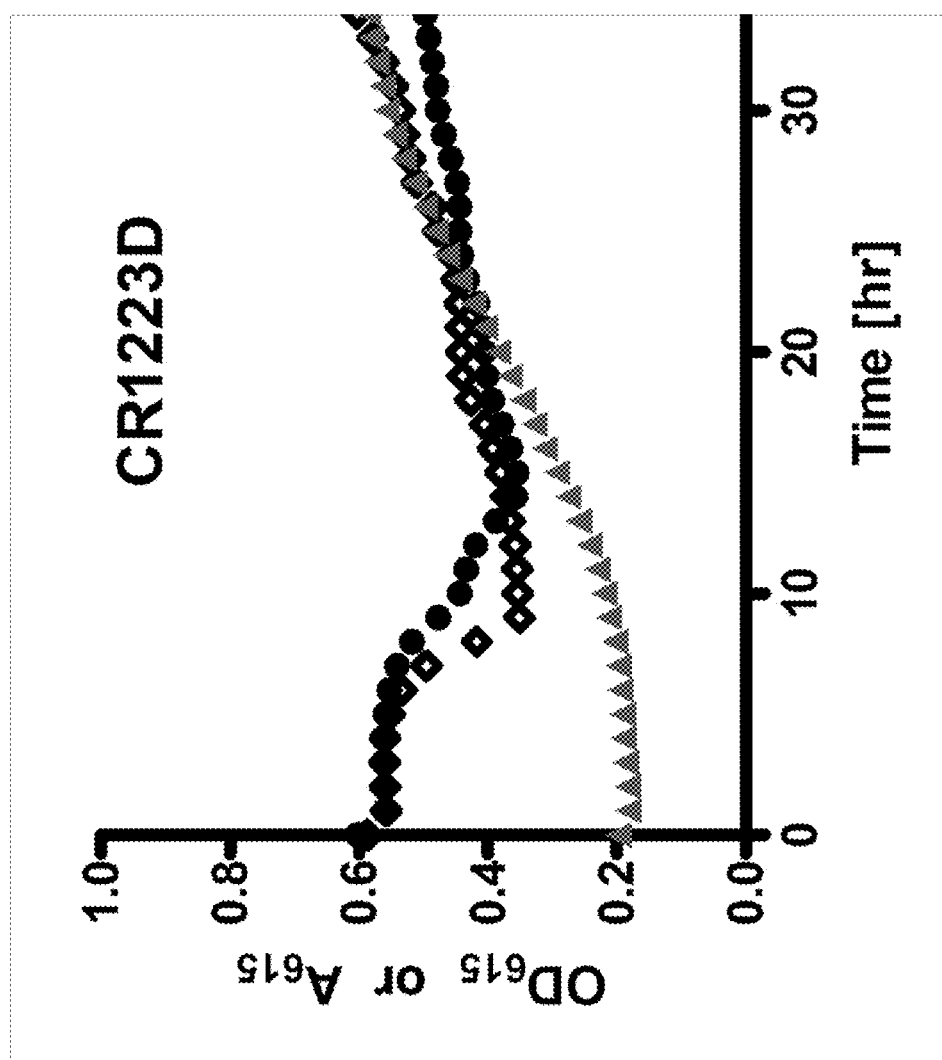

Our secondary screen yielded 49 extracts with reproducible effects on medium acidification by *V. cholerae* (see Table 3, FIG. 3C, and FIGS. 6A-6M). These included (i) one extract, CR1223-D (FIG. 3C), which delayed medium acidification by sucrose fermentation more than that by glucose fermentation, (ii) 34 extracts that blocked growth in pyruvate but not medium acidification, and (iii) fourteen extracts that blocked growth in pyruvate as well as medium acidification (representative traces for extract CR1223-D are shown in FIGS. 3C to 3E). We hypothesized that CR1223-D might contain an inhibitor of PTS transport. Furthermore, we reasoned that medium acidification in the absence of cell growth, as was seen in group (ii), reflected the presence of viable bacteria whose growth was inhibited. Therefore, we hypothesized that these extracts were bacteriostatic. The absence of both medium acidification and cell growth, as was observed in group (iii), suggested the absence of viable bacteria. We hypothesized that these extracts were bactericidal, although it is formally possible that these extracts contained compounds that inhibited both sugar transport and cell growth while preserving the viability of bacterial cells.

Because of our interest in sugar metabolism, we subsequently focused on characterization of CR1223-D. This extract was derived from an unclassified endophytic fungus harvested from the twig of *Neomirandea angularis*, a host plant from the Asteraceae family (isolate C1223-D). Amplification, sequencing (see SI), and alignment of the ITS region using Mega suggested that this fungus was most closely related to the environmental fungi, *Septofusidium herbarum* and *Acremonium alternatum*. For use of Mega, see Tamura et al., Mol Biol Evol (2011) 28: 2731-2739.

Extracts of fungal isolate C1223-D were prepared and fractionated as described in the Materials and Methods. High resolution mass spectrometry, infrared and ultraviolet spectrometry, and $^1H$ and $^{13}C$ nuclear magnetic resonance spectroscopy were used to identify compound 1 as 6-propyl gentisyl alcohol or 2-(hydroxymethyl)-3-propyl hydroquinone, compound 2 as 5-hydroxy-4-(hydroxymethyl)-2-methyl 2,3-dihydrobenzofuran, and compound 3 as 2-(hydroxymethyl)-3-propyl benzoquinone (FIG. 4). The physical properties and NMR spectra of these compounds are described herein.

TABLE 3

Listing of 49 natural extracts with reproducible effects on medium acidification by *V. cholerae* identified in secondary screens

| Run | Plate | Well | Library | Reagent | ID | Activity |
|---|---|---|---|---|---|---|
| BS-43936-1-01 | 1928 | M22 | NCDDG2 | NCDDG | 4845 | bacteriostatic |
| BS-43936-1-02 | 1930 | E15 | NCDDG2 | NCDDG | 6980 | bacteriostatic |
| BS-43936-1-03 | 1931 | G09 | NCDDG2 | NCDDG | 7340 | bacteriostatic |
| BS-43936-1-06 | 1932 | H13 | NCDDG2 | NCDDG | 9106 | bacteriostatic |
| BS-43936-1-14 | 1939 | J22 | ICBG Fungal Extracts 5 | ICBG | 10285 | bacteriostatic |
| BS-43936-1-22 | 1955 | E05 | Medicines for Malaria Venture | MMV | 16596 | bacteriostatic |
| BS-43936-1-23 | 1956 | E12 | Medicines for Malaria Venture | MMV | 17040 | bacteriostatic |
| BS-43936-1-24 | 1957 | G01 | Medicines for Malaria Venture | MMV | 17309 | bacteriostatic |
| BS-43936-1-26 | 1960 | E01 | Medicines for Malaria Venture | MMV | 21154 | bacteriostatic |
| BS-43936-1-28 | 1960 | P04 | Medicines for Malaria Venture | MMV | 21474 | bacteriostatic |
| BC-43936-1-34 | 1970 | N01 | ICBG Fungal Extracts 9 | ICBG | 12959 | bactericidal |
| BC-43936-2-01 | 1971 | A17 | ICBG Fungal Extracts 9 | ICBG | 13077 | bactericidal |
| BS-43879-11 | 1972 | D15 | ICBG Fungal Extracts 9 | ICBG | 18366 | bacteriostatic |
| BS-43936-2-05 | 1975 | B20 | ICBG Fungal Extracts 9 | ICBG | 19776 | bacteriostatic |
| BS-43936-2-06 | 1975 | C21 | ICBG Fungal Extracts 9 | ICBG | 19524 | bacteriostatic |
| BS-43936-2-07 | 1977 | D15 | ICBG Fungal Extracts 9 | ICBG | 20447 | bacteriostatic |
| BC-43936-2-08 | 1977 | H02 | ICBG Fungal Extracts 9 | ICBG | 20550 | bactericidal |

TABLE 3-continued

Listing of 49 natural extracts with reproducible effects on medium acidification by *V. cholerae* identified in secondary screens

| Run | Plate | Well | Library | Reagent | ID | Activity |
|---|---|---|---|---|---|---|
| BS-43936-2-10 | 1980 | D10 | ICBG Fungal Extracts 11 | ICBG | 23616 | bacteriostatic |
| BC-43936-2-12 | 1983 | P05 | ICBG Fungal Extracts 11 | ICBG | 26584 | bactericidal |
| BC-43936-2-16 | 1994 | L22 | Medicines for Malaria Venture 2 | MMV | 36993 | bactericidal |
| BS-43936-2-22 | 2000 | C13 | ICBG Fungal Extracts 12 | ICBG | 31343 | bacteriostatic |
| BS-43936-2-24 | 2001 | L12 | ICBG Fungal Extracts 12 | ICBG | 32002 | bacteriostatic |
| BC-43907-07 | 2002 | N19 | ICBG Fungal Extracts 12 | ICBG | 33857 | bactericidal |
| BS-43879-23 | 2003 | D06 | ICBG Fungal Extracts 12 | ICBG | 34235 | bacteriostatic |
| BC-43936-2-26 | 2004 | H22 | ICBG Fungal Extracts 12 | ICBG | 35617 | bactericidal |
| BC-43936-2-28 | 2005 | O01 | ICBG Fungal Extracts 12 | ICBG | 35739 | bactericidal |
| CP-43936-2-30 | 2014 | A05 | NCDDG4 | NCDDG | 25277 | differential sucrose and glucose fermentation |
| BS-43936-2-32 | 2015 | M05 | NCDDG4 | NCDDG | 27202 | bacteriostatic |
| BS-43907-09 | 2016 | A08 | NCDDG4 | NCDDG | 31065 | bacteriostatic |
| BC-43907-10 | 2018 | H17 | NCDDG4 | NCDDG | 33466 | bactericidal |
| BS-43936-2-34 | 2018 | J02 | NCDDG4 | NCDDG | 33557 | bacteriostatic |
| BC-43936-3-01 | 2019 | M19 | NCDDG4 | NCDDG | 40709 | bactericidal |
| BS-43936-3-05 | 2028 | D20 | NCDDG5 | NCDDG | 42521 | bacteriostatic |
| BS-43907-13 | 2028 | F08 | NCDDG5 | NCDDG | 42526 | bacteriostatic |
| BS-43907-16 | 2038 | F02 | Medicines for Malaria Venture 4 | MMV | 45564 | bacteriostatic |
| BS-43936-3-11 | 2041 | A22 | ICBG Fungal Extracts 14 | ICBG | 46432 | bacteriostatic |
| BS-43936-3-12 | 2041 | B18 | ICBG Fungal Extracts 14 | ICBG | 46606 | bacteriostatic |
| BS-43936-3-16 | 2041 | J15 | ICBG Fungal Extracts 14 | ICBG | 46561 | bacteriostatic |
| BC-43907-18 | 2042 | A07 | Medicines for Malaria Venture 5 | MMV | 47663 | bactericidal |
| BS-43907-19 | 2044 | A19 | ICBG Fungal Extracts 15 | ICBG | 47751 | bacteriostatic |
| BS-43907-20 | 2045 | O09 | ICBG Fungal Extracts 15 | ICBG | 48175 | bacteriostatic |
| BC-43907-21 | 2046 | J09 | ICBG Fungal Extracts 15 | ICBG | 48670 | bactericidal |
| BC-43907-23 | 2049 | K06 | NCDDG7 | NCDDG | 48943 | bactericidal |
| BS-43936-3-20 | 2049 | O16 | NCDDG7 | NCDDG | 48970 | bacteriostatic |
| BC-43936-3-21 | 2053 | C01 | Medicines for Malaria Venture 6 | MMV | 46697 | bactericidal |
| BS-43936-3-23 | 2053 | E01 | Medicines for Malaria Venture 6 | MMV | 46708 | bacteriostatic |
| BS-43936-3-25 | 2053 | J06 | Medicines for Malaria Venture 6 | MMV | 46996 | bacteriostatic |
| BS-43936-3-24 | 2053 | M17 | Medicines for Malaria Venture 6 | MMV | 46760 | bacteriostatic |
| BS-43936-3-27 | 2054 | O07 | Medicines for Malaria Venture 6 | MMV | 50868 | bacteriostatic |

Activity of Compounds 1, 2, and 3 Against *V. cholerae*

To determine which of these compound(s) was responsible for the activity of CR1223-D, we performed medium acidification and growth assays in the presence of various concentrations of compounds 1 through 3. Conditions were tested in duplicate in each experiment, and two experimental replicates were performed on separate days. Reproducibility was excellent. The result of one experiment is shown in FIGS. 5A-5F. Compound 1 inhibited medium acidification at a concentration of 134 μM and completely blocked medium acidification at a concentration of 261 μM. At higher concentrations, compound 1 was able to completely inhibit growth of *V. cholerae*. To determine whether this represented bacteriostatic or bactericidal activity, dilutions of the cell suspensions were plated on LB agar after 20 hours of growth in $MM^{Pyr}$ supplemented with compound 1 at a concentration of 383 μM. No CFU were documented after 24 hours of incubation at 37° C., indicating that compound 1 inhibited fermentation and possibly sugar transport at lower concentrations and was bactericidal at higher concentrations. Thus, we concluded that compound 1 was responsible for the inhibitory activity of CR1223-D detected in our HTS assay. We have named compound 1 mirandamycin, after the genus of the host plant of the producing fungus.

In Vitro Antimicrobial Activity of Mirandamycin Against Other Bacterial Pathogens To evaluate the antimicrobial efficacy of mirandamycin against a broader panel of bacterial pathogens, we measured the activity of compound 1 against clinical strains of *E. coli, P. aeruginosa*, carbapenemase-producing *K. pneumonia*, methicillin-resistant *S. aureus*, and *M. tuberculosis*. As shown in Table 4, mirandamycin was most active against Gram-positive organisms but also had some activity against the more sensitive Gram-negative rods. Susceptibility of these organisms to known antibiotics is shown for comparison.

TABLE 4

Minimum inhibitory concentrations (MICs) against selected bacterial pathogens

| | | MIC (μg/mL) | | | | TMP/ |
|---|---|---|---|---|---|---|
| Species | ATCC | MIR | LEVO | AMP | IMI | SMX |
| *E. coli* | 25922 | 80 | 0.019 | 2.5 | 1.25 | 0.125 |
| *P. aeruginosa* | 27853 | 80 | 1.25 | >80 | 5 | >16 |
| *K. pneumoniae* carbapenemase positive | BAA-1705 | >80 | >80 | >80 | >80 | >16 |
| MRSA | BAA-976 | 10 | 0.312 | >80 | 1.25 | 0.062 |
| *V. cholerae* PW357 | — | 40 | <0.005 | 2.5 | 1.25 | >16 |
| *M. tuberculosis* H37Rv [*] | 27294 | 25 | 0.25 | 0.25 | 100 | 2 |

[*] MIC was determined by Alamar Blue Assay as described in Material and Methods; Mirandamycin (MIR), levofloxacin (LEVO), ampicillin (AMP), imipenem (IMI), bactrim (TMP/SMX), isoniazid (INH), pyrazinamide (PZA), ethambutol: ETH.

We have developed and implemented a simple, inexpensive, and robust HTS for antibacterial agents based on a spectrophotometric assay of sugar fermentation, a process present only in viable bacteria. Secondary screens allowed us to easily distinguish between bactericidal and bacteriostatic compounds as well as those that blocked sugar fermentation but did not decrease growth or viability.

As compared with other HTS for antibacterial compounds, this screen has several advantages. First of all, the screen uses whole cells rather than purified targets. See, e.g., Pereira et al., *Antimicrob Agents Chemother* (2009) 53: 2306-2311. Secondly, it is an assay for cell viability and, therefore, is biased toward bactericidal agents. See, e.g., Campbell Curr Protoc Chem Biol (2010) 3:100115; Ferrand et al., J Biomol Screen (2011) 16: 637-646. Thirdly, because it does not require cell growth, it is rapid. Lastly, the screen does not require expensive fluorescent reporters of cell viability.

As a proof of principle, we identified several extracts with antibacterial activity. Fractionation of one of these derived from an endophytic fungus led to the identification of three novel natural products. One of these natural products, a hydroquinone that we have called mirandamycin (compound 1), has antibacterial activity against a wide range of difficult to treat pathogens including *P. aeruginosa*, MRSA, and *M. tuberculosis*.

Quinones and their corresponding reduced forms, the hydroquinones, are components of eukaryotic and bacterial electron transport chains. In *V. cholerae*, ubiquinone-8 is reduced by the Na+-translocating NADH:ubiquinone oxidoreductase (NQR) at the cytoplasmic face of the inner membrane. The corresponding hydroquinone then diffuses across the inner membrane where it is oxidized by one of several possible quinol oxidases, discharging protons to the periplasmic space. The resulting quinone is recycled to the inner membrane. See, e.g., Hase et al., Biochim Biophys Acta (2001) 1505: 169-178. Therefore, quinones are reduced at the cytoplasmic face of the inner membrane and the corresponding hydroquinones are oxidized at the periplasmic face.

The bactericidal secondary metabolite identified here, mirandamycin (compound 1), is a hydroquinone, closely related to homogentisic acid. We hypothesize that the antibacterial activity of mirandamycin is the result of an interaction with an outward facing bacterial quinol oxidase. One possibility is that single electron oxidation of mirandamycin by a quinol oxidase results in formation of a semiquinone intermediate, which can then react with molecular oxygen to produce a toxic superoxide radical. Inhibition of bacterial quinol oxidase by mirandamycin is another possible antibacterial mechanism.

Quinones are known to be toxic to both mammalian and bacterial cells. See, e.g., Bolton et al., Chem Res Toxicol (2000) 13: 135-160. Liebeke et al., Mol Microbiol (2008) 69: 1513-1529. First of all, they can undergo single electron reduction at the cytoplasmic face of bacterial cell membranes to form semiquinones. Secondly, quinones can interact with thiol-containing compounds to form adducts. Interestingly, the oxidized quinone form of mirandamycin reported here (compound 3) demonstrated little to no antibacterial activity with the assay described. It is possible that compound 3 does not enter bacterial cells and, therefore, is not reduced to mirandamycin under the conditions used.

Organisms that survive successfully in close proximity to bacterial pathogens have been a rich source of potent antibacterial natural products. Presented here is an easily implemented, sensitive HTS that rapidly identified a large number of antibacterial extracts from environmental samples. This screen was used to identify a quinol with activity against multiple pathogens. In this era of rising resistance to existing antibiotics, approaches such as this will be increasingly relied on to fill our antimicrobial pipeline.

Preparation of Analogs

The natural products isolated and described herein may be chemically or enzymatically functionalized to provide various analogs.

As exemplified in Schemes 1 and 2, one may globally react the free hydroxyls present in a compound in order to provide a compound with the same non-hydrogen substitution, or differentially protect the phenolic hydroxyl groups, in order to provide a compound with different non-hydrogen substitution. While Schemes 1 and 2 depicts reactions with an exemplary compound of Formula (I) and (IV), such a method is extendible to all compounds of the present invention, including compounds of Formula (II) and (III), as described herein.

Alkylation, acylation, halogenation, and ring cyclization reactions are also well known reactions and may be utilized to provide additional analogs of the natural products disclosed herein. See, e.g., Scheme 3, and generally *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Scheme 1.

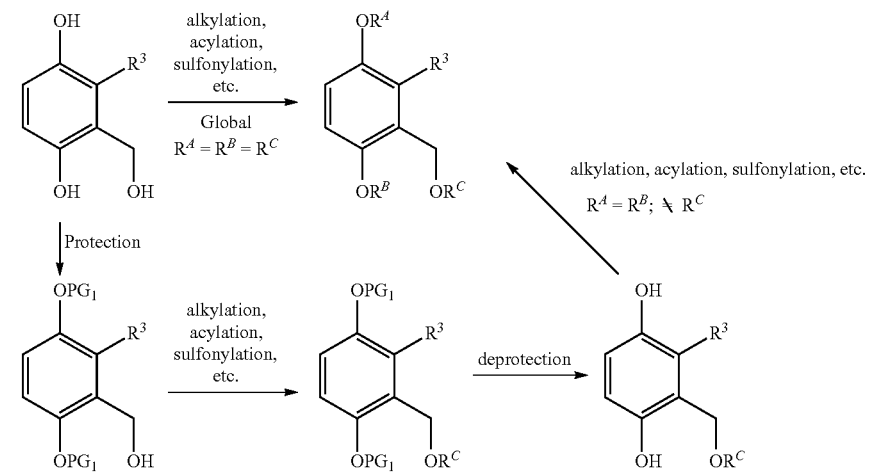

$PG_1$ = oxygen protecting group;
See *Protecting Groups in Organic Synthesis*, T. W. Greene and P. G. M. Wuts, 3rd edition, John Wiley & Sons, 1999, incorporated herein by reference Scheme 2.
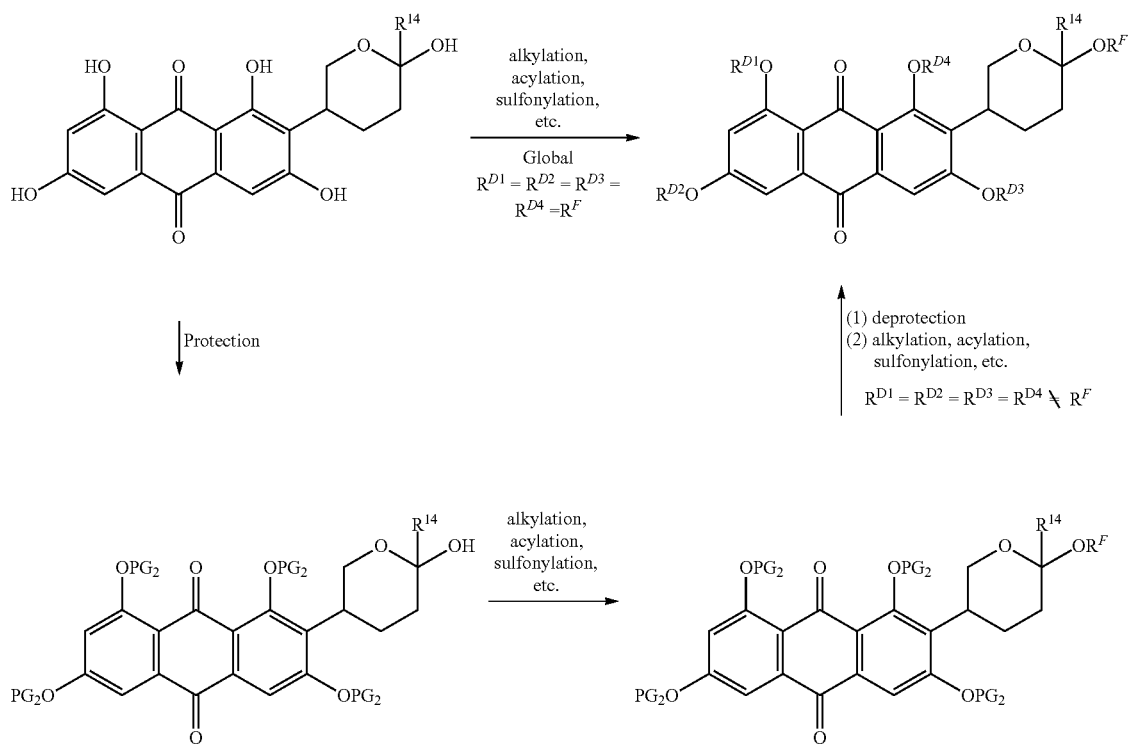
$PG_2$ = oxygen protecting group;
See Protecting Groups in Organic Synthesis, T. W. Greene and P. G. M. Wuts, 3rd edition, John Wiley & Sons, 1999, incorporated herein by reference
Scheme 3.
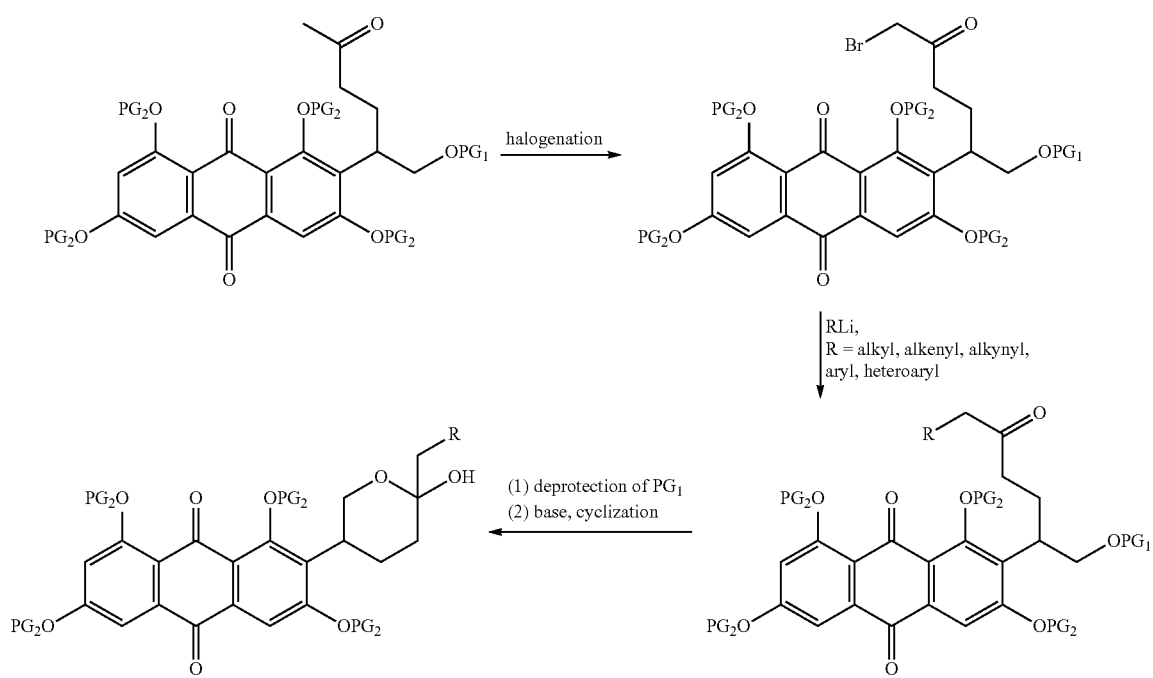
$PG_1$, $PG_2$ = oxygen protecting group;
See Protecting Groups in Organic Synthesis, T. W. Greene and P. G. M. Wuts, 3rd edition, John Wiley & Sons, 1999, incorporated herein by reference

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a bacterial infection in a subject comprising administering an effective amount of a compound of Formula (I-b):

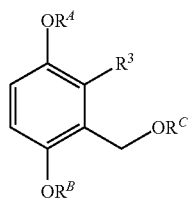

(I-b)

or pharmaceutically acceptable salt thereof, to the subject;

wherein:
each occurrence of $R^A$, $R^B$, and $R^C$ is hydrogen;
$R^3$ is unsubstituted $C_2$-$C_{10}$alkyl,
wherein the bacterial infection is an *Escherichia coli, Pseudomonas aeruginosa, Vibrio cholerae*, methicillin-resistant *Staphylococcus aureus*, or *Mycobacterium tuberculosis* infection.

2. The method of claim 1 wherein $R^3$ is unsubstituted $C_2$-$C_6$alkyl.

3. The method of claim 1 wherein the compound is of Formula (I-c):

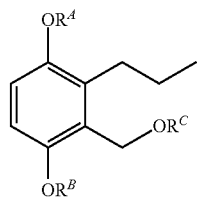

(I-c)

or a pharmaceutically acceptable salt thereof.

4. The method of claim 1 wherein the compound is:

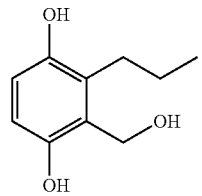

or a pharmaceutically acceptable salt thereof.

5. The method of claim 1, wherein the bacterial infection is a methicillin-resistant *Staphylococcus aureus* infection.

6. The method of claim 1, wherein the bacterial infection is a *Mycobacterium tuberculosis* infection.

7. The method of claim 1, wherein the bacterial infection is a methicillin-resistant *Staphylococcus aureus* infection or a *Mycobacterium tuberculosis* infection.

* * * * *

UNITED STATES PATENT AND TRADEMARK OFFICE
CERTIFICATE OF CORRECTION

PATENT NO. : 9,359,275 B2
APPLICATION NO. : 13/776144
DATED : June 7, 2016
INVENTOR(S) : Paula I. Watnick et al.

Page 1 of 1

It is certified that error appears in the above-identified patent and that said Letters Patent is hereby corrected as shown below:

*In the Specification:*

At column 1, lines 15-17, replace the current "Government Support":

"This invention was made with government support under AI50032 awarded by the National Institutes of Health. The government has certain rights in the invention."

with the following:

--This invention was made with government support under AI50032, NIHU54 AI057159, and NIHU01 TW007404, awarded by the National Institutes of Health. The government has certain rights in the invention--.

*In the Claims:*

Claim 1, column 81, line 26, "hydrogen;" should be changed to --hydrogen; and--.

Signed and Sealed this
Ninth Day of August, 2016

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 867
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (744)..(745)
<223> OTHER INFORMATION: n is a, c, g, or t

<400> SEQUENCE: 1
tcgattagtc tttcgccccc atgcccatat ttgacgatcg atttgcacgt cagaaccgct      60
gcgagcctcc accagagttt cctctggctt caccctatac aggcatagtt caccttcttt     120
cgggtccggc cccgtatgct cttactcaaa tccatccgag aacatcagga tcggtcggag     180
atgcgccgaa gctctctcct acgttcactt tcattacgcg taggggtttg acacccgaac     240
actcgcatac gaagacgact ccttggtccg tgtttcaaga cgggtcgctg atgaccatta     300
cgccagcatc cttgcagaag cgcgaacctc agtcgacccc agggtattac gcagcgggct     360
ataacactcc cggaggagcc acattcccga agcctttatc ccccggggcc aactgatgct     420
ggcctgagcc ggcagagtgc accaccgaga acgatggatg atcaaccggc ccaagtctgg     480
tcatgagcgc ttcccttca acaatttcac gtactgttta acccctcttt caaagtgctt      540
ttcatctttc gatcactcta cttgtgcgct atcggtctct ggccggtatt tagctttaga     600
agacgtatac ctcccattta gagcagcatt cccaaactac tcgactcgtc gaaggagttt     660
```

```
cacagaggct tagcgaccaa ccgtacgggg ctctcaccct ctatggcgtc ccgttccagg    720
gaactcggaa ggcacctcgc cagnncatcc tctgcaaatt acaactcggg ccggggggcca    780 gatttcaaat ttgagctgtt gccgcttcac tcgccgttac tgaggcaatc cctgttggtt    840
tcttttcctc cgcttattga tatgcta                                         867
```

<210> SEQ ID NO 2
<211> LENGTH: 853
<212> TYPE: DNA
<213> ORGANISM: Artificial Sequence
<220> FEATURE:
<223> OTHER INFORMATION: Synthetic Polynucleotide

<400> SEQUENCE: 2

```
tgcctcagta acggcgagtg aagcggcaac agctcaaatt tgaaatctgg ccccccggccc    60 gagttgtaat ttgcagagga tgtttctggc gaggtgcctt ccgagttccc tggaacggga    120
cgccatagag ggtgagagcc ccgtacggtt ggtcgctaag cctctgtgaa actccttcga    180
cgagtcgagt agtttgggaa tgctgctcta aatgggaggt atacgtcttc taaagctaaa    240
taccggccag agaccgatag cgcacaagta gagtgatcga agatgaaaa gcactttgaa     300 aagagggtta aacagtacgt gaaattgttg aaagggaagc gctcatgacc agacttgggc    360
cggttgatca tccatcgttc tcggtggtgc actctgccgg ctcaggccag catcagttgg    420
ccccggggga taaaggcttc gggaatgtgg ctcctccggg agtgttatag cccgctgcgt    480
aataccctgg ggtcgactga ggttcgcgct tctgcaagga tgctggcgta atggtcatca    540
gcgacccgtc ttgaaacacg gaccaaggag tcgtcttcgt atgcgagtgt tcgggtgtca    600 aaccccctacg cgtaatgaaa gtgaacgtag gagagagctt cggcgcatct ccgaccgatc    660
ctgatgttct cggatggatt tgagtaagag catacggggc cggacccgaa agaaggtgaa    720
ctatgcctgt atagggtgaa gccagaggaa actctggtgg aggctcgcag cggttctgac    780
gtgcaaatcg atcgtcaaat atggggcatg gggggcgaaa gactaatcga accttctagt    840
agctggtttc cgc                                                        853
```

<210> SEQ ID NO 3
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 3

```
tcctgaggga aacttcg                                                    17
```

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4

```
acccgctgaa cttaagc                                                    17
```